(12) United States Patent
Wilde et al.

(10) Patent No.: US 11,034,990 B2
(45) Date of Patent: Jun. 15, 2021

(54) OPTIMIZED HOST CELLS FOR THE PRODUCTION OF GLUTATHIONE

(71) Applicant: Lallemand Inc., Rexdale (CA)

(72) Inventors: Caroline Wilde, Montreal (CA); Corinne Cluis, Montreal (CA)

(73) Assignee: Lallemand Inc., Rexdale (CA)

( * ) Notice: Subject to any disclaimer, the term of this patent is extended or adjusted under 35 U.S.C. 154(b) by 0 days.

(21) Appl. No.: 16/089,347

(22) PCT Filed: Mar. 31, 2017

(86) PCT No.: PCT/CA2017/050397
§ 371 (c)(1),
(2) Date: Sep. 27, 2018

(87) PCT Pub. No.: WO2017/165978
PCT Pub. Date: Oct. 5, 2017

(65) Prior Publication Data
US 2019/0055589 A1 Feb. 21, 2019

Related U.S. Application Data

(60) Provisional application No. 62/315,796, filed on Mar. 31, 2016.

(51) Int. Cl.
| | | |
|---|---|---|
| *C12P 21/02* | (2006.01) | |
| *C07K 14/39* | (2006.01) | |
| *C12N 9/88* | (2006.01) | |
| *C12N 15/52* | (2006.01) | |
| *C12N 15/81* | (2006.01) | |
| *C12P 1/02* | (2006.01) | |

(52) U.S. Cl.
CPC .............. *C12P 21/02* (2013.01); *C07K 14/39* (2013.01); *C12N 9/88* (2013.01); *C12N 15/52* (2013.01); *C12N 15/81* (2013.01); *C12P 1/02* (2013.01); *C12Y 401/02005* (2013.01)

(58) Field of Classification Search
None
See application file for complete search history.

(56) References Cited

FOREIGN PATENT DOCUMENTS

| CN | 101220338 A | 7/2008 |
|---|---|---|
| CN | 101245363 A | 8/2008 |

OTHER PUBLICATIONS

Zou et al., "Tumor Necrosis Factor-alpha-induced targeted proteolysis of cystathionine beta-synthase modulates redox homeostasis", Journal of Biological Chemistry 278(19): 16802-16808 (2003) (Year: 2003).*
Kasak et al., "Assessing computational predictions of the phenotypic effect of cystathionine-beta-synthase variants", Human Mutations 40: 1530-1545 (2019) (Year: 2019).*
Dawes et al., "Functional genomics in yeast," *Microbiology Australia* pp. 51-54, 2007.
Delic et al., "Overexpression of the transcription factor Yap1 modifies intracellular redox conditions and enhances recombinant protein secretion," *Microbial Cell* 1(11):376-386, 2014.
Orumets et al., "YAP1 over-expression in *Saccharomyces cerevisiae* enhances glutathione accumulation at its biosynthesis and substrate availability levels," *Biotechnol. J.* 7:566-568, 2012.
Orumets, "Molecular mechanisms controlling intracellular glutathione levels in baker's yeast *Saccharomyces cerevisiae* and a random mutagenized glutathione over-accumulating isolate," Thesis on Natural and Exact Sciences B140, Tallinn University of Technology, Tallinn, Estonia Nov. 16, 2012 (90 pages).
Vogl et al., "Regulation of *Pichia pastoris* promoters and its consequences for protein production," *New Biotechnology* 30(4):385-404, 2013.
Zhu et al., "Endogenic oxidative stress response contributes to glutathione over-accumulation in mutant *Saccharomyces cerevisiae* Y518," *Appl Microbiol Biotechnol* 99:7069-7078, 2015.
Aitken et al., "Role of Active-Site Residues Thr81, Ser82, Thr85, Gln157, and Tyr158 in Yeast Cystathionine β-Synthase Catalysis and Reaction Specificity," *Biochemistry* 43:1963-1971, 2004.
Blank et al., "Sulfur Metabolism Actively Promotes Initiation of Cell Division in Yeast" *PLoS ONE* 4(11): 2009, 7 pages.
Jhee et al,. "Domain Architecture of the Heme-Independent Yeast Cystathionine β-Synthase Provides Insights into Mechanisms of Catalysis and Regulation," *Biochemistry* 39:10548-10556, 2000.
Kuge et al., "Regulation of the Yeast Yap1p Nuclear Export Signal Is Mediated by Redox Signal-Induced Reversible Disulfide Bond Formation," *Molecular and Cellular Biology* 21(18):6139-6150, 2001 (13 pages).
Kuge et al., "Regulation of yAP-1 nuclear localization in response to oxidative stress," *The EMBO Journal* 16(7):1710-1720, 1997.
Monschau et al., "Threonine Aldolase Overexpression plus Threonine Supplementation Enhanced Riboflavin Production in *Ashbya gossypii,*" *Applied and Environmental Microbiology* 64(11):4283-4290, 1998.
Nisamedtinov et al., "Metabolic changes underlying the higher accumulation of glutathione in *Saccharomyces cerevisiae* mutants," *Appl Microbial Biotechnol* 89:1029-1037, 2011.
Nisamedtinov et al., "Multilevel Control of GSH Accumulation in Mutant and Wild-type Strains of *S. cerevisiae* Under Conditions of Smooth Cysteine Addition," 2nd *International Conference on Industrial Biotechnology* 20: 2010, 6 pages.
Oluwatosin et al., "Mutations in the CYS4 Gene Provide Evidence for Regulation of the Yeast Vacuolar H+-ATPase by Oxidation and Reduction in Vivo" *The Journal of Biological Chemistry* 272(44):28149-28157, 1997.
Orumets et al., "The effect of YAP1 over-expression on glutathione accumulation in *Saccharomyces cerevisiae,*" *Biotechnol J.* 7(4): 2012, 8 pages.

(Continued)

*Primary Examiner* — Anand U Desai
(74) *Attorney, Agent, or Firm* — Seed IP Law Group LLP

(57) ABSTRACT

The disclosure concerns a genetically modified host cell for the production and accumulation of glutathione (GSH). The genetically modified host cell can allow the expression of a mutated Cys4p whose activity is increased. In addition or alternatively, the genetically modified host cell can express a mutated Yap1p whose translocation from the nucleus to the cytoplasm is reduced. Furthermore, in addition or alternatively, the genetically modified host cell can express an heterologous threonine aldolase (Gly1p).

37 Claims, 22 Drawing Sheets
Specification includes a Sequence Listing.

(56) References Cited

OTHER PUBLICATIONS

Sugiyama et al., "The Yap1p-dependent Induction of Glutathione Synthesis in Heat Shock Response of *Saccharomyces cerevisiae*," *The Journal of Biological Chemistry* 275(20):15535-15540, 2000.
Suzuki et al., "Identification and characterization of genes involved in glutathione production in yeast," *Journal of Bioscience and Bioengineering* 112(2):107-113, 2011.
Tang et al., "Three-pathway combination for glutathione biosynthesis in *Saccaromyces cerevisiae*," *Microbial Cell Factories* 14(139): 2015, 12 pages.
Van Maris et al., "Overproduction of Threonine Aldolase Circumvents the Biosynthetic Role of Pyruvate Decarboxylase in Glucose-Limited Chemostat Cultures of *Saccharomyces cerevisiae*," *Applied and Environmental Microbiology* 69(4):2094-2099, 2003.
Wang et al., "The Effect of Intracellular Amino Acids on GSH Production by High-cell-density Cultivation of *Saccharomyces cerevisiae*," *Appl Biochem Biotechnol* 168:198-205, 2012.

\* cited by examiner

| | |
|---|---|
| Saccharomyces_cerevisiae | MTK-SEQQADSRHNVIDLVGNTPLIALKKLPKALGIKPQIYAKLELYNPGGSIKDRIAKS |
| Saccharomyces_bayanus | MTK-SEQQTDSRHDVIDLVGNTPLIALKKLPKALGIRPQIYAKLEIYNPGGSIKDRIAKS |
| Cyberlindnera_jadinii | MSERDSKIPALNENILELIGNTPLVKLNKVPQSLGIKPQVLAKVELFNAGGSIKDRIALR |
| Torulaspora_delbrueckii | ------MTVDTRTNVIDLVGNTPMVELTKLPAALGVKPRVYAKLELYNPGGSIKDRIAKS |
| Zygosaccharomyces | ------MVVDTRTNVIDLVGNTPLIELKTLPKALGIKPKVYAKLELYNPGGSIKDRIAKT |
| Scheffersomyces_stipitis | -----MSSVPPLYENALDLIGNTPLIKLNKIPQSYGIKAKVYAKVELFNAGGSIKDRISKN |
| Kluyveromyces_lactis | -----MGYDTRHDVIDIVGNTPLIRIQKLPKAIGIKPKVYAKLELYNPGGSIKDRIAKS |
| Pichia_pastoris | MSDNNQPLPPVSNSILEHIGKTPIVKLNRIPKILNLKPQVYAKVELFNSGGSIKDRIALR |
| | .: :.*.:*: . * *:.**: ::. :* **.:.:* ********: |

Catalytic domain

| | |
|---|---|
| Saccharomyces_cerevisiae | MVEEAEASGRIHPSRSTLIEPTSGNTGIGLALIGAIKGYRTIITLPEKMSNEKVSVLKAL |
| Saccharomyces_bayanus | MVEEAEASGRIHPSRSTLIEPTSGNTGIGLALIGAIKGYRTIITLPEKMSNEKVSVLKAL |
| Cyberlindnera_jadinii | MVEEAEREGRIKPGY-VLCEPTSGNTGIGLALAGAVKGYRVIITLPEKMSNEKVSVLKAL |
| Torulaspora_delbrueckii | MIEYAEAAGEIHPDRTTLIEPTSGNTGIGLALIGAIKGYRTIITLPEKMSNEKVSVLKAL |
| Zygosaccharomyces | MIEYAEKNGEIHPDRTTLIEPTSGNTGIGLALIGAIKGYRTIITLPEKMSNEKVSVLKAL |
| Scheffersomyces_stipitis | MILEAEKSGRIKPGY-TLIEPTSGNTGIGLAIVAAVKGYRTIITLPEKMSNEKVSVLKAL |
| Kluyveromyces_lactis | MIEAAEEEGIIHPSRSTLIEPTSGNTGIGLALIGAIKGYRTIITLPEKMSNEKVSVLKAL |
| Pichia_pastoris | MVEQAEKEGRIKPGY-TLIEPTSGNTGIGLALVGAVKGYRTIITLPEKMSNEKVAVLKAL |
| | *::**. * *.****:*** .* .:* .******.:** |

Figure 7

Catalytic domain

| Species | Sequence |
|---|---|
| Saccharomyces_cerevisiae | GAEIIRTPTAAAWDSPESHIGVAKKLEKEIPGAVILDQYNNMMNPEAHYFGTGREIQRQL |
| Saccharomyces_bayanus | GAEIIRTPTAAAWDSPESHIGVAKKLEKEIPGAVILDQYNNPMNPEAHYFGTGREIQRQL |
| Cyberlindnera_jadinii | GAEIIRTPNEAAFDSPESHIGVAKRLEKEIKNCVILDQYGNINNPDAHYTTGYEIWKQT |
| Torulaspora_delbrueckii | GAEIVRTPTEAAWDSPESHIGVAERLQKEIPGAVILDQYNNPRNPEAHYLGTGKEIQDQL |
| Zygosaccharomyces | GAEIVRTPTSAAWDSPESHIGVAKRLEKEIPGAVILDQYNNPRNPEAHYYGTGKEIQEQL |
| Scheffersomyces_stipitis | GAEIIRTPTEAAWDAPESHIGVAKKLEKEIPNSVILDQYSNPANPDAHYYGTGFEIWEQT |
| Kluyveromyces_lactis | GAEIIRTPTAAAWDSPESHIGVALRLEKEIPGGIILDQYNNMKNPEAHYFGTGKEIHHQL |
| Pichia_pastoris | GAEIIRTPTEAAWDSPESHIGVARRLEKEIPNAVILDQYGNVNNPDAHFYTTGAEIWDQT |
|  | \*\*\*\*:\*\*\*.\* \*\*:\*\*:\*\*\*\*\*\*\*\*\* :\*:.\*\*\*\*\*\*\* :  \*\*:.\* \*\*\*\*\* :\* |

Catalytic domain

| Species | Sequence |
|---|---|
| Saccharomyces_cerevisiae | EDLNLFDNLRAVVAGAGTGGTISGISKYLKEQNDKIQIVGADPFGSILAQPENLNKTDIT |
| Saccharomyces_bayanus | QDLNLFDNLRAVVAGAGTGGTISGISKYLKEQNDKIQIVGADPFGSILAVPENLNKTDVT |
| Cyberlindnera_jadinii | G-----GKLNALVAGAGTGGTITGIAKYIKEQNEKIQIVGADPLGSILAVPENLNKTDVT |
| Torulaspora_delbrueckii | EKLGKFDSLKAVIAGAGTGGTISGISRYLKEQDPSITVVGADPVGSILAVPETLNKTDVT |
| Zygosaccharomyces | QNLNEFDNLKAVIAGAGTGGTITGISKWLKGKNEDIKIVGADPVGSILAQPQSLNETSAP |
| Scheffersomyces_stipitis | K----GKVTHLVAGAGTGGTITGISRYLKEQNDNITIVGADPFGSILAQPESLNKTDVG |
| Kluyveromyces_lactis | EDLSLFSKLKAVVAGAGTGGTISGISKYIKEQNDKIAIVGADPKGSILAQPESINTS-TE |
| Pichia_pastoris | N-----GKVTHVVAGAGTGGTITGIAKFLKSKNPNIQIIGADPHGSILALPESLNTS-NE |
|  |  ::  :.\*.\*:.\*\*\*\*\*\*\*::\*\*::\*:\*::. \*\*\*\*\* \*\*\*\*\* \*\*:\*\*\* .: |

Figure 7 (continued)

Catalytic domain

```
Saccharomyces cerevisiae    DYKVEGIGYDFVPQVLDRKLIDVWYKTDDKPSFKYARQLISNEGVLVGGSSSGSAFTAVVK
Saccharomyces_bayanus       DYKVEGIGYDFIPDVLNRDLIDVWYKTDDKPSFKYARQLISNEGVLVGGSSSGSAFAAVMK
Cyberlindnera_jadinii       QYKVEGIGYDFIPDVLKRESVDQWYKTEDQESFTLARRIISEEGILVGGSSSGSAMAAVVK
Torulaspora_delbrueckii     GYKVEGIGYDFVPNVLDRSLVDVWYKTEDKASFKYARQLISNEGVLIGGSSSGSAFTALLK
Zygosaccharomyces           EYKVEGIGYDFVPKVLNRNEIDTWYKTDDKDSFVYARQLISNEGVLVGGSSSGSAFSALVK
Scheffersomyces_stipitis    GYLVEGIGYDFIPDVLNRKYVDNWIKTEDAESFKLARRIREEGILVGGSSSGSALQAALQ
Kluyveromyces_lactis        EYKVEGIGYDFVPKVLNRDSVDHWVKTDDKSSFKYARQLISNEGVLVGGSSSGSAFTALVD
Pichia_pastoris             QYKVEGIGYDFIPEVLDREIVDTWYKTDDKDSFKLARQLISEEGILVGGSSSGSALSAAVK
                            * :***:***:* ** .**::*:  .*  : *:*::*: *:*******:**** ::
```

Catalytic domain

```
Saccharomyces cerevisiae    YCEDHPELTEDDVIVAIFPDSIRSYLTKFVDDEWLKKNNLWDDDVLAREDSSKIEASTTK
Saccharomyces_bayanus       YCEDHPELTEDDVIVAIFPDSIRSYLTKFVDDEWLKKNDLWDDEILTREDASKPEASTNT
Cyberlindnera_jadinii       YCNDHPELTEKDTIVVFPDSIRSYLTKFADDEMKSNGFEINTKPAED-------------
Torulaspora_delbrueckii     YVAEHPELTEDDVLVVVFPDSIRSYLTKFVDDEWLKKNDLMDDEVLARVKQ-----TSTVT
Zygosaccharomyces           YAKDHPELDENDVLVAIFPDSIRSYLTKFVDDEWLKKNNLWSDDVLARVGTKG----PSNID
Scheffersomyces_stipitis    VAKD---LTEDDVVVVFPDSIRSYLSKFADDEWMKINNFAVDETSSSGNK-----------
Kluyveromyces_lactis        YCNEHPELTEDDVIVIFPDSVRSYLTKFVDDEWLKTNGLWDDAIATPIV--------QK
Pichia_pastoris             IIND-AKLDESAVVVVCPDSIRSYLTKFADDDMKLNGFTEDEPAPLKRK--------SSF
                            : .  :..:::*:: *** ***:** **:  :
```

Figure 7 (continued)

Regulatory domain

| Species | Sequence |
|---|---|
| Saccharomyces_cerevisiae | YADVFGNATVKD--LHLKPVVSVKETAKVTDVIKILKDNGFDQLPVLTE-DGKLSGLVTL |
| Saccharomyces_bayanus | YADVFGDATVKD--LHLKPVVSVKETAKVADVIKILKDNGFDQLPVLAE-DGKLSGLVIY |
| Cyberlindnera_jadinii | ----IQTETIAS--LNLKPVVAVYSDEKVQTVIKLLKDNGFDQLPVLAKGTEKLIGLITL |
| Torulaspora_delbrueckii | KKDPFNGAKVQD--LHLKPVVSVKESASLAEVIKILKDNAFDQLPVLTE-DGKLSGLVTL |
| Zygosaccharomyces | RKDPFHGATVQD--LKLKPVVSVKENAAVADAIQILRQNAFDQLPVLAE-DGKLSGLVTL |
| Scheffersomyces_stipitis | SDDFLASKTIRDLVAGKAPVVTVTLSDTVGKTFDLLHDNGFDQLPVLNN-SGKIVGLVTL |
| Kluyveromyces_lactis | ETDVFEDATVKD--LNLKPVVSVEEDASVATVIKILRDNSFDQLPVLTK-DGKLCGLVTL |
| Pichia_pastoris | SKDTLSSYTIKDLA--LKPVVSVTIDDSIESTINILQTKGFDQLPVLKN--DKLAGIVTL |
| | :  .:    : . .:****:*  : *:****** :   :  ** *: |

Regulatory domain

| Species | Sequence |
|---|---|
| Saccharomyces_cerevisiae | SELLRKLSINNSNNDNTIKGKYLDFKKLNNFNDVSSYN-ENKSGKKKFIKFDENSKLSDL |
| Saccharomyces_bayanus | MSC--------------------------------------------------------- |
| Cyberlindnera_jadinii | SKLLKSVSSGSVSLNDNIESIILDFRKLNNFDDVNLFN-DNKSSKKKFQQITTKTTLKEL |
| Torulaspora_delbrueckii | SLLLRKISNGTS-KDDSIKDIYFDFKKLNNFDQVSSYN-ENKSGKKKFTVETNGSKLSDL |
| Zygosaccharomyces | SQLLKKLSNGTATKEDKIKSFYIDFRKLNNFDDVSSYN-ENKSGKKKFVQFTNSSKLSDL |
| Scheffersomyces_stipitis | SKILKSLSTKKVQITNSIASVIIDFRKLADFEKSFTIAKESGFTKRSYEPITLDTPLALL |
| Kluyveromyces_lactis | SQLLKKLSTSK--DVSSIKSLFFDFRKLNNFDDISSYN-ADKSHKKIFVRFDVNTTLSEL |
| Pichia_pastoris | SQLLRLLSNKKIHLTSKVESAYFDFSKLENFEKSYNINKESTNKRREYQKITTSTTLAKL |

Figure 7 (continued)

| | Regulatory domain |
|---|---|
| Saccharomyces cerevisiae | NRFFEKNSSAVITD-GLKPIHIVTKMDLLSYLA------ |
| Saccharomyces bayanus | ------------------------------------- |
| Cyberlindnera jadinii | NKFFEKNACAIVTDENLKPVHVVTKVDLLDYFVGGI--- |
| Torulaspora delbrueckii | NSFFEKNSSAIITD-GLRPVHIVTKIDLLNYLA------ |
| Zygosaccharomyces | NNFFEKNSSAIITE-GSKPVHIVTKIDLLDYLI------ |
| Scheffersomyces stipitis | NKFFETNSNAIITDDELKPVQIVTKVDLISFLTKNVAF- |
| Kluyveromyces lactis | NSFFEKNSAAIITE-GLNPVHIVTKVDLLSYLAK----- |
| Pichia pastoris | NKFFETSSAAIVENDKGQPIHIVSKVDLLSFLASKGEFN |

Figure 7 (continued)

| Species | Sequence |
|---|---|
| Saccharomyces_cerevisiae | ------------MSVSTAKRSLDVVSPGSLAEFEGSKSRHDEIENE-HR |
| Saccharomyces_bayanus | ------------MSISAAKRSLDLVSSSSLAQSDDSVSHHDEVEND-HI |
| Saccharomyces_kudriavzevii | ------------MSVSTAKRSLDLASPGSLAEFDDSAAHHDEIENE-HR |
| Cyberlindnera_jadinii | ----------------MTEYAKRHTDSL-----LE--------NPE-SK |
| Torulaspora_delbrueckii | MERALPPLISRTSTRSNTSMSMSASTVKRPLE----------------- |
| Zygosaccharomyces_bailii | ------------MSATSAKRPLEPTVSLEFA------------------ |
| Schizosaccharomyces_pombe | ------MSGQTET---LSSTSNIPIAKAEPEQSADFSASHKKRGPVSDRSSR |
| Kluyveromyces_lactis | ------------MSTSTAKRPFDNKRAGSPDDGTDSDS----------- |
| Pichia_pastoris | ------------MSDVVNKR--------------------------A |

| Species | Sequence |
|---|---|
| Saccharomyces_cerevisiae | RT------GTRDGEDSEQPKKKGSKTSKKQDLDPETKQKRTAQNRAAQRAFRERKERKMK |
| Saccharomyces_bayanus | HD------DMHDNDNDQPRRKGSKTSKKQDLDPETKLKRTAQNRAAQRAFRERKERKMK |
| Saccharomyces_kudriavzevii | HD------STRDDDNEQPKKKGTKISKKQDLDPETKQKRTAQNRAAQRAFRERKERKMM |
| Cyberlindnera_jadinii | RP------EPDATATSEGVLKKPNKPGR-KPLDTEPKNKRTAQNRAAQRAFRERKERKMK |
| Torulaspora_delbrueckii | --------QSSSPMAPAAKGSKPGR-KPLDEETKNKRTAQNRAAQRAFRERKEKKMK |
| Zygosaccharomyces_bailii | ND------EAEKSPTSEEPRKKGGKPGR-KPLDSEAKNKRTAQNRAAQRAFRKRKEDHLK |
| Schizosaccharomyces_pombe | RTSSEEVDLMPNVDDEVDGDVKPKKIGR-KNSDQEPSSKRKAQNRAAQRAFRKKEDHLK |
| Kluyveromyces_lactis | --------GGNNSGSSPASKRRERKPGR-KPLETEAKDKRTAQNRAAQRAFRERRERKMK |
| Pichia_pastoris | AT------SSTQTNKRQELSSALTKPGR-KPVQTEPKDKRTAQNRAAQRAFRERKEKKMK |
|  | * : :: * ************:.: |

Basic domain

Figure 8

Leucine Zipper

```
Saccharomyces cerevisiae        ELEKKVQSLESIQQNEVEATFLRDQLITLVNELKKYRPET--RNDSKVLEY-LARRDPN
Saccharomyces bayanus           ELEKKVHSLESIQQENEVEATFLRDQLVTLVSELKKYRPET--RNDSKVLEY-LARRDPN
Saccharomyces kudriavzevii      ELEKKVQGLENIQQNEVEATFLRDQLVTLVNELKKYRPET--RNDSKVLEY-LASRDPN
Cyberlindnera jadinii           ELEEKITTLEDEKRFATTESEFLRLQVQMITQELAKHRGTTDL-SDIKLPLF-TSPTETN
Torulaspora delbrueckii         ELEDKVQSLEQANRDTVVESEFLRSQLLTLVNELKKYRPAK--ANDLQVLDY-LAKHERT
Zygosaccharomyces bailii        ELEEKVHALEEMNQQSLVETEFLRSQLVTLVNELKKYRPQN--QADSQVLEY-LAKTEND
Schizosaccharomyces pombe       ALETQVVTLKELHSSTTLENDQLRQKVRQLEEELRILKDGS------FTEMSLPHRNPS
Kluyveromyces lactis            ELEDKVSQLESLNKQSELETKFLRNQVTNLLSELKRYNPELPKKRDSILLDY-LAKQRKA
Pichia pastoris                 ELETKVEELERQKSQLNTESEFLRSQVETLTHELSKYRGET------DVLSL-LPTSIPQ
                                 *   *    ::    : ::  **  *   *                         :

Saccharomyces cerevisiae        L------LFSKNNVNHSNSEPIDTPNDDIQENVKQKMNFTFQYPLDNDNDDS----------
Saccharomyces bayanus           L------HPPNSNT-NNNSEPIVTPNDDIQKNVKQKMNFTFQYPLDNDD----NDG------
Saccharomyces kudriavzevii      L------PTSNNSTNSSSNRPIITPSEEIQENVRQKMNFTFQYALDND------S-------
Cyberlindnera jadinii           S------TPNSEVSTVLTSVGSDNELKRTQQEFSFEFPWSRKSSTTNS--KRSPN
Torulaspora delbrueckii         ----------------------EPTDKEIEQSVQKKMDFTFAFPWKDRKEAEAQ-------
Zygosaccharomyces bailii        N------DAAGQ-------QTRQELNSKELQESVRRKMSFTFAFPWKNEIKSEEK-AGSPA
Schizosaccharomyces pombe       LSS--------------------------LPTTGFSSNFAHMKDGISPQSNLHLSPN
Kluyveromyces lactis            S------IDSNPDFSAAANK---AANSKDSSTAISSSNFQFEFPWKMDP-------------
Pichia pastoris                 ESKKMVRTPSSNTTNSSSVGV-TPSSST--LRSSSSSGVYEFPWKLSNSQNPS--GSN-S
                                                                                           ::
```

Figure 8 (continued)

```
Saccharomyces cerevisiae      -----K---NVGKQLPSPNDPSHSAPMPINQTQK---KL----SDATDSSSATLDSLSNSND
Saccharomyces_bayanus         -----K---NMEKQLPSPNDPNHSAHVPIAPTQK---KL----SDATDSSTATLDSFSNNND
Saccharomyces_kudriavzevii    -----K---NLEKQLPSPNDPSHSAPIPTTQAQK---KS----SDATDSSTATLDSLSNSHD
Cyberlindnera_jadinii         ASNASS-----------------NNVPTLASDA-----------ST-----------
Torulaspora_delbrueckii       -----------AQHFPSGSSMLSSSSASVNSAA--------SP----SNK-------RR
Zygosaccharomyces_bailii      ATEQPR----NDNLQFPSPGSSSKSSSVSTSSSLSKKKIGLYTPGTTDSNANNNLSSSTS
Schizosaccharomyces_pombe     SIEKPNMHQNVLHNDRSADNLNHRYQVPPTLVDSNSAQGTLSPE---------------
Kluyveromyces_lactis          ----------SKIPSPSSDSTPSASTSILDN-----------------ANNKSVSSTNL
Pichia_pastoris               P--LDL----TKAGQLPSPTSINQNPGLITAESVKS-----------S----SV-----

Saccharomyces cerevisiae      V--LNNTPNSSTSMDWLDNVIYTNRF--------V-SGDDGS----------NSKTKNLDS
Saccharomyces_bayanus         V--LNITPNSSSSMDWLDNVMYTNKF--------V-AGGDQK------NASNESKSKPKGVDS
Saccharomyces_kudriavzevii    V--LNNTPNSSSSMDWLDNVIYTNRF--------V-AGGDGS----------KLEVKNVDS
Cyberlindnera_jadinii         ------CSSQSSP-----FDLYNSEEQNELPLFNKV-----------------VKDST
Torulaspora_delbrueckii       STASRSTSTSTSTTGMNDNVFYSDDAQKLPQFAIKGDST----------------AD
Zygosaccharomyces_bailii      NLNNGSFTPGSSSTGWMDNVFYNDDAQQLPQFYQSATDNSGTTNNKLLEDNTSVPYGYDS
Schizosaccharomyces_pombe     ------TPSSSDSPSNLYLN-YPKRKS-I----------------THLHHDC
Kluyveromyces_lactis          NHSRSSISNSSSPSNVNGLSSRKHS--------------NTLNLYQ-TQ
Pichia_pastoris               --------S---------------------SESPNSNIED
```

Figure 8 (continued)

```
Saccharomyces_cerevisiae       NMFSNDFNFENQFDEQVSEFCSKMNQVCGTRQCPIPKKPISALDKEV--FASSS--------
Saccharomyces_bayanus          NMFSNDFNFENQFDEQVSEFCSKMNQACGTKQCPIPKKSVHQLDKEV--FASSS--------
Saccharomyces_kudriavzevii     NMFSNNFNFENQFDEQVSEFCSKMNQVCGTRQCPIPKKPVSTLDQEV--FASSS--------
Cyberlindnera_jadinii          KMPTEKFNFSEHFDEGV-NFCSDLGKACGTRECPIPEVKSNTNTPLPVELDHND--------
Torulaspora_delbrueckii        PLFSNEFNFDDQFDEQVSQFCTKMNKACGTRECPIPGFTPQMASPQV---------------
Zygosaccharomyces_bailii       VTFSNQFNFDDQFDEQVSEFCAKLGQVCGTKDCPVPKQKTASSTPNI---------------
Schizosaccharomyces_pombe      SALSNGENGEDV--ADGKQFCQKLSTACGSIACSMLTKTTPHRASVD--ILSNLH-------
Kluyveromyces_lactis           SNVTSEFDFDSQFDESVSSFCSKLSMACGTKSNPIPKASPVSTPSSSDLLKPKSNSNVNI--
Pichia_pastoris                FLNSRNSNFDNRFDESVDGFCSNLGQACGNKDIPLPKETSSIRNPGV--IDSLS--------
                                  :.  : ..  : .  *:   . .*    :

Saccharomyces_cerevisiae       ---------------ILSSNSPALT-------NTWESHSN---------ITDNTPANV---
Saccharomyces_bayanus          ---------------VLSANSPVLT-------NTWDSHSN---------VTTNTPANI---
Saccharomyces_kudriavzevii     ---------------ILSANSPALT-------NTWESHSN---------ITANTPANI---
Cyberlindnera_jadinii          ------P-----LNSLEDPALD----FNFGTFDPTVAFANESSYADLFD--SHGESDPLSR
Torulaspora_delbrueckii        ---------------ASPQILT----------NSWDTVAS---------PA----------
Zygosaccharomyces_bailii       ---------------TNSPLVLS---------NTWGSPSK---------HQ----------
Schizosaccharomyces_pombe      ------------ESTVSPPMADES--------VQRSSE-----------VSKSIPNVE---
Kluyveromyces_lactis           TNHNNKINSKDLSSSAPLHDSASASALNNHDSVNAVSNQFSVDKQYNDSSHSQATPNG----
Pichia_pastoris                ------------------NFNSNSDIQTLFSPNSLQ--------NDPL-------------
```

Figure 8 (continued)

| | |
|---|---|
| Saccharomyces_cerevisiae | IATDATKYENSFSGFGRLGFDMSANHYVVNDNSTGSTDSTGSTGST------ |
| Saccharomyces_bayanus | TTN------GSSSSSFGQPGFDLNTNHYATNDKYTDNSD------------- |
| Saccharomyces_kudriavzevii | TTN------DTSLSGFGQLGFELTTSRHAAEENSTGNTDNDNNSGDSSNNKNNNNNNNNNN |
| Cyberlindnera_jadinii | ISH------------------------------------------------ |
| Torulaspora_delbrueckii | ------------FGQQS----------------------------------- |
| Zygosaccharomyces_bailii | ------------GEKIVTT--------------------------------- |
| Schizosaccharomyces_pombe | LSL--NVNQQFVSPFGG---------------------------------- |
| Kluyveromyces_lactis | LDNDSSVSAWQQPSFGQLGFRTDQLFDLDLDS-------------------- |
| Pichia_pastoris | ------------AEF------------------------------------- |

| | | |
|---|---|---|
| Saccharomyces_cerevisiae | ---GNKNKKNNNNSDDVLPFISESPFDMQVTNF------FSPGSTGIGN-NA-ASNTN |
| Saccharomyces_bayanus | ------NNKTNNYNDILPFISESPFDMQVTNF------FSPGTNNTTN-ANTTNSHN |
| Saccharomyces_kudriavzevii | NSNNNKNNNNNGDDGGVIPFISDSPFDMQVTNF------FSPGSTNNIN-IA-ASSAN |
| Cyberlindnera_jadinii | ----------------------------------------------------- |
| Torulaspora_delbrueckii | ----------------------------------LAPSKK--------Q |
| Zygosaccharomyces_bailii | --------------------V------SAPAPSDKT----AAAEG |
| Schizosaccharomyces_pombe | ----------------------TDSFPLPTDTGL---DSLFEPDSAIE-- |
| Kluyveromyces_lactis | ----------------ASPITKQKDNNYSTTNNTNSPAKADGMYWNFNTPLSN |
| Pichia_pastoris | -------------------DPTPIDQNLVFGL-------------------- |

Figure 8 (continued)

| Species | Sequence |
|---|---|
| Saccharomyces_cerevisiae | PSLLQSSKEDIPFINANLAFPDDNSTNIQLQPFSESQSQNKFDYDMFFRDSSKEGNNLFG |
| Saccharomyces_bayanus | PSLQQSTKDDIPFINTSLAFPDDNPTNIQLQPLSQSHQNKFDYDMFFRDSSKEGNNLFE |
| Saccharomyces_kudriavzevii | PSLSQNTKDDVPFINAGLAFPDENPTNIQLQPFSESQSQNKFDYDMFFRDSRAGNSLFE |
| Cyberlindnera_jadinii | ------------------------------------------------------------ |
| Torulaspora_delbrueckii | LIKTPPSQPELPFIDPTMAFPTDDDE-----------------GLFFRTH-RDENSLFA |
| Zygosaccharomyces_bailii | KDAGTTKSGELPFIDTSLAFPEEQD-------------------LFRDS-QPD-NLFA |
| Schizosaccharomyces_pombe | -------------------NSHLKNVVM-----------EPELFQAWREPAESLDK |
| Kluyveromyces_lactis | ------------------------------------------------------------ |
| Pichia_pastoris | MVSRNMQNPEIPFIDTGLAFPDYDDPLLDI--------------DGLFGDNKYHTDPLA |
|  | --------------NAPETNL--------------------------------------- |

| Species | Sequence |
|---|---|
| Saccharomyces_cerevisiae | EFLEDDDDD---------------KKAANMSDDESSLIKNQL--------INEEPELPKQYLQS- |
| Saccharomyces_bayanus | EFLEEDDDDDDDDGNDGNDNDGEAVNASDDESNLIKNKL--------INEEPQQQSQCHLS- |
| Saccharomyces_kudriavzevii | EFLEEEEDDDDDDNN------NEKATNASDDESSLIRNQL--------INEEPQPLNQNSLS- |
| Cyberlindnera_jadinii | ------------------------------------------------------------ |
| Torulaspora_delbrueckii | ELL-DEVEPTDN-----------------------NFVNENL--------INEEPSTTAVAEE- |
| Zygosaccharomyces_bailii | EFIEDEPERDDD--------------------------PFLAANL--------INEEPQGPQQQNIQ- |
| Schizosaccharomyces_pombe | EFFNDEGEIDDVEHNYFHNS-------NENGDLITNSLHGLDFLENANESFPEQMYPFI |
| Kluyveromyces_lactis | ---LKEEQENEQVEGD-----------------SDPIQAL--------INEEPSMPLCHDPA- |
| Pichia_pastoris | SLVTEESIFDPL----------------------RATSNSV-------SHSKPNPITTTSLH- |

Figure 8 (continued)

```
                                                                                    Cysteine-rich domain
Saccharomyces cerevisiae        ------VPGNESEISQKNGSSLQNADKINNGNDNDNDVVPSKEGSLLRCSEIWDRITTH
Saccharomyces_bayanus           ------TPKNGSEVLQN-------KNSSNSEDVNDNDNEVVPSKEGSLLRCSEIWDRITTH
Saccharomyces_kudriavzevii      ------SLNNEKETSPKTNSG---GTQNANDSDGNDNDNDVVPSKEGSLLRCSEIWDRITTH
Cyberlindnera_jadinii           -------------------------------------------------------------
Torulaspora_delbrueckii         ------------------------TRPKPKTETDVVPSRDGKLLKCSEVWDRITTH
Zygosaccharomyces_bailii        ---PQKHEQDQIQTQQQRQQQDAKQHQATDVADCDGVVPSRDGKLLKCSEVWDRITSH
Schizosaccharomyces_pombe       KHNKDYISNHPDEV--PPDGLPQKGKHDTSSQMPSENEIVPAKERAYLSCPKVWSKIINH
Kluyveromyces_lactis            ------ANAGASVSE---------T--DKLSNQEEIVQDIIPSNDGKLLKCSEVWDRITAH
Pichia_pastoris                 ------NLEAKHK-----------VPEADEDCNDNLDNMVVPNREGSLLKCSEIWERITTH Cysteine-rich domain
Saccharomyces cerevisiae        PKYSDIDVDGLCSEIMAKAKCSERGVVINAEDVQLALNKHMN-------------------
Saccharomyces_bayanus           PKYSDIDVDGLCSEIMAKAKCSERGVVINAEDVQLALNKHMN-------------------
Saccharomyces_kudriavzevii      PKYSDIDVDGLCSEIMAKAKCSERGVVINAEDVQLALNKHMN-------------------
Cyberlindnera_jadinii           -------------------------------------------------------------
Torulaspora_delbrueckii         PKYSAIDIDGLCGEIMTKAKCSEKGVVVQAEDVQRVLDKHMDV-----------------
Zygosaccharomyces_bailii        PKYTDMDIDGLCLEIMAKAKCSEKGVVVQAEDVQRALANRLD------------------
Schizosaccharomyces_pombe       PRFESFDIDDLCSKLKNKAKCSSSGVLLDERDVEAALNQFN-------------------
Kluyveromyces_lactis            PRYSDLDIDGLCLELRTKAKCSEKGVVVNAEDVQKALISHMQ------------------
Pichia_pastoris                 PRYSEIDIDGLCMELKHKAKCSESGVVVDDADVDSLLQRAALKYPIKTEPDVVDFSMFK
```

Figure 8 (continued)

```
Saccharomyces cerevisiae        ----------------------------MTEFELPPKYITAANDLRSDTFTTPTAEMIQAALEASIGDAVYGED
Saccharomyces bayanus           ----------------------------MTEFELPPKYITAANDLRSDTFTTPTAEMQAALEASIGDAVYGED
Saccharomyces kudriavzevii      ----------------------------MTEFELPPKYTTAANDLRSDTFTTPTPEMMQAALEASIGDAVYGED
Cyberlindnera jadinii           ----------------------------MTVAELKPYQSASNDFRSDTFTTPTEAMIKAALTASIGDSVYNED
Torulaspora delbrueckii         ----------------------------MTSQLPLAYASASNDLRSDTFTTPTPEMIEAALTASIGDAVYQED
Zygosaccharomyces bailii        ----------------------------MPDYELPPVYTTASNDLRSDTFTTPTPEMMQAGIAASIGDAVYQED
Schizosaccharomyces pombe       MSGSVTSTTTETRLCPSNQGSAKKYRPWNDFRSDTLLVPTDEMRRIMYEASDGDCVYEED
Kluyveromyces lactis            MT------ASDKKSTAAAPSEPAYTSAANDLRSDTFTTPTKEMLEAAFNASIGDAVYNED
Pichia pastoris                 ----------------------------MTKEDFPCANEFRSDTFTVPTASMIQSVALASVGDSVYAED
                                                             :.:*****.:.** .**.**.**.**

Saccharomyces cerevisiae        VDTVRLEQTVARMAGKEAGLFCVSGTLSNQIAIRTHLMQPPYSILCDYRAHVYTHEAAGL
Saccharomyces bayanus           VDTVRLEQTVARMAGKEAGLFCVSGTLSNQIAIRTHLMQPPYSILCDYRAHVYTHEAAGL
Saccharomyces kudriavzevii      VDTVRLEQTVARMAAKEAGLFCVSGTLSNQIAIRTHLMQPPYSILCDYRAHVYTHEAAGL
Cyberlindnera jadinii           VDTTALEQKVAKLAGKPAGLYCVSGTLSNQIAIRTHLFQPPYSILCDYRAHVYTHEAAGL
Torulaspora delbrueckii         MDTCFLENLVANLAGKEQGLFCVSGTLSNQIALRTHLLQPPYSVLCDYRAHVYTHEAAGL
Zygosaccharomyces bailii        IDTIRLEQTVAQLAGKEAGLFCVSGTLSNQIAVRTHLTQPPYSVLCDYRSHVYTHEAAGL
Schizosaccharomyces pombe       EDTRKLEVYVAKLTGKEAALFVTSGTQGNQLCIRSHLHQPPHSIICDDRAHIYNWEAGAI
Kluyveromyces lactis            VDTIELETVVARLAGKEAGLFCVSGTLSNQIGLRTHLFQPPYSILCDYRAHVYTHEAAGL
Pichia pastoris                 LDTLNLEEKVAQMADKEAGLFCVSGTLSNQIGLRSHLMQPPHRILCDSRAHVYMHEAGGL
                                 ** **  ::  .* . ** .:**  .*:  * ** :**:.::** **.* :**.*:
```

Figure 9

```
Saccharomyces cerevisiae        AILSQAMVVPVVPSNGDYLTLEDIKSHYVPDDGDIHGAPTRLLISLENTLHGIVYPLEELV
Saccharomyces_bayanus           AILSQAMVVPVVPSNGDYLTLEDIKSHYVPDDGDIHGAPTRLLISLENTLHGIVYPLEELV
Saccharomyces_kudriavzevii      AILSQAMVVPVIPSNGDYLTLEDIRSHYVPDDGDIHGAPTRLLISLENTLHGIVYPLEELV
Cyberlindnera_jadinii           AMLSNAMVVPVRPSNGDYLTLEDIKKNLVPEDGDIHGAPTKLISLENTLHGIVYPYEELL
Torulaspora_delbrueckii         AILSQAMVVPVRPANGNYLTLDDITAHYVPDDGDVHGAPTKVISLENTLHGMTPIDELV
Zygosaccharomyces_bailii        AILSQAMVVPVVPSNGNYMTLEDIKRHYVPDDGDIHGAPTRLVSLENTLHGIVYPLEELL
Schizosaccharomyces_pombe       GLFTQAIVRPISPKNNVYITAEEIENKLIL-GNDIHFSPTGLICLENTKGAVVPLDEVA
Kluyveromyces_lactis            AILSQAMVTPVIPSNGDYMTLEDIKAHYIPDDGDIHGAPTRVLSLENTLHGIVYPLEELI
Pichia_pastoris                 ATLSQAMVTPVTPRNGLYLTLEDVVDNYIPDDGDIHMAPTKVVSLENTHGIITPLEEIA
                                     ..: .*: :**  ::.  *   ** .:*: *****::: * .: **..:

Saccharomyces cerevisiae        RIKAWCMENGLKLHCDGARIWNAAAQSGVPLKQYGEIFDSISICLSKSMGAPIGSVLVGN
Saccharomyces_bayanus           RIKAWCMENGLKLHCDGARIWNAAAQSGVPLKQYGEIFDSISICLSKSMGAPIGSVLVGN
Saccharomyces_kudriavzevii      RIKAWCMENGLKLHCDGARIWNAAAQSGVPLKQYGEIFDSISICLSKSMGAPIGSVLVGN
Cyberlindnera_jadinii           RIKQFCVENGYKLHCDGARIWNASVETGVPLHKYGEIFDSISICLSKSIGAPMGSVLVGE
Torulaspora_delbrueckii         RIRAWCSQNNIKLHCDGARIWNAAIASGVPLKQFGELFDSISICLSKSMGAPIGSILVGD
Zygosaccharomyces_bailii        RIRIHCDIRIHCDGARLWNASVAAGVPMRQFGELFDSISICLSKSMGAPIGSVLVGD
Schizosaccharomyces_pombe       RISGLAKAHKIPLHCDGARLMDAAVASNVSIKEYCSYFDSVSLCLSKGLAAPVGSIIVGP
Kluyveromyces_lactis            RIKGWCLENDIKLHCDGARIWNAVVESGVSLKQYGEIFDSISICLSKSMGAPMGSVLVGS
Pichia_pastoris                 RISEWCRENDVRLHCDGARLWNASVETNTPLSEYGKLFDSISLCLSKSLGSPMGSVLVGD
                                **       . :*****:. .  .   .   *::**:*:****:.: . **::**
```

Figure 9 (continued)

| Species | Sequence |
|---|---|
| Saccharomyces cerevisiae | LKFVKKATHFRKQQGGGIRQSGMMARMALVNINNDWKSQLLYSHSLAHELAEYCEAKGIP |
| Saccharomyces bayanus | LKFVKKATHFRKQQGGGIRQSGMMARMALVNINNDWKSQLLYSHSLAHELAEYCEAKGIP |
| Saccharomyces kudriavzevii | LKFVKKATHFRKQQGGGIRQSGMMARMALVNINNDWKSQLLYSHSLAHELAQFCKAKGIP |
| Cyberlindnera jadinii | LPFIKKCNHFKKQCGGGIRQSGMMAKMAMVAIEDNLP-LLKSSHEKAKNLGDFCIENGIV |
| Torulaspora delbrueckii | AKFIKKANHFRKQQGGGIRQSGMMAKMATVAINGDWKAKMSYSHRLASDLALFCKENDIP |
| Zygosaccharomyces bailii | LKFIKKCNHFRKQQGGGIRQSGMMCAMALTTVTGDWKSKLLHSHQLAHELARFCIEKGIP |
| Schizosaccharomyces pombe | RDFIAKAKWFRKAYGGGLRQSGMLAAAGLYSIQHNFP-LLKQVHKYAIEVAEYAESLGIE |
| Kluyveromyces lactis | NKFVKKCNHFRKQQGGGVRQSGIMCRMALCAVNGDWKTKMGYSHQLAHELAKFCKDNGIP |
| Pichia pastoris | RKFIDKANHFKKQNGGGIRQSGFIARMASIAIDENLG-KLRQSHEYAKDVARFLQDNGVP |
|  | *::    *  :::::.***:**          .     :  :            |
| Saccharomyces cerevisiae | LESPADTNFVFINLKAARMDPPDVLVKKGLKYNVKLMGGRVSFHYQVTRDTLEKVKLAISE |
| Saccharomyces bayanus | LESPADTNFVFINLKAARMDPPDVLVKKGLKYNVKLMGGRVSFHYQVTRDTLEKVKLAISE |
| Saccharomyces kudriavzevii | LESPADTNFVFINLKSARMDPPDVLVKKGLKYNVKLMGGRVSFHYQITRDTLEKVKLAISE |
| Cyberlindnera jadinii | LESPVDTNFVFIDLEANYIKDDLIKFGKKHNVNLMGGRIAFHYQISDEALENVKLAVWD |
| Torulaspora delbrueckii | LESPTDTNFVFLDLSKAHMNPDVLVKKGLKYRIKLMGGRIAFHYQVTQETLEKAKCAILE |
| Zygosaccharomyces bailii | LESPADTNFVFISLSQAKMDPPDVLVKKGLKYGVKFEMGGRIAFHYQVNRDTLEKAKMAILE |
| Schizosaccharomyces pombe | LEVPTQSNMVTLA----NINVAILCDEAKKSGIILMGPRIVFHIQITPDAVEILKNVLRR |
| Kluyveromyces lactis | LESPADTNFVFLDLQKAKMNPDVLVKKGLKYGVKLMGGRVSFHYQVTRETLENVKSAVLE |
| Pichia pastoris | LECPTHTNFVFVDQKKARIDPDHLVAMGEKYNVNIMGTRFAFHFQNSKEAVERLKQAIME |
|  | ** *   *..:.:     .   :     ..  :**  . **.* .:    *  :     |

Figure 9 (continued)

```
Saccharomyces_cerevisiae      AFDYAKEHPFDCNGPTQIYRSESTE-VDVDGNAIREIKTYKY
Saccharomyces_bayanus         AFDYAKEHPFDCNGPTQIYRSESTE-VDVDGNAIREIKTYKY
Saccharomyces_kudriavzevii    AFDYAKEHPFDSNGPTKIYRSESTE-VDVDGNAIHEIKTYKY
Cyberlindnera_jadinii         AFENAKKNPYVHDGPYKMYRSPTPVKY--------------
Torulaspora_delbrueckii       SFEHAKEHPFNQQGQTKIYRSESTDKIDIDGNSIHGIKTYKY
Zygosaccharomyces_bailii      TFEYAKEHPFNSEGETKIYRSESTERVDIDGRPIHDIKTYKY
Schizosaccharomyces_pombe     TVERQAVETHIVAKPGEFCVGY-------------------
Kluyveromyces_lactis          TFQYAKENPFDTNGPTKIYRSESTD-FDIHGNPISDIKTYKY
Pichia_pastoris               TFKYSQEHPYVSTGAKRLYTSKSRSNSPVLKN---------
                               :  :             *    :
```

Figure 9 (continued)

SEQUENCE LISTING

```
<160> NUMBER OF SEQ ID NOS: 32

<210> SEQ ID NO 1
<211> LENGTH: 507
<212> TYPE: PRT
<213> ORGANISM: Saccharomyces cerevisiae

<400> SEQUENCE: 1

Met Thr Lys Ser Glu Gln Gln Ala Asp Ser Arg His Asn Val Ile Asp
1               5                   10                  15

Leu Val Gly Asn Thr Pro Leu Ile Ala Leu Lys Lys Leu Pro Lys Ala
            20                  25                  30

Leu Gly Ile Lys Pro Gln Ile Tyr Ala Lys Leu Glu Leu Tyr Asn Pro
        35                  40                  45

Gly Gly Ser Ile Lys Asp Arg Ile Ala Lys Ser Met Val Glu Glu Ala
    50                  55                  60

Glu Ala Ser Gly Arg Ile His Pro Ser Arg Ser Thr Leu Ile Glu Pro
65                  70                  75                  80

Thr Ser Gly Asn Thr Gly Ile Gly Leu Ala Leu Ile Gly Ala Ile Lys
                85                  90                  95

Gly Tyr Arg Thr Ile Ile Thr Leu Pro Glu Lys Met Ser Asn Glu Lys
            100                 105                 110

Val Ser Val Leu Lys Ala Leu Gly Ala Glu Ile Ile Arg Thr Pro Thr
        115                 120                 125

Ala Ala Ala Trp Asp Ser Pro Glu Ser His Ile Gly Val Ala Lys Lys
    130                 135                 140

Leu Glu Lys Glu Ile Pro Gly Ala Val Ile Leu Asp Gln Tyr Asn Asn
145                 150                 155                 160

Met Met Asn Pro Glu Ala His Tyr Phe Gly Thr Gly Arg Glu Ile Gln
                165                 170                 175

Arg Gln Leu Glu Asp Leu Asn Leu Phe Asp Asn Leu Arg Ala Val Val
            180                 185                 190

Ala Gly Ala Gly Thr Gly Gly Thr Ile Ser Gly Ile Ser Lys Tyr Leu
        195                 200                 205

Lys Glu Gln Asn Asp Lys Ile Gln Ile Val Gly Ala Asp Pro Phe Gly
    210                 215                 220

Ser Ile Leu Ala Gln Pro Glu Asn Leu Asn Lys Thr Asp Ile Thr Asp
225                 230                 235                 240

Tyr Lys Val Glu Gly Ile Gly Tyr Asp Phe Val Pro Gln Val Leu Asp
                245                 250                 255

Arg Lys Leu Ile Asp Val Trp Tyr Lys Thr Asp Asp Lys Pro Ser Phe
            260                 265                 270
```

```
Lys Tyr Ala Arg Gln Leu Ile Ser Asn Glu Gly Val Leu Val Gly Gly
            275                 280                 285

Ser Ser Gly Ser Ala Phe Thr Ala Val Val Lys Tyr Cys Glu Asp His
        290                 295                 300

Pro Glu Leu Thr Glu Asp Asp Val Ile Val Ala Ile Phe Pro Asp Ser
305                 310                 315                 320

Ile Arg Ser Tyr Leu Thr Lys Phe Val Asp Asp Glu Trp Leu Lys Lys
                325                 330                 335

Asn Asn Leu Trp Asp Asp Val Leu Ala Arg Phe Asp Ser Ser Lys
            340                 345                 350

Leu Glu Ala Ser Thr Thr Lys Tyr Ala Asp Val Phe Gly Asn Ala Thr
            355                 360                 365

Val Lys Asp Leu His Leu Lys Pro Val Val Ser Val Lys Glu Thr Ala
        370                 375                 380

Lys Val Thr Asp Val Ile Lys Ile Leu Lys Asp Asn Gly Phe Asp Gln
385                 390                 395                 400

Leu Pro Val Leu Thr Glu Asp Gly Lys Leu Ser Gly Leu Val Thr Leu
                405                 410                 415

Ser Glu Leu Leu Arg Lys Leu Ser Ile Asn Asn Ser Asn Asn Asp Asn
            420                 425                 430

Thr Ile Lys Gly Lys Tyr Leu Asp Phe Lys Lys Leu Asn Asn Phe Asn
            435                 440                 445

Asp Val Ser Ser Tyr Asn Glu Asn Lys Ser Gly Lys Lys Phe Ile
        450                 455                 460

Lys Phe Asp Glu Asn Ser Lys Leu Ser Asp Leu Asn Arg Phe Phe Glu
465                 470                 475                 480

Lys Asn Ser Ser Ala Val Ile Thr Asp Gly Leu Lys Pro Ile His Ile
                485                 490                 495

Val Thr Lys Met Asp Leu Leu Ser Tyr Leu Ala
            500                 505

<210> SEQ ID NO 2
<211> LENGTH: 353
<212> TYPE: PRT
<213> ORGANISM: Artificial Sequence
<220> FEATURE:
<223> OTHER INFORMATION: Mutated CYS4p

<400> SEQUENCE: 2

Met Thr Lys Ser Glu Gln Gln Ala Asp Ser Arg His Asn Val Ile Asp
1               5                   10                  15

Leu Val Gly Asn Thr Pro Leu Ile Ala Leu Lys Lys Leu Pro Lys Ala
            20                  25                  30

Leu Gly Ile Lys Pro Gln Ile Tyr Ala Lys Leu Glu Leu Tyr Asn Pro
        35                  40                  45

Gly Gly Ser Ile Lys Asp Arg Ile Ala Lys Ser Met Val Glu Glu Ala
    50                  55                  60

Glu Ala Ser Gly Arg Ile His Pro Ser Arg Ser Thr Leu Ile Glu Pro
65                  70                  75                  80

Thr Ser Gly Asn Thr Gly Ile Gly Leu Ala Leu Ile Gly Ala Ile Lys
                85                  90                  95

Gly Tyr Arg Thr Ile Ile Thr Leu Pro Glu Lys Met Ser Asn Glu Lys
            100                 105                 110

Val Ser Val Leu Lys Ala Leu Gly Ala Glu Ile Ile Arg Thr Pro Thr
        115                 120                 125
```

```
Ala Ala Ala Trp Asp Ser Pro Glu Ser His Ile Gly Val Ala Lys Lys
        130                 135                 140

Leu Glu Lys Glu Ile Pro Gly Ala Val Ile Leu Asp Gln Tyr Asn Asn
145                 150                 155                 160

Met Met Asn Pro Glu Ala His Tyr Phe Gly Thr Gly Arg Glu Ile Gln
                165                 170                 175

Arg Gln Leu Glu Asp Leu Asn Leu Phe Asp Asn Leu Arg Ala Val Val
        180                 185                 190

Ala Gly Ala Gly Thr Gly Gly Thr Ile Ser Gly Ile Ser Lys Tyr Leu
        195                 200                 205

Lys Glu Gln Asn Asp Lys Ile Gln Ile Val Gly Ala Asp Pro Phe Gly
210                 215                 220

Ser Ile Leu Ala Gln Pro Glu Asn Leu Asn Lys Thr Asp Ile Thr Asp
225                 230                 235                 240

Tyr Lys Val Glu Gly Ile Gly Tyr Asp Phe Val Pro Gln Val Leu Asp
                245                 250                 255

Arg Lys Leu Ile Asp Val Trp Tyr Lys Thr Asp Lys Pro Ser Phe
        260                 265                 270

Lys Tyr Ala Arg Gln Leu Ile Ser Asn Glu Gly Val Leu Val Gly Gly
        275                 280                 285

Ser Ser Gly Ser Ala Phe Thr Ala Val Val Lys Tyr Cys Glu Asp His
        290                 295                 300

Pro Glu Leu Thr Glu Asp Asp Val Ile Val Ala Ile Phe Pro Asp Ser
305                 310                 315                 320

Ile Arg Ser Tyr Leu Thr Lys Phe Val Asp Asp Glu Trp Leu Lys Lys
                325                 330                 335

Asn Asn Leu Trp Asp Asp Asp Val Leu Ala Arg Phe Asp Ser Ser Lys
        340                 345                 350

Leu

<210> SEQ ID NO 3
<211> LENGTH: 656
<212> TYPE: PRT
<213> ORGANISM: Saccharomyces cerevisiae

<400> SEQUENCE: 3

Met Ser Val Ser Thr Ala Lys Arg Ser Leu Asp Val Val Ser Pro Gly
1               5                   10                  15

Ser Leu Ala Glu Phe Glu Gly Ser Lys Ser Arg His Asp Glu Ile Glu
                20                  25                  30

Asn Glu His Arg Arg Thr Gly Thr Arg Asp Gly Glu Asp Ser Glu Gln
        35                  40                  45

Pro Lys Lys Lys Gly Ser Lys Thr Ser Lys Lys Gln Asp Leu Asp Pro
    50                  55                  60

Glu Thr Lys Gln Lys Arg Thr Ala Gln Asn Arg Ala Ala Gln Arg Ala
65                  70                  75                  80

Phe Arg Glu Arg Lys Glu Arg Lys Met Lys Glu Leu Glu Lys Lys Val
                85                  90                  95

Gln Ser Leu Glu Ser Ile Gln Gln Gln Asn Glu Val Glu Ala Thr Phe
            100                 105                 110

Leu Arg Asp Gln Leu Ile Thr Leu Val Asn Glu Leu Lys Lys Tyr Arg
        115                 120                 125

Pro Glu Thr Arg Asn Asp Ser Lys Val Leu Glu Tyr Leu Ala Arg Arg
    130                 135                 140
```

```
Asp Pro Asn Leu Leu Phe Ser Lys Asn Asn Val His Ser Asn Ser
145                 150                 155                 160

Glu Pro Ile Asp Thr Pro Asn Asp Ile Gln Glu Asn Val Lys Gln
            165                 170                 175

Lys Met Asn Phe Thr Phe Gln Tyr Pro Leu Asp Asn Asp Asp Asn
            180                 185                 190

Asp Asp Ser Lys Asn Val Gly Lys Gln Leu Pro Ser Pro Asn Asp Pro
        195                 200                 205

Ser His Ser Ala Pro Met Pro Ile Asn Gln Thr Gln Lys Lys Leu Ser
    210                 215                 220

Asp Ala Thr Asp Ser Ser Ser Ala Thr Leu Asp Ser Leu Ser Asn Ser
225                 230                 235                 240

Asn Asp Val Leu Asn Asn Thr Pro Asn Ser Ser Thr Ser Met Asp Trp
                245                 250                 255

Leu Asp Asn Val Ile Tyr Thr Asn Arg Phe Val Ser Gly Asp Asp Gly
                260                 265                 270

Ser Asn Ser Lys Thr Lys Asn Leu Asp Ser Asn Met Phe Ser Asn Asp
        275                 280                 285

Phe Asn Phe Glu Asn Gln Phe Asp Glu Gln Val Ser Glu Phe Cys Ser
    290                 295                 300

Lys Met Asn Gln Val Cys Gly Thr Arg Gln Cys Pro Ile Pro Lys Lys
305                 310                 315                 320

Pro Ile Ser Ala Leu Asp Lys Glu Val Phe Ala Ser Ser Ile Leu
                325                 330                 335

Ser Ser Asn Ser Pro Ala Leu Thr Asn Thr Trp Glu Ser His Ser Asn
                340                 345                 350

Ile Thr Asp Asn Thr Pro Ala Asn Val Ile Ala Thr Asp Ala Thr Lys
                355                 360                 365

Tyr Glu Asn Ser Phe Ser Gly Phe Gly Arg Leu Gly Phe Asp Met Ser
    370                 375                 380

Ala Asn His Tyr Val Val Asn Asp Asn Ser Thr Gly Ser Thr Asp Ser
385                 390                 395                 400

Thr Asp Ser Thr Gly Ser Thr Gly Ser Thr Gly Asn Lys Asn Lys Lys
                405                 410                 415

Asn Asn Asn Asn Ser Asp Asp Val Leu Pro Phe Ile Ser Glu Ser Pro
                420                 425                 430

Phe Asp Met Asn Gln Val Thr Asn Phe Phe Ser Pro Gly Ser Thr Gly
            435                 440                 445

Ile Gly Asn Asn Ala Ala Ser Asn Thr Asn Pro Ser Leu Leu Gln Ser
    450                 455                 460

Ser Lys Glu Asp Ile Pro Phe Ile Asn Ala Asn Leu Ala Phe Pro Asp
465                 470                 475                 480

Asp Asn Ser Thr Asn Ile Gln Leu Gln Pro Phe Ser Glu Ser Gln Ser
                485                 490                 495

Gln Asn Lys Phe Asp Tyr Asp Met Phe Phe Arg Asp Ser Ser Lys Glu
            500                 505                 510

Gly Asn Asn Leu Phe Gly Glu Phe Leu Glu Asp Asp Asp Asp Lys
    515                 520                 525

Lys Ala Ala Asn Met Ser Asp Asp Glu Ser Ser Leu Ile Lys Asn Gln
530                 535                 540

Leu Ile Asn Glu Glu Pro Glu Leu Pro Lys Gln Tyr Leu Gln Ser Val
545                 550                 555                 560
```

```
Pro Gly Asn Glu Ser Glu Ile Ser Gln Lys Asn Gly Ser Ser Leu Gln
                565                 570                 575

Asn Ala Asp Lys Ile Asn Asn Gly Asn Asp Asn Asp Asp Asn Asp
            580                 585                 590

Val Val Pro Ser Lys Glu Gly Ser Leu Leu Arg Cys Ser Glu Ile Trp
        595                 600                 605

Asp Arg Ile Thr Thr His Pro Lys Tyr Ser Asp Ile Asp Val Asp Gly
    610                 615                 620

Leu Cys Ser Glu Leu Met Ala Lys Ala Lys Cys Ser Glu Arg Gly Val
625                 630                 635                 640

Val Ile Asn Ala Glu Asp Val Gln Leu Ala Leu Asn Lys His Met Asn
                645                 650                 655

<210> SEQ ID NO 4
<211> LENGTH: 656
<212> TYPE: PRT
<213> ORGANISM: Artificial Sequence
<220> FEATURE:
<223> OTHER INFORMATION: Mutated YAP1p
<220> FEATURE:
<221> NAME/KEY: VARIANT
<222> LOCATION: (626)..(626)
<223> OTHER INFORMATION: Xaa can be Asp, Leu, Arg, His, Glu, Ser, Thr,
      Asn, Gln, Lys, Ser, Tyr, Met or Trp

<400> SEQUENCE: 4

Met Ser Val Ser Thr Ala Lys Arg Ser Leu Asp Val Val Ser Pro Gly
1               5                   10                  15

Ser Leu Ala Glu Phe Glu Gly Ser Lys Ser Arg His Asp Glu Ile Glu
            20                  25                  30

Asn Glu His Arg Arg Thr Gly Thr Arg Asp Gly Glu Asp Ser Glu Gln
        35                  40                  45

Pro Lys Lys Lys Gly Ser Lys Thr Ser Lys Lys Gln Asp Leu Asp Pro
    50                  55                  60

Glu Thr Lys Gln Lys Arg Thr Ala Gln Asn Arg Ala Ala Gln Arg Ala
65                  70                  75                  80

Phe Arg Glu Arg Lys Glu Arg Lys Met Lys Glu Leu Glu Lys Lys Val
                85                  90                  95

Gln Ser Leu Glu Ser Ile Gln Gln Asn Glu Val Glu Ala Thr Phe
            100                 105                 110

Leu Arg Asp Gln Leu Ile Thr Leu Val Asn Glu Leu Lys Lys Tyr Arg
        115                 120                 125

Pro Glu Thr Arg Asn Asp Ser Lys Val Leu Glu Tyr Leu Ala Arg Arg
    130                 135                 140

Asp Pro Asn Leu Leu Phe Ser Lys Asn Asn Val Asn His Ser Asn Ser
145                 150                 155                 160

Glu Pro Ile Asp Thr Pro Asn Asp Ile Gln Glu Asn Val Lys Gln
                165                 170                 175

Lys Met Asn Phe Thr Phe Gln Tyr Pro Leu Asp Asn Asp Asn Asp Asn
            180                 185                 190

Asp Asp Ser Lys Asn Val Gly Lys Gln Leu Pro Ser Pro Asn Asp Pro
        195                 200                 205

Ser His Ser Ala Pro Met Pro Ile Asn Gln Thr Gln Lys Lys Leu Ser
    210                 215                 220

Asp Ala Thr Asp Ser Ser Ser Ala Thr Leu Asp Ser Leu Ser Asn Ser
225                 230                 235                 240
```

```
Asn Asp Val Leu Asn Asn Thr Pro Asn Ser Ser Thr Ser Met Asp Trp
            245                 250                 255
Leu Asp Asn Val Ile Tyr Thr Asn Arg Phe Val Ser Gly Asp Asp Gly
        260                 265                 270
Ser Asn Ser Lys Thr Lys Asn Leu Asp Ser Asn Met Phe Ser Asn Asp
    275                 280                 285
Phe Asn Phe Glu Asn Gln Phe Asp Glu Gln Val Ser Glu Phe Cys Ser
290                 295                 300
Lys Met Asn Gln Val Cys Gly Thr Arg Gln Cys Pro Ile Pro Lys Lys
305                 310                 315                 320
Pro Ile Ser Ala Leu Asp Lys Glu Val Phe Ala Ser Ser Ser Ile Leu
                325                 330                 335
Ser Ser Asn Ser Pro Ala Leu Thr Asn Thr Trp Glu Ser His Ser Asn
            340                 345                 350
Ile Thr Asp Asn Thr Pro Ala Asn Val Ile Ala Thr Asp Ala Thr Lys
        355                 360                 365
Tyr Glu Asn Ser Phe Ser Gly Phe Gly Arg Leu Gly Phe Asp Met Ser
    370                 375                 380
Ala Asn His Tyr Val Val Asn Asp Asn Ser Thr Gly Ser Thr Asp Ser
385                 390                 395                 400
Thr Asp Ser Thr Gly Ser Thr Gly Ser Thr Gly Asn Lys Asn Lys Lys
                405                 410                 415
Asn Asn Asn Ser Asp Asp Val Leu Pro Phe Ile Ser Glu Ser Pro
            420                 425                 430
Phe Asp Met Asn Gln Val Thr Asn Phe Phe Ser Pro Gly Ser Thr Gly
        435                 440                 445
Ile Gly Asn Asn Ala Ala Ser Asn Thr Asn Pro Ser Leu Leu Gln Ser
    450                 455                 460
Ser Lys Glu Asp Ile Pro Phe Ile Asn Ala Asn Leu Ala Phe Pro Asp
465                 470                 475                 480
Asp Asn Ser Thr Asn Ile Gln Leu Gln Pro Phe Ser Glu Ser Gln Ser
                485                 490                 495
Gln Asn Lys Phe Asp Tyr Asp Met Phe Phe Arg Asp Ser Ser Lys Glu
            500                 505                 510
Gly Asn Asn Leu Phe Gly Glu Phe Leu Glu Asp Asp Asp Asp Asp Lys
        515                 520                 525
Lys Ala Ala Asn Met Ser Asp Asp Glu Ser Ser Leu Ile Lys Asn Gln
    530                 535                 540
Leu Ile Asn Glu Glu Pro Glu Leu Pro Lys Gln Tyr Leu Gln Ser Val
545                 550                 555                 560
Pro Gly Asn Glu Ser Glu Ile Ser Gln Lys Asn Gly Ser Ser Leu Gln
                565                 570                 575
Asn Ala Asp Lys Ile Asn Asn Gly Asn Asp Asn Asp Asn Asn Asp
            580                 585                 590
Val Val Pro Ser Lys Glu Gly Ser Leu Leu Arg Cys Ser Glu Ile Trp
        595                 600                 605
Asp Arg Ile Thr Thr His Pro Lys Tyr Ser Asp Ile Asp Val Asp Gly
    610                 615                 620
Leu Xaa Ser Glu Leu Met Ala Lys Ala Lys Cys Ser Glu Arg Gly Val
625                 630                 635                 640
Val Ile Asn Ala Glu Asp Val Gln Leu Ala Leu Asn Lys His Met Asn
                645                 650                 655
```

<210> SEQ ID NO 5
<211> LENGTH: 656
<212> TYPE: PRT
<213> ORGANISM: Artificial Sequence
<220> FEATURE:
<223> OTHER INFORMATION: Mutated YAP1p

<400> SEQUENCE: 5

```
Met Ser Val Ser Thr Ala Lys Arg Ser Leu Asp Val Val Ser Pro Gly
1               5                   10                  15

Ser Leu Ala Glu Phe Glu Gly Ser Lys Ser Arg His Asp Glu Ile Glu
            20                  25                  30

Asn Glu His Arg Arg Thr Gly Thr Arg Asp Gly Glu Asp Ser Glu Gln
        35                  40                  45

Pro Lys Lys Lys Gly Ser Lys Thr Ser Lys Lys Gln Asp Leu Asp Pro
    50                  55                  60

Glu Thr Lys Gln Lys Arg Thr Ala Gln Asn Arg Ala Ala Gln Arg Ala
65                  70                  75                  80

Phe Arg Glu Arg Lys Glu Arg Lys Met Lys Glu Leu Glu Lys Lys Val
                85                  90                  95

Gln Ser Leu Glu Ser Ile Gln Gln Asn Glu Val Glu Ala Thr Phe
            100                 105                 110

Leu Arg Asp Gln Leu Ile Thr Leu Val Asn Glu Leu Lys Lys Tyr Arg
            115                 120                 125

Pro Glu Thr Arg Asn Asp Ser Lys Val Leu Glu Tyr Leu Ala Arg Arg
    130                 135                 140

Asp Pro Asn Leu Leu Phe Ser Lys Asn Val Asn His Ser Asn Ser
145                 150                 155                 160

Glu Pro Ile Asp Thr Pro Asn Asp Ile Gln Glu Asn Val Lys Gln
                165                 170                 175

Lys Met Asn Phe Thr Phe Gln Tyr Pro Leu Asp Asn Asp Asn Asp Asn
            180                 185                 190

Asp Asp Ser Lys Asn Val Gly Lys Gln Leu Pro Ser Pro Asn Asp Pro
    195                 200                 205

Ser His Ser Ala Pro Met Pro Ile Asn Gln Thr Gln Lys Lys Leu Ser
    210                 215                 220

Asp Ala Thr Asp Ser Ser Ser Ala Thr Leu Asp Ser Leu Ser Asn Ser
225                 230                 235                 240

Asn Asp Val Leu Asn Asn Thr Pro Asn Ser Ser Thr Ser Met Asp Trp
                245                 250                 255

Leu Asp Asn Val Ile Tyr Thr Asn Arg Phe Val Ser Gly Asp Asp Gly
            260                 265                 270

Ser Asn Ser Lys Thr Lys Asn Leu Asp Ser Asn Met Phe Ser Asn Asp
    275                 280                 285

Phe Asn Phe Glu Asn Gln Phe Asp Glu Gln Val Ser Glu Phe Cys Ser
    290                 295                 300

Lys Met Asn Gln Val Cys Gly Thr Arg Gln Cys Pro Ile Pro Lys Lys
305                 310                 315                 320

Pro Ile Ser Ala Leu Asp Lys Glu Val Phe Ala Ser Ser Ile Leu
                325                 330                 335

Ser Ser Asn Ser Pro Ala Leu Thr Asn Thr Trp Glu Ser His Ser Asn
            340                 345                 350

Ile Thr Asp Asn Thr Pro Ala Asn Val Ile Ala Thr Asp Ala Thr Lys
    355                 360                 365
```

```
Tyr Glu Asn Ser Phe Ser Gly Phe Gly Arg Leu Gly Phe Asp Met Ser
        370                 375                 380
Ala Asn His Tyr Val Val Asn Asp Asn Ser Thr Gly Ser Thr Asp Ser
385                 390                 395                 400
Thr Asp Ser Thr Gly Ser Thr Gly Ser Thr Gly Asn Lys Asn Lys Lys
                405                 410                 415
Asn Asn Asn Asn Ser Asp Asp Val Leu Pro Phe Ile Ser Glu Ser Pro
                420                 425                 430
Phe Asp Met Asn Gln Val Thr Asn Phe Phe Ser Pro Gly Ser Thr Gly
            435                 440                 445
Ile Gly Asn Asn Ala Ala Ser Asn Thr Asn Pro Ser Leu Leu Gln Ser
        450                 455                 460
Ser Lys Glu Asp Ile Pro Phe Ile Asn Ala Asn Leu Ala Phe Pro Asp
465                 470                 475                 480
Asp Asn Ser Thr Asn Ile Gln Leu Gln Pro Phe Ser Glu Ser Gln Ser
                485                 490                 495
Gln Asn Lys Phe Asp Tyr Asp Met Phe Phe Arg Asp Ser Lys Glu
            500                 505                 510
Gly Asn Asn Leu Phe Gly Glu Phe Leu Glu Asp Asp Asp Asp Lys
        515                 520                 525
Lys Ala Ala Asn Met Ser Asp Asp Glu Ser Ser Leu Ile Lys Asn Gln
530                 535                 540
Leu Ile Asn Glu Glu Pro Glu Leu Pro Lys Gln Tyr Leu Gln Ser Val
545                 550                 555                 560
Pro Gly Asn Glu Ser Glu Ile Ser Gln Lys Asn Gly Ser Ser Leu Gln
                565                 570                 575
Asn Ala Asp Lys Ile Asn Asn Gly Asn Asp Asn Asp Asn Asp Asn Asp
            580                 585                 590
Val Val Pro Ser Lys Glu Gly Ser Leu Leu Arg Cys Ser Glu Ile Trp
        595                 600                 605
Asp Arg Ile Thr Thr His Pro Lys Tyr Ser Asp Ile Asp Val Asp Gly
            610                 615                 620
Leu Asp Ser Glu Leu Met Ala Lys Ala Lys Cys Ser Glu Arg Gly Val
625                 630                 635                 640
Val Ile Asn Ala Glu Asp Val Gln Leu Ala Leu Asn Lys His Met Asn
                645                 650                 655

<210> SEQ ID NO 6
<211> LENGTH: 507
<212> TYPE: PRT
<213> ORGANISM: Saccharomyces cerevisiae

<400> SEQUENCE: 6

Met Thr Lys Ser Glu Gln Gln Ala Asp Ser Arg His Asn Val Ile Asp
1               5                   10                  15
Leu Val Gly Asn Thr Pro Leu Ile Ala Leu Lys Lys Leu Pro Lys Ala
            20                  25                  30
Leu Gly Ile Lys Pro Gln Ile Tyr Ala Lys Leu Glu Leu Tyr Asn Pro
        35                  40                  45
Gly Gly Ser Ile Lys Asp Arg Ile Ala Lys Ser Met Val Glu Glu Ala
    50                  55                  60
Glu Ala Ser Gly Arg Ile His Pro Ser Arg Ser Thr Leu Ile Glu Pro
65                  70                  75                  80
Thr Ser Gly Asn Thr Gly Ile Gly Leu Ala Leu Ile Gly Ala Ile Lys
                85                  90                  95
```

-continued

```
Gly Tyr Arg Thr Ile Ile Thr Leu Pro Glu Lys Met Ser Asn Glu Lys
                100                 105                 110

Val Ser Val Leu Lys Ala Leu Gly Ala Glu Ile Ile Arg Thr Pro Thr
            115                 120                 125

Ala Ala Ala Trp Asp Ser Pro Glu Ser His Ile Gly Val Ala Lys Lys
        130                 135                 140

Leu Glu Lys Glu Ile Pro Gly Ala Val Ile Leu Asp Gln Tyr Asn Asn
145                 150                 155                 160

Met Met Asn Pro Glu Ala His Tyr Phe Gly Thr Gly Arg Glu Ile Gln
                165                 170                 175

Arg Gln Leu Glu Asp Leu Asn Leu Phe Asp Asn Leu Arg Ala Val Val
            180                 185                 190

Ala Gly Ala Gly Thr Gly Gly Thr Ile Ser Gly Ile Ser Lys Tyr Leu
        195                 200                 205

Lys Glu Gln Asn Asp Lys Ile Gln Ile Val Gly Ala Asp Pro Phe Gly
    210                 215                 220

Ser Ile Leu Ala Gln Pro Glu Asn Leu Asn Lys Thr Asp Ile Thr Asp
225                 230                 235                 240

Tyr Lys Val Glu Gly Ile Gly Tyr Asp Phe Val Pro Gln Val Leu Asp
                245                 250                 255

Arg Lys Leu Ile Asp Val Trp Tyr Lys Thr Asp Asp Lys Pro Ser Phe
            260                 265                 270

Lys Tyr Ala Arg Gln Leu Ile Ser Asn Glu Gly Val Leu Val Gly Gly
        275                 280                 285

Ser Ser Gly Ser Ala Phe Thr Ala Val Val Lys Tyr Cys Glu Asp His
    290                 295                 300

Pro Glu Leu Thr Glu Asp Val Ile Val Ala Ile Phe Pro Asp Ser
305                 310                 315                 320

Ile Arg Ser Tyr Leu Thr Lys Phe Val Asp Asp Glu Trp Leu Lys Lys
                325                 330                 335

Asn Asn Leu Trp Asp Asp Val Leu Ala Arg Phe Asp Ser Ser Lys
            340                 345                 350

Leu Glu Ala Ser Thr Thr Lys Tyr Ala Asp Val Phe Gly Asn Ala Thr
        355                 360                 365

Val Lys Asp Leu His Leu Lys Pro Val Val Ser Val Lys Glu Thr Ala
    370                 375                 380

Lys Val Thr Asp Val Ile Lys Ile Leu Lys Asp Asn Gly Phe Asp Gln
385                 390                 395                 400

Leu Pro Val Leu Thr Glu Asp Gly Lys Leu Ser Gly Leu Val Thr Leu
                405                 410                 415

Ser Glu Leu Leu Arg Lys Leu Ser Ile Asn Asn Ser Asn Asn Asp Asn
            420                 425                 430

Thr Ile Lys Gly Lys Tyr Leu Asp Phe Lys Lys Leu Asn Asn Phe Asn
        435                 440                 445

Asp Val Ser Ser Tyr Asn Glu Asn Lys Ser Gly Lys Lys Lys Phe Ile
    450                 455                 460

Lys Phe Asp Glu Asn Ser Lys Leu Ser Asp Leu Asn Arg Phe Phe Glu
465                 470                 475                 480

Lys Asn Ser Ser Ala Val Ile Thr Asp Gly Leu Lys Pro Ile His Ile
                485                 490                 495

Val Thr Lys Met Asp Leu Leu Ser Tyr Leu Ala
            500                 505
```

<210> SEQ ID NO 7
<211> LENGTH: 656
<212> TYPE: PRT
<213> ORGANISM: Saccharomyces cerevisiae

<400> SEQUENCE: 7

| | | | | | | | | | | | | | | | |
|---|---|---|---|---|---|---|---|---|---|---|---|---|---|---|---|
| Met | Ser | Val | Ser | Thr | Ala | Lys | Arg | Ser | Leu | Asp | Val | Ser | Pro | Gly | |
| 1 | | | | 5 | | | | | 10 | | | | | 15 | |
| Ser | Leu | Ala | Glu | Phe | Glu | Gly | Ser | Lys | Ser | Arg | His | Asp | Glu | Ile | Glu |
| | | | 20 | | | | | 25 | | | | | 30 | | |
| Asn | Glu | His | Arg | Arg | Thr | Gly | Thr | Arg | Asp | Gly | Glu | Asp | Ser | Glu | Gln |
| | | | 35 | | | | | 40 | | | | | 45 | | |
| Pro | Lys | Lys | Lys | Gly | Ser | Lys | Thr | Ser | Lys | Lys | Gln | Asp | Leu | Asp | Pro |
| | 50 | | | | | 55 | | | | | 60 | | | | |
| Glu | Thr | Lys | Gln | Lys | Arg | Thr | Ala | Gln | Asn | Arg | Ala | Ala | Gln | Arg | Ala |
| 65 | | | | | 70 | | | | | 75 | | | | | 80 |
| Phe | Arg | Glu | Arg | Lys | Glu | Arg | Lys | Met | Lys | Glu | Leu | Glu | Lys | Lys | Val |
| | | | | 85 | | | | | 90 | | | | | 95 | |
| Gln | Ser | Leu | Glu | Ser | Ile | Gln | Gln | Asn | Glu | Val | Glu | Ala | Thr | Phe | |
| | | | 100 | | | | | 105 | | | | | 110 | | |
| Leu | Arg | Asp | Gln | Leu | Ile | Thr | Leu | Val | Asn | Glu | Leu | Lys | Lys | Tyr | Arg |
| | | | 115 | | | | | 120 | | | | | 125 | | |
| Pro | Glu | Thr | Arg | Asn | Asp | Ser | Lys | Val | Leu | Glu | Tyr | Leu | Ala | Arg | Arg |
| | 130 | | | | | 135 | | | | | 140 | | | | |
| Asp | Pro | Asn | Leu | Leu | Phe | Ser | Lys | Asn | Val | Asn | His | Ser | Asn | Ser | |
| 145 | | | | | 150 | | | | | 155 | | | | | 160 |
| Glu | Pro | Ile | Asp | Thr | Pro | Asn | Asp | Ile | Gln | Glu | Asn | Val | Lys | Gln | |
| | | | | 165 | | | | | 170 | | | | | 175 | |
| Lys | Met | Asn | Phe | Thr | Phe | Gln | Tyr | Pro | Leu | Asp | Asn | Asp | Asn | Asp | Asn |
| | | | 180 | | | | | 185 | | | | | 190 | | |
| Asp | Asp | Ser | Lys | Asn | Val | Gly | Lys | Gln | Leu | Pro | Ser | Pro | Asn | Asp | Pro |
| | | | 195 | | | | | 200 | | | | | 205 | | |
| Ser | His | Ser | Ala | Pro | Met | Pro | Ile | Asn | Gln | Thr | Gln | Lys | Lys | Leu | Ser |
| | 210 | | | | | 215 | | | | | 220 | | | | |
| Asp | Ala | Thr | Asp | Ser | Ser | Ser | Ala | Thr | Leu | Asp | Ser | Leu | Ser | Asn | Ser |
| 225 | | | | | 230 | | | | | 235 | | | | | 240 |
| Asn | Asp | Val | Leu | Asn | Asn | Thr | Pro | Asn | Ser | Ser | Thr | Ser | Met | Asp | Trp |
| | | | | 245 | | | | | 250 | | | | | 255 | |
| Leu | Asp | Asn | Val | Ile | Tyr | Thr | Asn | Arg | Phe | Val | Ser | Gly | Asp | Asp | Gly |
| | | | 260 | | | | | 265 | | | | | 270 | | |
| Ser | Asn | Ser | Lys | Thr | Lys | Asn | Leu | Asp | Ser | Asn | Met | Phe | Ser | Asn | Asp |
| | | | 275 | | | | | 280 | | | | | 285 | | |
| Phe | Asn | Phe | Glu | Asn | Gln | Phe | Asp | Glu | Gln | Val | Ser | Glu | Phe | Cys | Ser |
| | 290 | | | | | 295 | | | | | 300 | | | | |
| Lys | Met | Asn | Gln | Val | Cys | Gly | Thr | Arg | Gln | Cys | Pro | Ile | Pro | Lys | Lys |
| 305 | | | | | 310 | | | | | 315 | | | | | 320 |
| Pro | Ile | Ser | Ala | Leu | Asp | Lys | Glu | Val | Phe | Ala | Ser | Ser | Ile | Leu | |
| | | | | 325 | | | | | 330 | | | | | 335 | |
| Ser | Ser | Asn | Ser | Pro | Ala | Leu | Thr | Asn | Thr | Trp | Glu | Ser | His | Ser | Asn |
| | | | 340 | | | | | 345 | | | | | 350 | | |
| Ile | Thr | Asp | Asn | Thr | Pro | Ala | Asn | Val | Ile | Ala | Thr | Asp | Ala | Thr | Lys |
| | | | 355 | | | | | 360 | | | | | 365 | | |
| Tyr | Glu | Asn | Ser | Phe | Ser | Gly | Phe | Gly | Arg | Leu | Gly | Phe | Asp | Met | Ser |
| | 370 | | | | | 375 | | | | | 380 | | | | |

Ala Asn His Tyr Val Val Asn Asp Asn Ser Thr Gly Ser Thr Asp Ser
385                 390                 395                 400

Thr Asp Ser Thr Gly Ser Thr Gly Ser Thr Gly Asn Lys Asn Lys Lys
            405                 410                 415

Asn Asn Asn Asn Ser Asp Asp Val Leu Pro Phe Ile Ser Glu Ser Pro
        420                 425                 430

Phe Asp Met Asn Gln Val Thr Asn Phe Phe Ser Pro Gly Ser Thr Gly
        435                 440                 445

Ile Gly Asn Asn Ala Ala Ser Asn Thr Asn Pro Ser Leu Leu Gln Ser
    450                 455                 460

Ser Lys Glu Asp Ile Pro Phe Ile Asn Ala Asn Leu Ala Phe Pro Asp
465                 470                 475                 480

Asp Asn Ser Thr Asn Ile Gln Leu Gln Pro Phe Ser Glu Ser Gln Ser
            485                 490                 495

Gln Asn Lys Phe Asp Tyr Asp Met Phe Phe Arg Asp Ser Ser Lys Glu
        500                 505                 510

Gly Asn Asn Leu Phe Gly Glu Phe Leu Glu Asp Asp Asp Asp Asp Lys
    515                 520                 525

Lys Ala Ala Asn Met Ser Asp Asp Glu Ser Ser Leu Ile Lys Asn Gln
530                 535                 540

Leu Ile Asn Glu Glu Pro Glu Leu Pro Lys Gln Tyr Leu Gln Ser Val
545                 550                 555                 560

Pro Gly Asn Glu Ser Glu Ile Ser Gln Lys Asn Gly Ser Ser Leu Gln
            565                 570                 575

Asn Ala Asp Lys Ile Asn Asn Gly Asn Asp Asn Asp Asn Asp Asn Asp
        580                 585                 590

Val Val Pro Ser Lys Glu Gly Ser Leu Leu Arg Cys Ser Glu Ile Trp
    595                 600                 605

Asp Arg Ile Thr Thr His Pro Lys Tyr Ser Asp Ile Asp Val Asp Gly
610                 615                 620

Leu Cys Ser Glu Leu Met Ala Lys Ala Lys Cys Ser Glu Arg Gly Val
625                 630                 635                 640

Val Ile Asn Ala Glu Asp Val Gln Leu Ala Leu Asn Lys His Met Asn
            645                 650                 655

<210> SEQ ID NO 8
<211> LENGTH: 419
<212> TYPE: PRT
<213> ORGANISM: Saccharomyces bayanus

<400> SEQUENCE: 8

Met Thr Lys Ser Glu Gln Gln Thr Asp Ser Arg His Asp Val Ile Asp
1               5                   10                  15

Leu Val Gly Asn Thr Pro Leu Ile Ala Leu Lys Lys Leu Pro Lys Ala
                20                  25                  30

Leu Gly Ile Arg Pro Gln Ile Tyr Ala Lys Leu Glu Ile Tyr Asn Pro
            35                  40                  45

Gly Gly Ser Ile Lys Asp Arg Ile Ala Lys Ser Met Val Glu Glu Ala
        50                  55                  60

Glu Ala Ser Gly Arg Ile His Pro Ser Arg Ser Thr Leu Ile Glu Pro
65                  70                  75                  80

Thr Ser Gly Asn Thr Gly Ile Gly Leu Ala Leu Val Gly Ala Ile Lys
                85                  90                  95

Gly Tyr Arg Thr Ile Ile Thr Leu Pro Glu Lys Met Ser Asn Glu Lys
            100                 105                 110

Val Ser Val Leu Lys Ala Leu Gly Ala Glu Ile Ile Arg Thr Pro Thr
            115                 120                 125

Ala Ala Ala Trp Asp Ser Pro Glu Ser His Ile Gly Val Ala Lys Lys
130                 135                 140

Leu Glu Lys Glu Ile Pro Gly Ala Val Ile Leu Asp Gln Tyr Asn Asn
145                 150                 155                 160

Pro Met Asn Pro Glu Ala His Tyr Phe Gly Thr Gly Arg Glu Ile Gln
                165                 170                 175

Arg Gln Leu Gln Asp Leu Asn Leu Phe Asp Asn Leu Arg Ala Val Val
            180                 185                 190

Ala Gly Ala Gly Thr Gly Gly Thr Ile Thr Gly Ile Ala Lys Tyr Ile
            195                 200                 205

Lys Glu Gln Asn Glu Lys Ile Gln Ile Val Gly Ala Asp Pro Leu Gly
210                 215                 220

Ser Ile Leu Ala Val Pro Glu Asn Leu Asn Lys Thr Asp Val Thr Asp
225                 230                 235                 240

Tyr Lys Val Glu Gly Ile Gly Tyr Asp Phe Ile Pro Asp Val Leu Asn
                245                 250                 255

Arg Asp Leu Ile Asp Val Trp Tyr Lys Thr Asp Asp Lys Pro Ser Phe
            260                 265                 270

Lys Tyr Ala Arg Gln Leu Ile Ser Asn Glu Gly Val Leu Val Gly Gly
            275                 280                 285

Ser Ser Gly Ser Ala Phe Ala Ala Val Met Lys Tyr Cys Glu Asp His
            290                 295                 300

Pro Glu Leu Thr Glu Asp Asp Val Ile Val Ala Ile Phe Pro Asp Ser
305                 310                 315                 320

Ile Arg Ser Tyr Leu Thr Lys Phe Val Asp Asp Glu Trp Leu Lys Lys
                325                 330                 335

Asn Asp Leu Trp Asp Asp Glu Ile Leu Thr Arg Phe Asp Ala Ser Lys
            340                 345                 350

Pro Glu Ala Ser Thr Asn Thr Tyr Ala Asp Val Phe Gly Asp Ala Thr
            355                 360                 365

Val Lys Asp Leu His Leu Lys Pro Val Val Ser Val Lys Glu Thr Ala
370                 375                 380

Lys Val Ala Asp Val Ile Lys Ile Leu Lys Asp Asn Gly Phe Asp Gln
385                 390                 395                 400

Leu Pro Val Leu Ala Glu Asp Gly Lys Leu Ser Gly Leu Val Ile Tyr
                405                 410                 415

Met Ser Cys

<210> SEQ ID NO 9
<211> LENGTH: 645
<212> TYPE: PRT
<213> ORGANISM: Saccharomyces bayanus

<400> SEQUENCE: 9

Met Ser Ile Ser Ala Ala Lys Arg Ser Leu Asp Leu Val Ser Ser Ser
1               5                   10                  15

Ser Leu Ala Gln Ser Asp Asp Ser Val Ser His His Asp Glu Val Glu
            20                  25                  30

Asn Asp His Ile His Asp Asp Met His Asp Asn Asp Asn Asp Gln
        35                  40                  45

Pro Arg Arg Lys Gly Ser Lys Thr Ser Lys Lys Gln Asp Leu Asp Pro
    50                  55                  60

```
Glu Thr Lys Leu Lys Arg Thr Ala Gln Asn Arg Ala Ala Gln Arg Ala
 65                  70                  75                  80

Phe Arg Glu Arg Lys Glu Arg Lys Met Lys Glu Leu Glu Lys Lys Val
             85                  90                  95

His Ser Leu Glu Ser Ile Gln Gln Glu Asn Glu Val Glu Ala Thr Phe
            100                 105                 110

Leu Arg Asp Gln Leu Val Thr Leu Val Ser Glu Leu Lys Lys Tyr Arg
        115                 120                 125

Pro Glu Thr Arg Asn Asp Ser Lys Val Leu Glu Tyr Leu Ala Arg Arg
    130                 135                 140

Asp Pro Asn Leu His Pro Pro Asn Ser Asn Thr Asn Asn Asn Ser Glu
145                 150                 155                 160

Pro Ile Val Thr Pro Asn Asp Ile Gln Lys Asn Val Lys Gln Lys
                165                 170                 175

Met Asn Phe Thr Phe Gln Tyr Pro Leu Asp Asn Asp Asp Asn Asp Gly
            180                 185                 190

Lys Asn Met Glu Lys Gln Leu Pro Ser Pro Asn Asp Pro Asn His Ser
        195                 200                 205

Ala His Val Pro Ile Ala Pro Thr Gln Lys Lys Leu Ser Asp Ala Thr
    210                 215                 220

Asp Ser Ser Thr Ala Thr Leu Asp Ser Phe Ser Asn Asn Asn Asp Val
225                 230                 235                 240

Leu Asn Ile Thr Pro Asn Ser Ser Ser Met Asp Trp Leu Asp Asn
                245                 250                 255

Val Met Tyr Thr Asn Lys Phe Val Ala Gly Gly Asp Gln Lys Asn Ala
            260                 265                 270

Ser Asn Glu Ser Lys Ser Lys Pro Lys Gly Val Asp Ser Asn Met Phe
        275                 280                 285

Ser Asn Asp Phe Asn Phe Glu Asn Gln Phe Asp Glu Gln Val Ser Glu
    290                 295                 300

Phe Cys Ser Lys Met Asn Gln Ala Cys Gly Thr Lys Gln Cys Pro Ile
305                 310                 315                 320

Pro Lys Lys Ser Val His Gln Leu Asp Lys Glu Val Phe Ala Ser Ser
                325                 330                 335

Ser Val Leu Ser Ala Asn Ser Pro Val Leu Thr Asn Thr Trp Asp Ser
            340                 345                 350

His Ser Asn Val Thr Thr Asn Thr Pro Ala Asn Ile Thr Thr Asn Gly
        355                 360                 365

Ser Ser Ser Ser Ser Phe Gly Gln Pro Gly Phe Asp Leu Asn Thr Asn
    370                 375                 380

His Tyr Ala Thr Asn Asp Lys Tyr Thr Asp Asn Ser Asp Asn Asn Lys
385                 390                 395                 400

Thr Asn Asn Tyr Asn Asp Ile Leu Pro Phe Ile Ser Glu Ser Pro Phe
                405                 410                 415

Asp Met Asn Gln Val Thr Asn Phe Phe Ser Pro Gly Thr Asn Asn Thr
            420                 425                 430

Thr Asn Ala Asn Thr Asn Ser His Asn Pro Ser Leu Gln Gln Ser
        435                 440                 445

Thr Lys Asp Asp Ile Pro Phe Ile Asn Thr Ser Leu Ala Phe Pro Asp
    450                 455                 460

Asp Asn Pro Thr Asn Ile Gln Leu Gln Pro Leu Ser Gln Ser Gln His
465                 470                 475                 480
```

```
Gln Asn Lys Phe Asp Tyr Asp Met Phe Phe Arg Asp Ser Ser Lys Glu
                485                 490                 495

Gly Asn Asn Leu Phe Glu Glu Phe Leu Glu Glu Asp Asp Asp Asp Asp
            500                 505                 510

Asp Asp Asp Gly Asn Asp Gly Asn Asp Asn Asp Gly Glu Ala Val Asn
        515                 520                 525

Ala Ser Asp Asp Glu Ser Asn Leu Ile Lys Asn Lys Leu Ile Asn Glu
    530                 535                 540

Glu Pro Gln Gln Gln Ser Gln Cys His Leu Ser Thr Pro Lys Asn Gly
545                 550                 555                 560

Ser Glu Val Leu Gln Asn Lys Asn Ser Ser Asn Ser Glu Asp Val Asn
                565                 570                 575

Asp Asn Asp Asn Glu Val Val Pro Ser Lys Glu Gly Ser Leu Leu Arg
            580                 585                 590

Cys Ser Glu Ile Trp Asp Arg Ile Thr Thr His Pro Lys Tyr Ser Asp
        595                 600                 605

Ile Asp Val Asp Gly Leu Cys Ser Glu Leu Met Ala Lys Ala Lys Cys
    610                 615                 620

Ser Glu Arg Gly Val Val Ile Asn Ala Glu Asp Val Gln Leu Ala Leu
625                 630                 635                 640

Asn Lys His Met Asn
                645

<210> SEQ ID NO 10
<211> LENGTH: 507
<212> TYPE: PRT
<213> ORGANISM: Saccharomyces kudriavzevii
<220> FEATURE:
<221> NAME/KEY: misc_feature
<222> LOCATION: (476)..(476)
<223> OTHER INFORMATION: Xaa can be any naturally occurring amino acid

<400> SEQUENCE: 10

Met Thr Lys Ser Glu Gln Gln Ala Asp Ser Arg His Asn Val Ile Asp
1               5                   10                  15

Leu Val Gly Asn Thr Pro Leu Ile Ala Leu Lys Lys Leu Pro Lys Ala
            20                  25                  30

Leu Gly Ile Lys Pro Gln Ile Tyr Ala Lys Leu Glu Leu Tyr Asn Pro
        35                  40                  45

Gly Gly Ser Ile Lys Asp Arg Ile Ala Lys Ser Met Val Glu Glu Ala
    50                  55                  60

Glu Ala Ser Gly Arg Ile His Pro Ser Arg Ser Thr Leu Ile Glu Pro
65                  70                  75                  80

Thr Ser Gly Asn Thr Gly Ile Gly Leu Ala Leu Ile Gly Ala Ile Lys
                85                  90                  95

Gly Tyr Arg Thr Ile Ile Thr Leu Pro Glu Lys Met Ser Asn Glu Lys
            100                 105                 110

Val Ser Val Leu Lys Ala Leu Gly Ala Glu Ile Ile Arg Thr Pro Thr
        115                 120                 125

Ala Ala Ala Trp Asp Ser Pro Glu Ser His Ile Gly Val Ala Lys Lys
    130                 135                 140

Leu Glu Lys Glu Ile Pro Gly Ala Val Ile Leu Asp Gln Tyr Asn Asn
145                 150                 155                 160

Met Met Asn Pro Glu Ala His Tyr Phe Gly Thr Gly Arg Glu Ile Gln
                165                 170                 175
```

-continued

```
Arg Gln Leu Glu Asp Leu Asn Leu Phe Asp Asn Leu Arg Ala Val Val
            180                 185                 190

Ala Gly Ala Gly Thr Gly Gly Thr Ile Ser Gly Ile Ser Lys Tyr Leu
        195                 200                 205

Lys Glu Gln Asn Asp Lys Ile Gln Ile Val Gly Ala Asp Pro Phe Gly
    210                 215                 220

Ser Ile Leu Ala Gln Pro Glu Asn Leu Asn Lys Thr Asp Ile Thr Asp
225                 230                 235                 240

Tyr Lys Val Glu Gly Ile Gly Tyr Asp Phe Val Pro Gln Val Leu Asp
                245                 250                 255

Arg Lys Leu Ile Asp Val Trp Tyr Lys Thr Asp Asp Lys Pro Ser Phe
            260                 265                 270

Lys Tyr Ala Arg Gln Leu Ile Ser Asn Glu Gly Val Leu Val Gly Gly
        275                 280                 285

Ser Ser Gly Ser Ala Phe Thr Ala Val Val Lys Tyr Cys Glu Asp His
    290                 295                 300

Pro Glu Leu Thr Glu Asp Asp Val Ile Val Ala Ile Phe Pro Asp Ser
305                 310                 315                 320

Ile Arg Ser Tyr Leu Thr Lys Phe Val Asp Asp Glu Trp Leu Lys Lys
                325                 330                 335

Asn Asn Leu Trp Asp Asp Asp Val Leu Ala Arg Phe Asp Ser Pro Lys
            340                 345                 350

Leu Glu Ala Ser Thr Thr Lys Tyr Ala Asp Val Phe Gly Asn Ala Thr
        355                 360                 365

Val Lys Asp Leu His Leu Lys Pro Val Val Ser Val Lys Glu Thr Ala
    370                 375                 380

Lys Val Thr Asp Val Ile Lys Ile Leu Lys Asp Asn Gly Phe Asp Gln
385                 390                 395                 400

Leu Pro Val Leu Thr Glu Asp Gly Lys Leu Ser Gly Leu Val Thr Leu
                405                 410                 415

Ser Glu Leu Leu Arg Lys Leu Ser Ile Asn Asn Ser Asn Asn Asp Asn
            420                 425                 430

Thr Ile Lys Gly Lys Tyr Leu Asp Phe Lys Lys Leu Asn Asn Phe Asn
        435                 440                 445

Asp Val Ser Ser Tyr Asn Glu Asn Lys Ser Gly Lys Lys Lys Phe Ile
    450                 455                 460

Lys Phe Asp Glu Asn Ser Lys Leu Ser Asp Leu Xaa Arg Phe Phe Glu
465                 470                 475                 480

Lys Asn Ser Ser Ala Val Ile Thr Asp Gly Leu Lys Pro Ile His Ile
                485                 490                 495

Val Thr Lys Met Asp Leu Leu Ser Tyr Leu Ala
            500                 505

<210> SEQ ID NO 11
<211> LENGTH: 665
<212> TYPE: PRT
<213> ORGANISM: Saccharomyces kudriavzevii

<400> SEQUENCE: 11

Met Ser Val Ser Thr Ala Lys Arg Ser Leu Asp Leu Ala Ser Pro Gly
1               5                   10                  15

Ser Leu Ala Glu Phe Asp Asp Ser Ala Ala His His Asp Glu Ile Glu
            20                  25                  30

Asn Glu His Arg His Asp Ser Thr Arg Asp Asp Asp Asn Glu Gln
        35                  40                  45
```

```
Pro Lys Lys Gly Thr Lys Ile Ser Lys Lys Gln Asp Leu Asp Pro
 50                  55                  60
Glu Thr Lys Gln Lys Arg Thr Ala Gln Asn Arg Ala Ala Gln Arg Ala
 65                  70                  75                  80
Phe Arg Glu Arg Lys Glu Arg Lys Met Met Glu Leu Glu Lys Lys Val
                     85                  90                  95
Gln Gly Leu Glu Asn Ile Gln Gln Asn Glu Val Glu Ala Thr Phe
                100                 105                 110
Leu Arg Asp Gln Leu Val Thr Leu Val Asn Glu Leu Lys Lys Tyr Arg
                115                 120                 125
Pro Glu Thr Arg Asn Asp Ser Lys Val Leu Glu Tyr Leu Ala Ser Arg
130                 135                 140
Asp Pro Asn Leu Pro Thr Ser Asn Asn Ser Thr Asn Ser Ser Ser Asn
145                 150                 155                 160
Arg Pro Ile Ile Thr Pro Ser Glu Glu Ile Gln Glu Asn Val Arg Gln
                165                 170                 175
Lys Met Asn Phe Thr Phe Gln Tyr Ala Leu Asp Asn Asp Ser Lys Asn
                180                 185                 190
Leu Glu Lys Gln Leu Pro Ser Pro Asn Asp Pro Ser His Ser Ala Pro
                195                 200                 205
Ile Pro Thr Thr Gln Ala Gln Lys Lys Ser Ser Asp Ala Thr Asp Ser
210                 215                 220
Ser Thr Ala Thr Leu Asp Ser Leu Ser Asn Ser His Asp Val Leu Asn
225                 230                 235                 240
Asn Thr Pro Asn Ser Ser Ser Met Asp Trp Leu Asp Asn Val Ile
                245                 250                 255
Tyr Thr Asn Arg Phe Val Ala Gly Gly Asp Gly Ser Lys Leu Glu Val
                260                 265                 270
Lys Asn Val Asp Ser Asn Met Phe Ser Asn Asn Phe Asn Phe Glu Asn
                275                 280                 285
Gln Phe Asp Glu Gln Val Ser Glu Phe Cys Ser Lys Met Asn Gln Val
                290                 295                 300
Cys Gly Thr Arg Gln Cys Pro Ile Pro Lys Lys Pro Val Ser Thr Leu
305                 310                 315                 320
Asp Gln Glu Val Phe Ala Ser Ser Ile Leu Ser Ala Asn Ser Pro
                325                 330                 335
Ala Leu Thr Asn Thr Trp Glu Ser His Ser Asn Ile Thr Ala Asn Thr
                340                 345                 350
Pro Ala Asn Ile Thr Thr Asn Asp Thr Ser Leu Ser Gly Phe Gly Gln
                355                 360                 365
Leu Gly Phe Glu Leu Thr Thr Ser Arg His Ala Ala Glu Glu Asn Ser
                370                 375                 380
Thr Gly Asn Thr Asp Asn Asp Asn Asn Ser Gly Asp Ser Ser Asn Asn
385                 390                 395                 400
Lys Asn Asn Asn Asn Asn Asn Asn Asn Asn Ser Asn Asn
                405                 410                 415
Lys Asn Asn Asn Asn Gly Asp Asp Gly Gly Val Ile Pro Phe Ile
                420                 425                 430
Ser Asp Ser Pro Phe Asp Met Asn Gln Val Thr Asn Phe Phe Ser Pro
                435                 440                 445
Gly Ser Thr Asn Asn Ile Asn Ile Ala Ala Ser Ser Ala Asn Pro Ser
                450                 455                 460
```

Leu Ser Gln Asn Thr Lys Asp Asp Val Pro Phe Ile Asn Ala Gly Leu
465                 470                 475                 480

Ala Phe Pro Asp Glu Asn Pro Thr Asn Ile Gln Leu Gln Pro Phe Ser
                485                 490                 495

Glu Ser Gln Ser Gln Asn Lys Phe Asp Tyr Asp Met Phe Phe Arg Asp
                500                 505                 510

Ser Ser Arg Ala Gly Asn Ser Leu Phe Glu Glu Phe Leu Glu Glu Glu
            515                 520                 525

Glu Asp Asp Asp Asp Asp Asn Asn Glu Lys Ala Thr Asn Ala
            530                 535                 540

Ser Asp Asp Glu Ser Ser Leu Ile Arg Asn Gln Leu Ile Asn Glu Glu
545                 550                 555                 560

Pro Gln Pro Leu Asn Gln Asn Ser Leu Ser Ser Leu Asn Asn Glu Lys
                565                 570                 575

Glu Thr Ser Pro Lys Thr Asn Ser Gly Gly Thr Gln Asn Ala Asn Asp
                580                 585                 590

Ser Asp Gly Asn Asp Asn Asp Asn Asp Val Val Pro Ser Lys Glu Gly
            595                 600                 605

Ser Leu Leu Arg Cys Ser Glu Ile Trp Asp Arg Ile Thr Thr His Pro
610                 615                 620

Lys Tyr Ser Asp Ile Asp Val Asp Gly Leu Cys Ser Glu Leu Met Ala
625                 630                 635                 640

Lys Ala Lys Cys Ser Glu Arg Gly Val Val Ile Asn Ala Glu Asp Val
                645                 650                 655

Gln Leu Ala Leu Asn Lys His Met Asn
                660                 665

<210> SEQ ID NO 12
<211> LENGTH: 493
<212> TYPE: PRT
<213> ORGANISM: Candida utilis

<400> SEQUENCE: 12

Met Ser Glu Arg Asp Ser Lys Ile Pro Ala Leu Asn Glu Asn Ile Leu
1               5                   10                  15

Glu Leu Ile Gly Asn Thr Pro Leu Val Lys Leu Asn Lys Val Pro Gln
                20                  25                  30

Ser Leu Gly Ile Lys Pro Gln Val Leu Ala Lys Val Glu Leu Phe Asn
            35                  40                  45

Ala Gly Gly Ser Ile Lys Asp Arg Ile Ala Leu Arg Met Val Glu Glu
50                  55                  60

Ala Glu Arg Glu Gly Arg Ile Lys Pro Gly Tyr Val Leu Cys Glu Pro
65                  70                  75                  80

Thr Ser Gly Asn Thr Gly Ile Gly Leu Ala Leu Ala Gly Ala Val Lys
                85                  90                  95

Gly Tyr Arg Val Ile Ile Thr Leu Pro Glu Lys Met Ser Asn Glu Lys
                100                 105                 110

Val Ser Val Leu Lys Ala Leu Gly Ala Glu Ile Ile Arg Thr Pro Asn
            115                 120                 125

Glu Ala Ala Phe Asp Ser Pro Glu Ser His Ile Gly Val Ala Lys Arg
            130                 135                 140

Leu Glu Lys Glu Ile Lys Asn Cys Val Ile Leu Asp Gln Tyr Gly Asn
145                 150                 155                 160

Ile Asn Asn Pro Asp Ala His Tyr Tyr Thr Thr Gly Tyr Glu Ile Trp
                165                 170                 175

```
Lys Gln Thr Gly Gly Lys Leu Asn Ala Leu Val Ala Gly Ala Gly Thr
            180                 185                 190

Gly Gly Thr Ile Thr Gly Ile Ser Arg Tyr Leu Lys Glu Gln Asp Pro
        195                 200                 205

Ser Ile Thr Val Val Gly Ala Asp Pro Val Gly Ser Ile Leu Ala Val
        210                 215                 220

Pro Glu Thr Leu Asn Lys Thr Asp Val Thr Gln Tyr Lys Val Glu Gly
225                 230                 235                 240

Ile Gly Tyr Asp Phe Ile Pro Asp Val Leu Lys Arg Glu Ser Val Asp
                245                 250                 255

Gln Trp Tyr Lys Thr Glu Asp Gln Glu Ser Phe Thr Leu Ala Arg Arg
            260                 265                 270

Ile Ile Ser Glu Glu Gly Ile Leu Val Gly Ser Ser Gly Ser Ala
            275                 280                 285

Met Ala Ala Val Val Lys Tyr Cys Asn Asp His Pro Glu Leu Thr Glu
        290                 295                 300

Lys Asp Thr Ile Val Val Phe Pro Asp Ser Ile Arg Ser Tyr Leu
305                 310                 315                 320

Thr Lys Phe Ala Asp Asp Glu Trp Met Lys Ser Asn Gly Phe Glu Ile
                325                 330                 335

Asn Thr Lys Pro Lys Ala Glu Asp Leu Gln Thr Glu Thr Ile Ala Ser
            340                 345                 350

Leu Asn Leu Lys Pro Val Ala Val Tyr Ser Asp Glu Lys Val Gln
        355                 360                 365

Thr Val Ile Lys Leu Leu Lys Asp Asn Gly Phe Asp Gln Leu Pro Val
        370                 375                 380

Leu Ala Lys Gly Thr Glu Lys Leu Ile Gly Leu Ile Thr Leu Ser Lys
385                 390                 395                 400

Leu Leu Lys Ser Val Ser Ser Gly Ser Val Ser Leu Asn Asp Asn Ile
                405                 410                 415

Glu Ser Ile Ile Leu Asp Phe Arg Lys Leu Asn Asn Phe Asp Asp Val
            420                 425                 430

Asn Leu Phe Asn Asp Asn Lys Ser Ser Lys Lys Phe Gln Gln Ile
        435                 440                 445

Thr Thr Lys Thr Thr Leu Lys Glu Leu Asn Lys Phe Phe Glu Lys Asn
450                 455                 460

Ala Cys Ala Ile Val Thr Asp Glu Asn Leu Lys Pro Val His Val Val
465                 470                 475                 480

Thr Lys Val Asp Leu Leu Asp Tyr Phe Val Gly Gly Ile
            485                 490

<210> SEQ ID NO 13
<211> LENGTH: 438
<212> TYPE: PRT
<213> ORGANISM: Candida utilis

<400> SEQUENCE: 13

Met Thr Glu Tyr Ala Lys Arg His Thr Asp Ser Leu Leu Glu Asn Pro
1               5                   10                  15

Glu Ser Lys Arg Pro Glu Pro Asp Ala Thr Ala Thr Ser Glu Gly Val
            20                  25                  30

Leu Lys Lys Pro Asn Lys Pro Gly Arg Lys Pro Leu Asp Thr Glu Pro
        35                  40                  45

Lys Asn Lys Arg Thr Ala Gln Asn Arg Ala Ala Gln Arg Ala Phe Arg
50                  55                  60
```

```
Glu Arg Lys Glu Arg Lys Met Lys Glu Leu Glu Lys Ile Thr Thr
 65                  70                  75                  80

Leu Glu Asp Glu Lys Arg Phe Ala Thr Thr Glu Ser Glu Phe Leu Arg
                 85                  90                  95

Leu Gln Val Gln Met Leu Thr Gln Glu Leu Ala Lys His Arg Gly Thr
            100                 105                 110

Thr Asp Leu Ser Asp Leu Lys Leu Pro Leu Phe Thr Ser Pro Thr Glu
        115                 120                 125

Thr Asn Ser Thr Pro Asn Ser Glu Val Ser Thr Val Leu Thr Ser Val
    130                 135                 140

Gly Ser Asp Asn Glu Leu Lys Arg Thr Gln Gln Glu Phe Ser Phe Glu
145                 150                 155                 160

Phe Pro Trp Ser Arg Lys Ser Ser Thr Thr Asn Ser Lys Arg Ser Pro
                165                 170                 175

Asn Ala Ser Asn Ala Ser Ser Asn Asn Val Pro Thr Leu Ala Ser Asp
            180                 185                 190

Ala Ser Thr Cys Ser Ser Gln Ser Pro Phe Asp Leu Tyr Asn Ser
        195                 200                 205

Glu Glu Gln Asn Glu Leu Pro Leu Phe Asn Lys Val Val Lys Asp Ser
210                 215                 220

Thr Lys Met Pro Thr Glu Lys Phe Asn Phe Ser Glu His Phe Asp Glu
225                 230                 235                 240

Gly Val Asn Phe Cys Ser Asp Leu Gly Lys Ala Cys Gly Thr Arg Glu
                245                 250                 255

Cys Pro Ile Pro Glu Val Lys Ser Asn Thr Asn Thr Pro Leu Pro Val
            260                 265                 270

Glu Leu Asp His Asn Asp Pro Leu Asn Ser Leu Glu Asp Pro Ala Leu
            275                 280                 285

Asp Phe Asn Phe Gly Thr Phe Asp Pro Thr Val Ala Phe Ala Asn Glu
        290                 295                 300

Ser Ser Tyr Ala Asp Leu Phe Asp Ser His Gly Glu Ser Asp Pro Leu
305                 310                 315                 320

Val Gly Leu Val Thr Glu Glu Ser Ala Tyr Asp Pro Phe Ser Met Phe
                325                 330                 335

Lys Asp Thr His Ala Arg Val Val Glu Arg Arg Glu Glu Ala Glu His
            340                 345                 350

Glu Glu Glu Glu Glu Pro Gln Gln Glu Gln Glu Gln Glu Gln Glu Gln
        355                 360                 365

Glu Gln Asp Pro Asp Val Val Pro Ser Asn Glu His Arg Leu Met Lys
    370                 375                 380

Cys Thr Glu Ile Trp Asp Arg Ile Thr Ser His Pro Lys Tyr Ala Asp
385                 390                 395                 400

Ile Asp Ile Asp Gly Leu Cys Ser Glu Leu Arg Ser Lys Ala Lys Cys
                405                 410                 415

Ser Asp Lys Gly Val Val Ile Asp Tyr Lys Asp Val Asn Gln Val Ile
            420                 425                 430

Gln Arg Asn Ile Arg Lys
            435

<210> SEQ ID NO 14
<211> LENGTH: 497
<212> TYPE: PRT
<213> ORGANISM: Torulaspora delbrueckii
```

<400> SEQUENCE: 14

```
Met Thr Val Asp Thr Arg Thr Asn Val Ile Asp Leu Val Gly Asn Thr
1               5                   10                  15

Pro Met Val Glu Leu Thr Lys Leu Pro Ala Ala Leu Gly Val Lys Pro
            20                  25                  30

Arg Val Tyr Ala Lys Leu Glu Leu Tyr Asn Pro Gly Gly Ser Ile Lys
        35                  40                  45

Asp Arg Ile Ala Lys Ser Met Ile Glu Tyr Ala Glu Ala Gly Glu
    50                  55                  60

Ile His Pro Asp Arg Thr Thr Leu Ile Glu Pro Thr Ser Gly Asn Thr
65                  70                  75                  80

Gly Ile Gly Leu Ala Leu Ile Gly Ala Ile Lys Gly Tyr Arg Thr Ile
                85                  90                  95

Ile Thr Leu Pro Glu Lys Met Ser Asn Glu Lys Val Ser Val Leu Lys
            100                 105                 110

Ala Leu Gly Ala Glu Ile Val Arg Thr Pro Thr Glu Ala Ala Trp Asp
            115                 120                 125

Ser Pro Glu Ser His Ile Gly Val Ala Glu Arg Leu Gln Lys Glu Ile
    130                 135                 140

Pro Gly Ala Val Ile Leu Asp Gln Tyr Asn Asn Pro Arg Asn Pro Glu
145                 150                 155                 160

Ala His Tyr Leu Gly Thr Gly Lys Glu Ile Gln Asp Gln Leu Glu Lys
                165                 170                 175

Leu Gly Lys Phe Asp Ser Leu Lys Ala Val Ile Ala Gly Ala Gly Thr
            180                 185                 190

Gly Gly Thr Ile Ser Gly Ile Ser Lys Trp Leu Lys Gly Lys Asn Glu
        195                 200                 205

Asp Ile Lys Ile Val Gly Ala Asp Pro Val Gly Ser Ile Leu Ala Gln
    210                 215                 220

Pro Gln Ser Leu Asn Glu Thr Ser Ala Pro Gly Tyr Lys Val Glu Gly
225                 230                 235                 240

Ile Gly Tyr Asp Phe Val Pro Asn Val Leu Asp Arg Ser Leu Val Asp
                245                 250                 255

Val Trp Tyr Lys Thr Glu Asp Lys Ala Ser Phe Lys Tyr Ala Arg Gln
            260                 265                 270

Leu Ile Ser Asn Glu Gly Val Leu Ile Gly Gly Ser Ser Gly Ser Ala
        275                 280                 285

Phe Thr Ala Leu Leu Lys Tyr Val Ala Glu His Pro Glu Leu Thr Glu
    290                 295                 300

Asp Asp Val Leu Val Val Phe Pro Asp Ser Ile Arg Ser Tyr Leu
305                 310                 315                 320

Thr Lys Phe Val Asp Asp Glu Trp Leu Lys Asn Asp Leu Trp Asp
                325                 330                 335

Asp Glu Val Leu Ala Arg Val Lys Gln Thr Ser Thr Val Thr Lys Lys
            340                 345                 350

Asp Pro Phe Asn Gly Ala Lys Val Gln Asp Leu His Leu Lys Pro Val
        355                 360                 365

Val Ser Val Lys Glu Ser Ala Ser Leu Ala Glu Val Ile Lys Ile Leu
    370                 375                 380

Lys Asp Asn Ala Phe Asp Gln Leu Pro Val Leu Thr Glu Asp Gly Lys
385                 390                 395                 400

Leu Ser Gly Leu Val Thr Leu Ser Leu Leu Leu Arg Lys Ile Ser Asn
                405                 410                 415
```

```
Gly Thr Ser Lys Asp Asp Ser Ile Lys Asp Ile Tyr Phe Asp Phe Lys
                420                 425                 430

Lys Leu Asn Asn Phe Asp Gln Val Ser Ser Tyr Asn Glu Asn Lys Ser
            435                 440                 445

Gly Lys Lys Lys Phe Thr Val Phe Thr Asn Gly Ser Lys Leu Ser Asp
        450                 455                 460

Leu Asn Ser Phe Phe Glu Lys Asn Ser Ser Ala Ile Ile Thr Asp Gly
465                 470                 475                 480

Leu Arg Pro Val His Ile Val Thr Lys Ile Asp Leu Leu Asn Tyr Leu
                485                 490                 495

Ala

<210> SEQ ID NO 15
<211> LENGTH: 466
<212> TYPE: PRT
<213> ORGANISM: Torulaspora delbrueckii

<400> SEQUENCE: 15

Met Glu Arg Ala Leu Pro Pro Leu Ile Ser Arg Thr Ser Thr Arg Ser
1               5                   10                  15

Asn Thr Ser Ser Met Ser Ala Met Ser Ala Ser Thr Val Lys Arg Pro
            20                  25                  30

Leu Glu Gln Ser Ser Ser Pro Met Ala Pro Ala Ala Lys Gly Ser Lys
        35                  40                  45

Pro Gly Arg Lys Pro Leu Asp Glu Glu Thr Lys Asn Lys Arg Thr Ala
    50                  55                  60

Gln Asn Arg Ala Ala Gln Arg Ala Phe Arg Glu Arg Lys Glu Lys Lys
65                  70                  75                  80

Met Lys Glu Leu Glu Asp Lys Val Gln Ser Leu Glu Gln Ala Asn Arg
                85                  90                  95

Asp Thr Val Val Glu Ser Glu Phe Leu Arg Ser Gln Leu Leu Thr Leu
            100                 105                 110

Val Asn Glu Leu Lys Lys Tyr Arg Pro Ala Lys Ala Asn Asp Leu Gln
        115                 120                 125

Val Leu Asp Tyr Leu Ala Lys His Glu Arg Thr Glu Pro Thr Asp Lys
130                 135                 140

Glu Ile Glu Gln Ser Val Gln Lys Lys Met Asp Phe Thr Phe Ala Phe
145                 150                 155                 160

Pro Trp Lys Asp Arg Lys Glu Ala Glu Ala Gln Ala Gln His Phe Pro
                165                 170                 175

Ser Pro Gly Ser Ser Met Leu Ser Ser Ser Ala Ser Val Asn Ser
            180                 185                 190

Ala Ala Ser Pro Ser Asn Lys Arg Arg Ser Thr Ala Ser Arg Ser Thr
        195                 200                 205

Ser Thr Ser Thr Ser Thr Thr Gly Trp Met Asp Asn Val Phe Tyr Ser
    210                 215                 220

Asp Asp Ala Gln Lys Leu Pro Gln Phe Ala Ile Lys Gly Asp Ser Thr
225                 230                 235                 240

Ala Asp Pro Leu Phe Ser Asn Glu Phe Asn Phe Asp Asp Gln Phe Asp
                245                 250                 255

Glu Gln Val Ser Gln Phe Cys Thr Lys Met Asn Lys Ala Cys Gly Thr
            260                 265                 270

Arg Glu Cys Pro Ile Pro Gly Phe Thr Pro Gln Met Ala Ser Pro Gln
        275                 280                 285
```

```
Val Ala Ser Pro Gln Ile Leu Thr Asn Ser Trp Asp Thr Val Ala Ser
    290                 295                 300
Pro Ala Phe Gly Gln Gln Ser Leu Ala Pro Ser Lys Lys Gln Leu Thr
305                 310                 315                 320
Lys Thr Pro Pro Ser Gln Pro Glu Leu Pro Phe Ile Asp Pro Thr Met
                325                 330                 335
Ala Phe Pro Thr Asp Asp Glu Gly Leu Phe Phe Arg Thr His Arg
            340                 345                 350
Asp Glu Asn Ser Leu Phe Ala Glu Leu Leu Asp Glu Val Glu Pro Thr
        355                 360                 365
Asp Asn Asn Phe Val Asn Glu Asn Leu Ile Asn Glu Glu Pro Ser Thr
    370                 375                 380
Thr Thr Ala Val Ala Glu Glu Thr Arg Pro Lys Pro Lys Thr Glu Thr
385                 390                 395                 400
Asp Val Val Pro Ser Arg Asp Gly Lys Leu Leu Lys Cys Ser Glu Val
                405                 410                 415
Trp Asp Arg Ile Thr Thr His Pro Lys Tyr Ser Ala Ile Asp Ile Asp
            420                 425                 430
Gly Leu Cys Gly Glu Leu Met Thr Lys Ala Lys Cys Ser Glu Lys Gly
        435                 440                 445
Val Val Val Gln Ala Glu Asp Val Gln Arg Val Leu Asp Lys His Met
    450                 455                 460
Asp Val
465

<210> SEQ ID NO 16
<211> LENGTH: 500
<212> TYPE: PRT
<213> ORGANISM: Zygosaccharomyces bailii

<400> SEQUENCE: 16

Met Val Val Asp Thr Arg Thr Asn Val Ile Asp Leu Val Gly Asn Thr
1               5                   10                  15
Pro Leu Ile Glu Leu Lys Thr Leu Pro Lys Ala Leu Gly Ile Lys Pro
            20                  25                  30
Lys Val Tyr Ala Lys Leu Glu Leu Tyr Asn Pro Gly Gly Ser Ile Lys
        35                  40                  45
Asp Arg Ile Ala Lys Thr Met Ile Glu Tyr Ala Glu Lys Asn Gly Glu
    50                  55                  60
Ile His Pro Asp Arg Thr Thr Leu Ile Glu Pro Thr Ser Gly Asn Thr
65                  70                  75                  80
Gly Ile Gly Leu Ala Leu Ile Gly Ala Ile Lys Gly Tyr Arg Thr Ile
                85                  90                  95
Ile Thr Leu Pro Glu Lys Met Ser Asn Glu Lys Val Ser Val Leu Lys
            100                 105                 110
Ala Leu Gly Ala Glu Ile Val Arg Thr Pro Thr Ser Ala Ala Trp Asp
        115                 120                 125
Ser Pro Glu Ser His Ile Gly Val Ala Lys Arg Leu Glu Lys Glu Ile
    130                 135                 140
Pro Gly Ala Val Ile Leu Asp Gln Tyr Asn Asn Pro Arg Asn Pro Glu
145                 150                 155                 160
Ala His Tyr Tyr Gly Thr Gly Lys Glu Ile Gln Glu Gln Leu Gln Asn
                165                 170                 175
Leu Asn Glu Phe Asp Asn Leu Lys Ala Val Ile Ala Gly Ala Gly Thr
            180                 185                 190
```

```
Gly Gly Thr Ile Thr Gly Ile Ser Lys Tyr Leu Lys Glu Gln Asn Asp
            195                 200                 205

Asn Ile Thr Ile Val Gly Ala Asp Pro Phe Gly Ser Ile Leu Ala Gln
        210                 215                 220

Pro Glu Ser Leu Asn Lys Thr Asp Val Gly Glu Tyr Lys Val Glu Gly
225                 230                 235                 240

Ile Gly Tyr Asp Phe Val Pro Lys Val Leu Asn Arg Asn Glu Ile Asp
                245                 250                 255

Thr Trp Tyr Lys Thr Asp Asp Lys Asp Ser Phe Val Tyr Ala Arg Gln
            260                 265                 270

Leu Ile Ser Asn Glu Gly Val Leu Val Gly Gly Ser Ser Gly Ser Ala
        275                 280                 285

Phe Ser Ala Leu Val Lys Tyr Ala Lys Asp His Pro Glu Leu Asp Glu
        290                 295                 300

Asn Asp Val Leu Val Ala Ile Phe Pro Asp Ser Ile Arg Ser Tyr Leu
305                 310                 315                 320

Thr Lys Phe Val Asp Asp Glu Trp Leu Lys Asn Asn Leu Trp Ser
                325                 330                 335

Asp Asp Val Leu Ala Arg Val Gly Thr Lys Gly Pro Ser Asn Ile Asp
            340                 345                 350

Arg Lys Asp Pro Phe His Gly Ala Thr Val Gln Asp Leu Lys Leu Lys
        355                 360                 365

Pro Val Val Ser Val Lys Glu Asn Ala Ala Val Ala Asp Ala Ile Gln
370                 375                 380

Ile Leu Arg Gln Asn Ala Phe Asp Gln Leu Pro Val Leu Ala Glu Asp
385                 390                 395                 400

Gly Lys Leu Ser Gly Leu Val Thr Leu Ser Gln Leu Leu Lys Lys Leu
            405                 410                 415

Ser Asn Gly Thr Ala Thr Lys Glu Asp Lys Ile Lys Ser Phe Tyr Ile
        420                 425                 430

Asp Phe Arg Lys Leu Asn Asn Phe Asp Asp Val Ser Ser Tyr Asn Glu
        435                 440                 445

Asn Lys Ser Gly Lys Lys Lys Phe Val Gln Phe Thr Asn Ser Ser Lys
450                 455                 460

Leu Ser Asp Leu Asn Asn Phe Phe Glu Lys Asn Ser Ser Ala Ile Ile
465                 470                 475                 480

Thr Glu Gly Ser Lys Pro Val His Ile Val Thr Lys Ile Asp Leu Leu
            485                 490                 495

Asp Tyr Leu Ile
            500

<210> SEQ ID NO 17
<211> LENGTH: 547
<212> TYPE: PRT
<213> ORGANISM: Zygosaccharomyces bailii

<400> SEQUENCE: 17

Met Ser Ala Thr Ser Ala Lys Arg Pro Leu Glu Pro Thr Val Ser Leu
1               5                   10                  15

Glu Phe Ala Asn Asp Glu Ala Glu Lys Ser Pro Thr Ser Glu Glu Pro
            20                  25                  30

Arg Lys Lys Gly Gly Lys Pro Gly Arg Lys Pro Leu Asp Ser Glu Ala
        35                  40                  45

Lys Asn Lys Arg Thr Ala Gln Asn Arg Ala Ala Gln Arg Ala Phe Arg
    50                  55                  60
```

-continued

Glu Arg Lys Glu Arg Lys Met Lys Glu Leu Glu Lys Val His Ala
 65                  70                  75                  80

Leu Glu Glu Met Asn Gln Gln Ser Leu Val Glu Thr Glu Phe Leu Arg
                 85                  90                  95

Ser Gln Leu Val Thr Leu Val Asn Glu Leu Lys Lys Tyr Arg Pro Gln
            100                 105                 110

Asn Gln Ala Asp Ser Gln Val Leu Glu Tyr Leu Ala Lys Thr Glu Asn
        115                 120                 125

Asp Asn Asp Ala Ala Gly Gln Thr Arg Gln Glu Leu Asn Ser Lys
    130                 135                 140

Glu Leu Gln Glu Ser Val Arg Arg Lys Met Ser Phe Thr Phe Ala Phe
145                 150                 155                 160

Pro Trp Lys Asn Glu Ile Lys Ser Glu Lys Ala Gly Ser Pro Ala
                165                 170                 175

Ala Thr Glu Gln Pro Arg Asn Asp Asn Leu Gln Phe Pro Ser Pro Gly
            180                 185                 190

Ser Ser Ser Lys Ser Ser Ser Val Ser Thr Ser Ser Leu Ser Lys
        195                 200                 205

Lys Lys Ile Gly Leu Tyr Thr Pro Gly Thr Thr Asp Ser Asn Ala Asn
    210                 215                 220

Asn Asn Asn Leu Ser Ser Ser Thr Ser Asn Leu Asn Asn Gly Ser Phe
225                 230                 235                 240

Thr Pro Gly Ser Ser Thr Gly Trp Met Asp Asn Val Phe Tyr Asn
                245                 250                 255

Asp Asp Ala Gln Gln Leu Pro Gln Phe Tyr Gln Ser Ala Thr Asp Asn
            260                 265                 270

Ser Gly Thr Thr Asn Asn Lys Leu Leu Glu Asp Asn Thr Ser Val Pro
        275                 280                 285

Tyr Gly Tyr Asp Ser Val Thr Phe Ser Asn Gln Phe Asn Phe Asp Asp
    290                 295                 300

Gln Phe Asp Glu Gln Val Ser Glu Phe Cys Ala Lys Leu Gly Gln Val
305                 310                 315                 320

Cys Gly Thr Lys Asp Cys Pro Val Pro Lys Gln Lys Thr Ala Ser Ser
                325                 330                 335

Thr Pro Asn Ile Thr Asn Ser Pro Leu Val Leu Ser Asn Thr Trp Gly
            340                 345                 350

Ser Pro Ser Lys His Gln Gly Glu Lys Ile Val Thr Thr Val Ser Ala
        355                 360                 365

Pro Ala Pro Ser Asp Lys Thr Ala Ala Ala Glu Gly Lys Asp Ala Gly
    370                 375                 380

Thr Thr Lys Ser Gly Glu Leu Pro Phe Ile Asp Thr Ser Leu Ala Phe
385                 390                 395                 400

Pro Glu Glu Gln Asp Leu Phe Arg Asp Ser Gln Pro Asp Asn Leu Phe
                405                 410                 415

Ala Glu Phe Ile Glu Asp Glu Pro Glu Arg Asp Asp Pro Phe Leu
            420                 425                 430

Ala Ala Asn Leu Ile Asn Glu Glu Pro Gln Gly Pro Gln Gln Asn
        435                 440                 445

Ile Gln Pro Gln Lys His Glu Gln Asp Gln Ile Gln Thr Gln Gln
    450                 455                 460

Arg Gln Gln Gln Asp Ala Lys Gln His Gln Ala Thr Asp Val Ala Asp
465                 470                 475                 480

```
Cys Asp Gly Val Val Pro Ser Arg Asp Gly Lys Leu Leu Lys Cys Ser
                485                 490                 495

Glu Val Trp Asp Arg Ile Thr Ser His Pro Lys Tyr Thr Asp Met Asp
            500                 505                 510

Ile Asp Gly Leu Cys Leu Glu Leu Met Ala Lys Ala Lys Cys Ser Glu
            515                 520                 525

Lys Gly Val Val Val Gln Ala Glu Asp Val Gln Arg Ala Leu Ala Asn
            530                 535                 540

Arg Leu Asp
545

<210> SEQ ID NO 18
<211> LENGTH: 552
<212> TYPE: PRT
<213> ORGANISM: Schizosaccharomyces pombe

<400> SEQUENCE: 18

Met Ser Gly Gln Thr Glu Thr Leu Ser Ser Thr Ser Asn Ile Pro Ile
1               5                   10                  15

Ala Lys Ala Glu Pro Glu Gln Ser Ala Asp Phe Ser Ala Ser His Lys
            20                  25                  30

Lys Arg Gly Pro Val Ser Asp Arg Ser Ser Arg Arg Thr Ser Ser Glu
        35                  40                  45

Glu Val Asp Leu Met Pro Asn Val Asp Glu Val Asp Gly Asp Val
    50                  55                  60

Lys Pro Lys Lys Ile Gly Arg Lys Asn Ser Asp Gln Glu Pro Ser Ser
65                  70                  75                  80

Lys Arg Lys Ala Gln Asn Arg Ala Ala Gln Arg Ala Phe Arg Lys Arg
                85                  90                  95

Lys Glu Asp His Leu Lys Ala Leu Glu Thr Gln Val Val Thr Leu Lys
            100                 105                 110

Glu Leu His Ser Ser Thr Thr Leu Glu Asn Asp Gln Leu Arg Gln Lys
            115                 120                 125

Val Arg Gln Leu Glu Glu Glu Leu Arg Ile Leu Lys Asp Gly Ser Phe
        130                 135                 140

Thr Phe Glu Met Ser Leu Pro His Arg Asn Pro Ser Leu Ser Ser Leu
145                 150                 155                 160

Pro Thr Thr Gly Phe Ser Ser Asn Phe Ala His Met Lys Asp Gly Ile
                165                 170                 175

Ser Pro Gln Ser Asn Leu His Leu Ser Pro Asn Ser Ile Glu Lys Pro
            180                 185                 190

Asn Met His Gln Asn Val Leu His Asn Asp Arg Ser Ala Asp Asn Leu
        195                 200                 205

Asn His Arg Tyr Gln Val Pro Pro Thr Leu Val Asp Ser Asn Ser Ala
    210                 215                 220

Gln Gly Thr Leu Ser Pro Glu Thr Pro Ser Ser Ser Asp Ser Pro Ser
225                 230                 235                 240

Asn Leu Tyr Leu Asn Tyr Pro Lys Arg Lys Ser Ile Thr His Leu His
                245                 250                 255

His Asp Cys Ser Ala Leu Ser Asn Gly Glu Asn Gly Glu Asp Val Ala
            260                 265                 270

Asp Gly Lys Gln Phe Cys Gln Lys Leu Ser Thr Ala Cys Gly Ser Ile
        275                 280                 285

Ala Cys Ser Met Leu Thr Lys Thr Thr Pro His Arg Ala Ser Val Asp
    290                 295                 300
```

Ile Leu Ser Asn Leu His Glu Ser Thr Val Ser Pro Pro Met Ala Asp
305                 310                 315                 320

Glu Ser Val Gln Arg Ser Ser Glu Val Ser Lys Ser Ile Pro Asn Val
            325                 330                 335

Glu Leu Ser Leu Asn Val Asn Gln Gln Phe Val Ser Pro Phe Gly Gly
            340                 345                 350

Thr Asp Ser Phe Pro Leu Pro Thr Asp Thr Gly Leu Asp Ser Leu Phe
            355                 360                 365

Glu Pro Asp Ser Ala Ile Glu Asn Ser His Leu Lys Asn Val Val Met
370                 375                 380

Glu Pro Glu Leu Phe Gln Ala Trp Arg Glu Pro Ala Glu Ser Leu Asp
385                 390                 395                 400

Lys Glu Phe Phe Asn Asp Glu Gly Ile Asp Asp Val Phe His Asn
                405                 410                 415

Tyr Phe His Asn Ser Asn Glu Asn Gly Asp Leu Ile Thr Asn Ser Leu
                420                 425                 430

His Gly Leu Asp Phe Leu Glu Asn Ala Asn Glu Ser Phe Pro Glu Gln
            435                 440                 445

Met Tyr Pro Phe Ile Lys His Asn Lys Asp Tyr Ile Ser Asn His Pro
450                 455                 460

Asp Glu Val Pro Pro Asp Gly Leu Pro Gln Lys Gly Lys His Asp Thr
465                 470                 475                 480

Ser Ser Gln Met Pro Ser Glu Asn Glu Ile Val Pro Ala Lys Glu Arg
                485                 490                 495

Ala Tyr Leu Ser Cys Pro Lys Val Trp Ser Lys Ile Ile Asn His Pro
            500                 505                 510

Arg Phe Glu Ser Phe Asp Ile Asp Asp Leu Cys Ser Lys Leu Lys Asn
            515                 520                 525

Lys Ala Lys Cys Ser Ser Gly Val Leu Leu Asp Glu Arg Asp Val
530                 535                 540

Glu Ala Ala Leu Asn Gln Phe Asn
545                 550

<210> SEQ ID NO 19
<211> LENGTH: 494
<212> TYPE: PRT
<213> ORGANISM: Schizosaccharomyces pombe

<400> SEQUENCE: 19

Met Ser Ser Val Pro Pro Leu Tyr Glu Asn Ala Leu Asp Leu Ile Gly
1               5                   10                  15

Asn Thr Pro Leu Ile Lys Leu Asn Lys Ile Pro Gln Ser Tyr Gly Ile
            20                  25                  30

Lys Ala Lys Val Tyr Ala Lys Val Glu Leu Phe Asn Ala Gly Gly Ser
        35                  40                  45

Ile Lys Asp Arg Ile Ser Lys Asn Met Ile Leu Glu Ala Glu Lys Ser
    50                  55                  60

Gly Arg Ile Lys Pro Gly Tyr Thr Leu Ile Glu Pro Thr Ser Gly Asn
65                  70                  75                  80

Thr Gly Ile Gly Leu Ala Leu Val Ala Ala Val Lys Gly Tyr Arg Thr
                85                  90                  95

Ile Ile Thr Leu Pro Glu Lys Met Ser Asn Glu Lys Val Ser Val Leu
            100                 105                 110

Lys Ala Leu Gly Ala Glu Ile Ile Arg Thr Pro Thr Glu Ala Ala Trp
        115                 120                 125

```
Asp Ala Pro Glu Ser His Ile Gly Val Ala Lys Lys Leu Glu Lys Glu
        130                 135                 140

Ile Pro Asn Ser Val Ile Leu Asp Gln Tyr Ser Asn Pro Ala Asn Pro
145                 150                 155                 160

Asp Ala His Tyr Tyr Gly Thr Gly Phe Glu Ile Trp Glu Gln Thr Lys
                165                 170                 175

Gly Lys Val Thr His Leu Val Ala Gly Ala Gly Thr Gly Gly Thr Ile
            180                 185                 190

Thr Gly Ile Ser Arg Tyr Leu Lys Glu Lys Asn Pro Lys Val Glu Val
        195                 200                 205

Thr Gly Ala Asp Pro Lys Gly Ser Ile Leu Ala Gln Pro Glu Ser Leu
    210                 215                 220

Asn Thr Ser Thr Glu Gly Tyr Leu Val Glu Gly Ile Gly Tyr Asp Phe
225                 230                 235                 240

Ile Pro Asp Val Leu Asn Arg Lys Tyr Val Asp Asn Trp Ile Lys Thr
                245                 250                 255

Glu Asp Ala Glu Ser Phe Lys Leu Ala Arg Arg Ile Ile Arg Glu Glu
            260                 265                 270

Gly Ile Leu Val Gly Gly Ser Gly Ser Ala Leu Gln Ala Ala Leu
        275                 280                 285

Gln Val Ala Lys Asp Leu Thr Glu Asp Val Val Val Val Phe
    290                 295                 300

Pro Asp Ser Ile Arg Ser Tyr Leu Ser Lys Phe Ala Asp Asp Glu Trp
305                 310                 315                 320

Met Lys Ile Asn Asn Phe Ala Val Asp Glu Thr Ser Ser Ser Gly Asn
                325                 330                 335

Lys Ser Asp Asp Phe Leu Ala Ser Lys Thr Ile Arg Asp Leu Val Ala
            340                 345                 350

Gly Lys Ala Pro Val Val Thr Val Thr Leu Ser Asp Thr Val Gly Lys
        355                 360                 365

Thr Phe Asp Leu Leu His Asp Asn Gly Phe Asp Gln Leu Pro Val Leu
    370                 375                 380

Asn Asn Ser Gly Lys Leu Val Gly Leu Val Thr Leu Ser Lys Ile Leu
385                 390                 395                 400

Lys Ser Leu Ser Thr Lys Lys Val Gln Leu Thr Asn Ser Ile Ala Ser
                405                 410                 415

Val Ile Ile Asp Phe Arg Lys Leu Ala Asp Phe Glu Lys Ser Phe Thr
            420                 425                 430

Ile Ala Lys Glu Ser Gly Phe Thr Lys Arg Ser Tyr Glu Pro Ile Thr
        435                 440                 445

Leu Asp Thr Pro Leu Ala Leu Leu Asn Lys Phe Phe Glu Thr Asn Ser
    450                 455                 460

Asn Ala Ile Ile Thr Asp Asp Glu Leu Lys Pro Val Gln Ile Val Thr
465                 470                 475                 480

Lys Val Asp Leu Ile Ser Phe Leu Thr Lys Asn Val Ala Phe
                485                 490

<210> SEQ ID NO 20
<211> LENGTH: 493
<212> TYPE: PRT
<213> ORGANISM: Kluyveromyces lactis
```

<400> SEQUENCE: 20

```
Met Gly Tyr Asp Thr Arg His Asp Val Ile Asp Leu Val Gly Asn Thr
1               5                   10                  15

Pro Leu Ile Arg Leu Gln Lys Leu Pro Lys Ala Ile Gly Ile Lys Pro
            20                  25                  30

Lys Val Tyr Ala Lys Leu Glu Leu Tyr Asn Pro Gly Gly Ser Ile Lys
        35                  40                  45

Asp Arg Ile Ala Lys Ser Met Ile Glu Ala Ala Glu Glu Gly Ile
    50                  55                  60

Ile His Pro Ser Arg Ser Thr Leu Ile Glu Pro Thr Ser Gly Asn Thr
65                  70                  75                  80

Gly Ile Gly Leu Ala Leu Ile Gly Ala Ile Lys Gly Tyr Arg Thr Ile
                85                  90                  95

Ile Thr Leu Pro Glu Lys Met Ser Asn Glu Lys Val Ser Val Leu Lys
            100                 105                 110

Ala Leu Gly Ala Glu Ile Ile Arg Thr Pro Thr Ala Ala Ala Trp Asp
            115                 120                 125

Ser Pro Glu Ser His Ile Gly Val Ala Leu Arg Leu Glu Lys Glu Ile
    130                 135                 140

Pro Gly Gly Ile Ile Leu Asp Gln Tyr Asn Asn Met Lys Asn Pro Glu
145                 150                 155                 160

Ala His Tyr Phe Gly Thr Gly Lys Glu Ile His His Gln Leu Glu Asp
                165                 170                 175

Leu Ser Leu Phe Ser Lys Leu Lys Ala Val Val Ala Gly Ala Gly Thr
            180                 185                 190

Gly Gly Thr Ile Ser Gly Ile Ser Lys Tyr Ile Lys Glu Gln Asn Asp
            195                 200                 205

Lys Ile Ala Ile Val Gly Ala Asp Pro Val Gly Ser Ile Leu Ala Val
    210                 215                 220

Pro Glu Lys Leu Asn Glu Thr Asp Val Thr Glu Tyr Lys Val Glu Gly
225                 230                 235                 240

Ile Gly Tyr Asp Phe Val Pro Lys Val Leu Asn Arg Asp Ser Val Asp
                245                 250                 255

His Trp Val Lys Thr Asp Asp Lys Ser Ser Phe Lys Tyr Ala Arg Gln
            260                 265                 270

Leu Ile Ser Asn Glu Gly Val Leu Val Gly Ser Ser Gly Ser Ala
            275                 280                 285

Phe Thr Ala Leu Val Asp Tyr Cys Asn Glu His Pro Glu Leu Thr Glu
    290                 295                 300

Asp Asp Val Ile Val Val Ile Phe Pro Asp Ser Val Arg Ser Tyr Leu
305                 310                 315                 320

Thr Lys Phe Val Asp Asp Glu Trp Leu Lys Thr Asn Gly Leu Trp Asp
                325                 330                 335

Asp Ala Ile Ala Thr Pro Ile Val Gln Lys Glu Thr Asp Val Phe Glu
            340                 345                 350

Asp Ala Thr Val Lys Asp Leu Asn Leu Lys Pro Val Val Ser Val Glu
            355                 360                 365

Glu Asp Ala Ser Val Ala Thr Val Ile Lys Ile Leu Arg Asp Asn Ser
    370                 375                 380

Phe Asp Gln Leu Pro Val Leu Thr Lys Asp Gly Lys Leu Cys Gly Leu
385                 390                 395                 400

Val Thr Leu Ser Gln Leu Leu Lys Lys Leu Ser Thr Ser Lys Asp Val
                405                 410                 415
```

```
Ser Ser Ile Lys Ser Leu Phe Phe Asp Phe Arg Lys Leu Asn Asn Phe
            420                 425                 430

Asp Asp Ile Ser Ser Tyr Asn Ala Asp Lys Ser His Lys Lys Ile Phe
            435                 440                 445

Val Arg Phe Asp Val Asn Thr Thr Leu Ser Glu Leu Asn Ser Phe Phe
450                 455                 460

Glu Lys Asn Ser Ala Ala Ile Ile Thr Glu Gly Leu Asn Pro Val His
465                 470                 475                 480

Ile Val Thr Lys Val Asp Leu Leu Ser Tyr Leu Ala Lys
                485                 490

<210> SEQ ID NO 21
<211> LENGTH: 583
<212> TYPE: PRT
<213> ORGANISM: Kluyveromyces lactis

<400> SEQUENCE: 21

Met Ser Thr Ser Thr Ala Lys Arg Pro Phe Asp Asn Lys Arg Ala Gly
1               5                   10                  15

Ser Pro Asp Asp Gly Thr Asp Ser Asp Ser Gly Gly Asn Asn Ser Gly
            20                  25                  30

Ser Ser Pro Ala Ser Lys Arg Glu Arg Lys Pro Gly Arg Lys Pro
            35                  40                  45

Leu Glu Thr Glu Ala Lys Asp Lys Arg Thr Ala Gln Asn Arg Ala Ala
50                  55                  60

Gln Arg Ala Phe Arg Glu Arg Arg Glu Arg Lys Met Lys Glu Leu Glu
65                  70                  75                  80

Asp Lys Val Ser Gln Leu Glu Ser Leu Asn Lys Gln Ser Glu Leu Glu
                85                  90                  95

Thr Lys Phe Leu Arg Asn Gln Val Thr Asn Leu Leu Ser Glu Leu Lys
            100                 105                 110

Arg Tyr Asn Pro Glu Leu Pro Lys Lys Arg Asp Ser Ile Leu Leu Asp
            115                 120                 125

Tyr Leu Ala Lys Gln Arg Lys Ala Ser Ile Asp Ser Asn Pro Asp Phe
130                 135                 140

Ser Ala Ala Ala Asn Lys Ala Ala Asn Ser Lys Asp Ser Ser Thr Ala
145                 150                 155                 160

Ile Ser Ser Asn Phe Gln Phe Glu Phe Pro Trp Lys Met Asp Pro
                165                 170                 175

Ser Lys Ile Pro Ser Pro Ser Ser Asp Ser Thr Ser Pro Ser Ala Ser
            180                 185                 190

Thr Ser Ile Leu Asp Asn Ala Asn Asn Lys Ser Val Ser Ser Thr Asn
            195                 200                 205

Leu Asn His Ser Arg Ser Ser Ile Ser Asn Ser Ser Ser Pro Ser
            210                 215                 220

Asn Val Asn Gly Leu Ser Ser Arg Lys His Ser Asn Thr Leu Asn Leu
225                 230                 235                 240

Tyr Gln Thr Gln Ser Asn Val Thr Ser Glu Phe Asp Phe Asp Ser Gln
                245                 250                 255

Phe Asp Glu Ser Val Ser Ser Phe Cys Ser Lys Leu Ser Met Ala Cys
            260                 265                 270

Gly Thr Lys Ser Asn Pro Ile Pro Lys Ala Ser Pro Val Ser Thr Pro
            275                 280                 285

Ser Ser Ser Asp Leu Leu Lys Pro Lys Ser Asn Ser Asn Val Asn Ile
            290                 295                 300
```

-continued

```
Thr Asn His Asn Asn Asn Lys Ile Asn Ser Lys Asp Leu Ser Ser Ser
305                 310                 315                 320

Ala Pro Leu His Asp Ser Ala Ser Ala Leu Asn Asn His Asp
            325                 330                 335

Ser Val Asn Ala Val Ser Asn Gln Phe Ser Val Asp Lys Gln Tyr Asn
        340                 345                 350

Asp Ser Ser His Ser Gln Ala Thr Pro Asn Gly Leu Asp Asn Asp Ser
            355                 360                 365

Ser Val Ser Ala Trp Gln Gln Pro Ser Phe Gly Gln Leu Gly Phe Arg
    370                 375                 380

Thr Asp Gln Leu Phe Asp Leu Asp Leu Asp Ser Ala Ser Pro Ile Thr
385                 390                 395                 400

Lys Gln Lys Asp Asn Asn Tyr Ser Thr Thr Thr Asn Asn Thr Asn Ser
                405                 410                 415

Pro Ala Lys Ala Asp Gly Met Tyr Trp Asn Phe Asn Thr Pro Leu Ser
            420                 425                 430

Asn Met Val Ser Arg Asn Met Gln Asn Pro Glu Ile Pro Phe Ile Asp
        435                 440                 445

Thr Gly Leu Ala Phe Pro Asp Tyr Asp Asp Pro Leu Leu Asp Ile Leu
    450                 455                 460

Lys Glu Glu Gln Glu Asn Glu Gln Val Glu Gly Asp Ser Asp Pro Ile
465                 470                 475                 480

Gln Ala Leu Ile Asn Glu Glu Pro Ser Met Pro Leu Cys His Asp Pro
                485                 490                 495

Ala Ala Asn Ala Gly Ala Ser Val Ser Glu Thr Asp Lys Leu Ser Asn
            500                 505                 510

Gln Glu Glu Ile Val Gln Asp Ile Ile Pro Ser Asn Asp Gly Lys Leu
        515                 520                 525

Leu Lys Cys Ser Glu Val Trp Asp Arg Ile Thr Ala His Pro Arg Tyr
    530                 535                 540

Ser Asp Leu Asp Ile Asp Gly Leu Cys Leu Glu Leu Arg Thr Lys Ala
545                 550                 555                 560

Lys Cys Ser Glu Lys Gly Val Val Val Asn Ala Glu Asp Val Gln Lys
                565                 570                 575

Ala Leu Ile Ser His Met Gln
            580

<210> SEQ ID NO 22
<211> LENGTH: 501
<212> TYPE: PRT
<213> ORGANISM: Pichia pastoris

<400> SEQUENCE: 22

Met Ser Asp Asn Asn Gln Pro Leu Pro Pro Val Ser Asn Ser Ile Leu
1               5                   10                  15

Glu His Ile Gly Lys Thr Pro Leu Val Lys Leu Asn Arg Ile Pro Lys
                20                  25                  30

Ile Leu Asn Leu Lys Pro Gln Val Tyr Ala Lys Val Glu Leu Phe Asn
            35                  40                  45

Ser Gly Gly Ser Ile Lys Asp Arg Ile Ala Leu Arg Met Val Glu Gln
        50                  55                  60

Ala Glu Lys Glu Gly Arg Ile Lys Pro Gly Tyr Thr Leu Ile Glu Pro
65                  70                  75                  80

Thr Ser Gly Asn Thr Gly Ile Gly Leu Ala Leu Val Gly Ala Val Lys
                85                  90                  95
```

```
Gly Tyr Arg Thr Ile Ile Thr Leu Pro Glu Lys Met Ser Asn Glu Lys
                100                 105                 110

Val Ala Val Leu Lys Ala Leu Gly Ala Glu Ile Ile Arg Thr Pro Thr
            115                 120                 125

Glu Ala Ala Trp Asp Ser Pro Glu Ser His Ile Gly Val Ala Arg Arg
        130                 135                 140

Leu Glu Lys Glu Ile Pro Asn Ala Val Ile Leu Asp Gln Tyr Gly Asn
145                 150                 155                 160

Val Asn Asn Pro Asp Ala His Phe Tyr Thr Thr Gly Ala Glu Ile Trp
                165                 170                 175

Asp Gln Thr Asn Gly Lys Val Thr His Val Val Ala Gly Ala Gly Thr
            180                 185                 190

Gly Gly Thr Ile Thr Gly Ile Ala Lys Phe Leu Lys Ser Lys Asn Pro
        195                 200                 205

Asn Ile Gln Ile Ile Gly Ala Asp Pro His Gly Ser Ile Leu Ala Leu
210                 215                 220

Pro Glu Ser Leu Asn Thr Ser Asn Glu Gln Tyr Lys Val Glu Gly Ile
225                 230                 235                 240

Gly Tyr Asp Phe Ile Pro Glu Val Leu Asp Arg Glu Ile Val Asp Thr
                245                 250                 255

Trp Tyr Lys Thr Asp Asp Lys Asp Ser Phe Lys Leu Ala Arg Gln Leu
            260                 265                 270

Ile Ser Glu Glu Gly Ile Leu Val Gly Gly Ser Ser Gly Ser Ala Leu
        275                 280                 285

Ser Ala Ala Val Lys Ile Ile Asn Asp Ala Lys Leu Asp Glu Ser Ala
290                 295                 300

Val Val Val Val Val Cys Pro Asp Ser Ile Arg Ser Tyr Leu Thr Lys
305                 310                 315                 320

Phe Ala Asp Asp Asp Trp Met Lys Leu Asn Gly Phe Thr Glu Asp Glu
                325                 330                 335

Pro Ala Pro Leu Lys Arg Lys Ser Ser Phe Ser Lys Asp Thr Leu Ser
            340                 345                 350

Ser Tyr Thr Ile Lys Asp Leu Ala Leu Lys Pro Val Val Ser Val Thr
        355                 360                 365

Ile Asp Asp Ser Ile Glu Ser Thr Ile Asn Ile Leu Gln Thr Lys Gly
370                 375                 380

Phe Asp Gln Leu Pro Val Leu Lys Asn Asp Lys Leu Ala Gly Ile Val
385                 390                 395                 400

Thr Leu Ser Gln Leu Leu Arg Leu Leu Ser Asn Lys Lys Ile His Leu
                405                 410                 415

Thr Ser Lys Val Glu Ser Ala Tyr Phe Asp Phe Ser Lys Leu Glu Asn
            420                 425                 430

Phe Glu Lys Ser Tyr Asn Ile Asn Lys Glu Ser Thr Asn Lys Arg Arg
        435                 440                 445

Glu Tyr Gln Lys Ile Thr Thr Ser Thr Thr Leu Ala Lys Leu Asn Lys
450                 455                 460

Phe Phe Glu Thr Ser Ser Ala Ala Ile Val Glu Asn Asp Lys Gly Gln
465                 470                 475                 480

Pro Ile His Ile Val Ser Lys Val Asp Leu Leu Ser Phe Leu Ala Ser
                485                 490                 495

Lys Gly Glu Phe Asn
            500
```

<210> SEQ ID NO 23
<211> LENGTH: 461
<212> TYPE: PRT
<213> ORGANISM: Pichia pastoris

<400> SEQUENCE: 23

```
Met Ser Asp Val Val Asn Lys Arg Ala Ala Thr Ser Ser Thr Gln Thr
1               5                   10                  15

Asn Lys Arg Gln Glu Leu Ser Ser Ala Leu Thr Lys Pro Gly Arg Lys
            20                  25                  30

Pro Val Gln Thr Glu Pro Lys Asp Lys Arg Thr Ala Gln Asn Arg Ala
        35                  40                  45

Ala Gln Arg Ala Phe Arg Glu Arg Lys Glu Lys Lys Met Lys Glu Leu
    50                  55                  60

Glu Thr Lys Val Glu Glu Leu Glu Arg Gln Lys Ser Gln Leu Asn Thr
65                  70                  75                  80

Glu Ser Glu Phe Leu Arg Ser Gln Val Glu Thr Leu Ile His Glu Leu
                85                  90                  95

Ser Lys Tyr Arg Gly Glu Thr Asp Val Leu Ser Leu Leu Pro Thr Ser
            100                 105                 110

Ile Pro Gln Glu Ser Lys Lys Met Val Arg Thr Pro Ser Ser Asn Thr
        115                 120                 125

Thr Asn Ser Ser Ser Val Gly Val Thr Pro Ser Ser Ser Thr Leu Arg
130                 135                 140

Ser Ser Ser Ser Gly Val Tyr Glu Phe Pro Trp Lys Leu Ser Asn
145                 150                 155                 160

Ser Gln Asn Pro Ser Gly Ser Asn Ser Pro Leu Asp Leu Thr Lys Ala
                165                 170                 175

Gly Gln Leu Pro Ser Pro Thr Ser Ile Asn Gln Asn Pro Gly Leu Thr
            180                 185                 190

Ala Glu Ser Val Lys Ser Ser Val Ser Ser Glu Ser Pro Asn Ser
        195                 200                 205

Asn Ile Glu Asp Phe Leu Asn Ser Arg Asn Ser Asn Phe Asp Asn Arg
    210                 215                 220

Phe Asp Glu Ser Val Asp Gly Phe Cys Ser Asn Leu Gly Gln Ala Cys
225                 230                 235                 240

Gly Asn Lys Asp Ile Pro Leu Pro Lys Glu Thr Ser Ser Ile Arg Asn
                245                 250                 255

Pro Gly Val Ile Asp Ser Leu Ser Asn Phe Ser Asn Ser Asp Ile
            260                 265                 270

Gln Thr Leu Phe Ser Pro Asn Ser Leu Gln Asn Asp Pro Leu Ala Glu
        275                 280                 285

Phe Asp Pro Thr Pro Ile Asp Gln Asn Leu Val Phe Gly Leu Asn Ala
    290                 295                 300

Pro Glu Thr Asn Leu Asp Gly Leu Phe Gly Asp Phe Asn Lys Tyr His
305                 310                 315                 320

Thr Asp Pro Leu Ala Ser Leu Val Thr Glu Glu Ser Ile Phe Asp Pro
                325                 330                 335

Leu Arg Ala Thr Ser Asn Ser Val Ser His Ser Lys Pro Asn Pro Ile
            340                 345                 350

Thr Thr Thr Ser Leu His Asn Leu Glu Ala Lys His Lys Val Pro Glu
        355                 360                 365

Ala Asp Glu Asp Cys Asn Asp Asn Leu Asp Asn Met Val Val Pro Asn
    370                 375                 380
```

```
Arg Glu Gly Ser Leu Leu Lys Cys Ser Glu Ile Trp Glu Arg Ile Thr
385                 390                 395                 400

Thr His Pro Arg Tyr Ser Glu Ile Asp Ile Asp Gly Leu Cys Met Glu
            405                 410                 415

Leu Lys His Lys Ala Lys Cys Ser Glu Ser Gly Val Val Asp Asp
            420                 425                 430

Ala Asp Val Asp Ser Leu Leu Gln Arg Ala Ala Leu Lys Tyr Pro Ile
            435                 440                 445

Lys Thr Glu Pro Asp Val Val Asp Phe Ser Met Phe Lys
            450                 455                 460

<210> SEQ ID NO 24
<211> LENGTH: 387
<212> TYPE: PRT
<213> ORGANISM: Saccharomyces cerevisiae

<400> SEQUENCE: 24

Met Thr Glu Phe Glu Leu Pro Pro Lys Tyr Ile Thr Ala Ala Asn Asp
1               5                   10                  15

Leu Arg Ser Asp Thr Phe Thr Thr Pro Thr Ala Glu Met Ile Gln Ala
            20                  25                  30

Ala Leu Glu Ala Ser Ile Gly Asp Ala Val Tyr Gly Glu Asp Val Asp
        35                  40                  45

Thr Val Arg Leu Glu Gln Thr Val Ala Arg Met Ala Gly Lys Glu Ala
    50                  55                  60

Gly Leu Phe Cys Val Ser Gly Thr Leu Ser Asn Gln Ile Ala Ile Arg
65                  70                  75                  80

Thr His Leu Met Gln Pro Pro Tyr Ser Ile Leu Cys Asp Tyr Arg Ala
                85                  90                  95

His Val Tyr Thr His Glu Ala Ala Gly Leu Ala Ile Leu Ser Gln Ala
            100                 105                 110

Met Val Val Pro Val Val Pro Ser Asn Gly Asp Tyr Leu Thr Leu Glu
        115                 120                 125

Asp Ile Lys Ser His Tyr Val Pro Asp Asp Gly Asp Ile His Gly Ala
    130                 135                 140

Pro Thr Arg Leu Ile Ser Leu Glu Asn Thr Leu His Gly Ile Val Tyr
145                 150                 155                 160

Pro Leu Glu Glu Leu Val Arg Ile Lys Ala Trp Cys Met Glu Asn Gly
                165                 170                 175

Leu Lys Leu His Cys Asp Gly Ala Arg Ile Trp Asn Ala Ala Ala Gln
            180                 185                 190

Ser Gly Val Pro Leu Lys Gln Tyr Gly Glu Ile Phe Asp Ser Ile Ser
        195                 200                 205

Ile Cys Leu Ser Lys Ser Met Gly Ala Pro Ile Gly Ser Val Leu Val
    210                 215                 220

Gly Asn Leu Lys Phe Val Lys Lys Ala Thr His Phe Arg Lys Gln Gln
225                 230                 235                 240

Gly Gly Gly Ile Arg Gln Ser Gly Met Met Ala Arg Met Ala Leu Val
                245                 250                 255

Asn Ile Asn Asn Asp Trp Lys Ser Gln Leu Leu Tyr Ser His Ser Leu
            260                 265                 270

Ala His Glu Leu Ala Glu Tyr Cys Glu Ala Lys Gly Ile Pro Leu Glu
        275                 280                 285

Ser Pro Ala Asp Thr Asn Phe Val Phe Ile Asn Leu Lys Ala Ala Arg
    290                 295                 300
```

Met Asp Pro Asp Val Leu Val Lys Lys Gly Leu Lys Tyr Asn Val Lys
305                 310                 315                 320

Leu Met Gly Gly Arg Val Ser Phe His Tyr Gln Val Thr Arg Asp Thr
            325                 330                 335

Leu Glu Lys Val Lys Leu Ala Ile Ser Glu Ala Phe Asp Tyr Ala Lys
            340                 345                 350

Glu His Pro Phe Asp Cys Asn Gly Pro Thr Gln Ile Tyr Arg Ser Glu
            355                 360                 365

Ser Thr Glu Val Asp Val Asp Gly Asn Ala Ile Arg Glu Ile Lys Thr
            370                 375                 380

Tyr Lys Tyr
385

<210> SEQ ID NO 25
<211> LENGTH: 387
<212> TYPE: PRT
<213> ORGANISM: Saccharomyces bayanus

<400> SEQUENCE: 25

Met Thr Glu Phe Glu Leu Pro Pro Lys Tyr Ile Thr Ala Ala Asn Asp
1               5                   10                  15

Leu Arg Ser Asp Thr Phe Thr Thr Pro Thr Ala Glu Met Met Gln Ala
            20                  25                  30

Ala Leu Glu Ala Ser Ile Gly Asp Ala Val Tyr Gly Glu Asp Val Asp
            35                  40                  45

Thr Val Arg Leu Glu Gln Thr Val Ala Arg Met Ala Gly Lys Glu Ala
        50                  55                  60

Gly Leu Phe Cys Val Ser Gly Thr Leu Ser Asn Gln Ile Ala Ile Arg
65                  70                  75                  80

Thr His Leu Met Gln Pro Pro Tyr Ser Ile Leu Cys Asp Tyr Arg Ala
                85                  90                  95

His Val Tyr Thr His Glu Ala Ala Gly Leu Ala Ile Leu Ser Gln Ala
            100                 105                 110

Met Val Val Pro Val Val Pro Ser Asn Gly Asp Tyr Leu Thr Leu Glu
            115                 120                 125

Asp Ile Lys Ser His Tyr Val Pro Asp Asp Gly Asp Ile His Gly Ala
        130                 135                 140

Pro Thr Arg Leu Ile Ser Leu Glu Asn Thr Leu His Gly Ile Val Tyr
145                 150                 155                 160

Pro Leu Glu Glu Leu Val Arg Ile Lys Ala Trp Cys Met Glu Asn Gly
                165                 170                 175

Leu Lys Leu His Cys Asp Gly Ala Arg Ile Trp Asn Ala Ala Ala Gln
            180                 185                 190

Ser Gly Val Pro Leu Lys Gln Tyr Gly Glu Ile Phe Asp Ser Ile Ser
            195                 200                 205

Ile Cys Leu Ser Lys Ser Met Gly Ala Pro Ile Gly Ser Val Leu Val
        210                 215                 220

Gly Asn Leu Lys Phe Val Lys Lys Ala Thr His Phe Arg Lys Gln Gln
225                 230                 235                 240

Gly Gly Gly Ile Arg Gln Ser Gly Met Met Ala Arg Met Ala Leu Val
                245                 250                 255

Asn Ile Asn Asn Asp Trp Lys Ser Gln Leu Leu Tyr Ser His Ser Leu
            260                 265                 270

Ala His Glu Leu Ala Glu Tyr Cys Glu Ala Lys Gly Ile Pro Leu Glu
            275                 280                 285

```
Ser Pro Ala Asp Thr Asn Phe Val Phe Ile Asn Leu Lys Ala Ala Arg
    290                 295                 300
Met Asp Pro Asp Val Leu Val Lys Lys Gly Leu Lys Tyr Asn Val Lys
305                 310                 315                 320
Leu Met Gly Gly Arg Val Ser Phe His Tyr Gln Val Thr Arg Asp Thr
                325                 330                 335
Leu Glu Lys Val Lys Leu Ala Ile Ser Glu Ala Phe Asp Tyr Ala Lys
                340                 345                 350
Glu His Pro Phe Asp Cys Asn Gly Pro Thr Gln Ile Tyr Arg Ser Glu
                355                 360                 365
Ser Thr Glu Val Asp Val Asp Gly Asn Ala Ile Arg Glu Ile Lys Thr
370                 375                 380
Tyr Lys Tyr
385

<210> SEQ ID NO 26
<211> LENGTH: 387
<212> TYPE: PRT
<213> ORGANISM: Saccharomyces kudriavzevii

<400> SEQUENCE: 26

Met Thr Glu Phe Glu Leu Pro Pro Lys Tyr Thr Ala Ala Asn Asp
1               5                   10                  15

Leu Arg Ser Asp Thr Phe Thr Thr Pro Thr Pro Glu Met Met Gln Ala
                20                  25                  30

Ala Leu Glu Ala Ser Ile Gly Asp Ala Val Tyr Gly Glu Asp Val Asp
                35                  40                  45

Thr Val Arg Leu Glu Gln Thr Val Ala Arg Met Ala Ala Lys Glu Ala
50                  55                  60

Gly Leu Phe Cys Val Ser Gly Thr Leu Ser Asn Gln Ile Ala Ile Arg
65                  70                  75                  80

Thr His Leu Thr Gln Pro Pro Tyr Ser Ile Leu Cys Asp Tyr Arg Ala
                85                  90                  95

His Val Tyr Thr His Glu Ala Ala Gly Leu Ala Ile Leu Ser Gln Ala
                100                 105                 110

Met Val Val Pro Val Ile Pro Ser Asn Gly Asp Tyr Leu Thr Leu Glu
                115                 120                 125

Asp Ile Arg Ser His Tyr Val Pro Asp Asp Gly Asp Ile His Gly Ala
                130                 135                 140

Pro Thr Arg Leu Ile Ser Leu Glu Asn Thr Leu His Gly Ile Val Tyr
145                 150                 155                 160

Pro Leu Glu Glu Leu Val Arg Ile Lys Ala Trp Cys Met Glu Asn Gly
                165                 170                 175

Leu Lys Leu His Cys Asp Gly Ala Arg Ile Trp Asn Ala Ala Ala Gln
                180                 185                 190

Ser Gly Val Pro Leu Lys Gln Tyr Gly Glu Ile Phe Asp Ser Ile Ser
                195                 200                 205

Ile Cys Leu Ser Lys Ser Met Gly Ala Pro Ile Gly Ser Val Leu Val
                210                 215                 220

Gly Asn Leu Lys Phe Val Lys Lys Ala Thr His Phe Arg Lys Gln Gln
225                 230                 235                 240

Gly Gly Gly Ile Arg Gln Ser Gly Met Met Ala Arg Met Ala Leu Val
                245                 250                 255

Asn Ile Asn Asn Asp Trp Lys Ser Gln Leu Leu Tyr Ser His Ser Leu
                260                 265                 270
```

Ala His Glu Leu Ala Gln Phe Cys Lys Ala Lys Gly Ile Pro Leu Glu
            275                 280                 285

Ser Pro Ala Asp Thr Asn Phe Val Phe Ile Asn Leu Lys Ser Ala Arg
290                 295                 300

Met Asp Pro Asp Val Leu Val Lys Lys Gly Leu Lys Tyr Asn Val Lys
305                 310                 315                 320

Leu Met Gly Gly Arg Val Ser Phe His Tyr Gln Ile Thr Arg Asp Thr
                325                 330                 335

Leu Glu Lys Val Lys Leu Ala Ile Ser Glu Ala Phe Asp Tyr Ala Lys
            340                 345                 350

Glu His Pro Phe Asp Ser Asn Gly Pro Thr Lys Ile Tyr Arg Ser Glu
            355                 360                 365

Ser Thr Glu Val Asp Val Asp Gly Asn Ala Ile His Glu Ile Lys Thr
370                 375                 380

Tyr Lys Tyr
385

<210> SEQ ID NO 27
<211> LENGTH: 371
<212> TYPE: PRT
<213> ORGANISM: Cyberlindnera jadinii

<400> SEQUENCE: 27

Met Thr Val Ala Glu Leu Lys Pro Tyr Gln Ser Ala Ser Asn Asp Phe
1               5                   10                  15

Arg Ser Asp Thr Phe Thr Thr Pro Thr Glu Ala Met Ile Lys Ala Ala
            20                  25                  30

Leu Thr Ala Ser Ile Gly Asp Ser Val Tyr Asn Glu Asp Val Asp Thr
        35                  40                  45

Ile Ala Leu Glu Gln Lys Val Ala Lys Leu Ala Gly Lys Pro Ala Gly
    50                  55                  60

Leu Tyr Cys Val Ser Gly Thr Leu Ser Asn Gln Ile Ala Ile Arg Thr
65                  70                  75                  80

His Leu Phe Gln Pro Pro Tyr Ser Ile Leu Cys Asp Tyr Arg Ala His
                85                  90                  95

Val Tyr Thr His Glu Ala Ala Gly Leu Ala Met Leu Ser Asn Ala Met
            100                 105                 110

Val Val Pro Val Arg Pro Ser Asn Gly Asp Tyr Leu Thr Leu Glu Asp
        115                 120                 125

Ile Lys Lys Asn Leu Val Pro Glu Asp Gly Asp Ile His Gly Ala Pro
    130                 135                 140

Thr Lys Leu Ile Ser Leu Glu Asn Thr Leu His Gly Ile Val Tyr Pro
145                 150                 155                 160

Tyr Glu Glu Leu Leu Arg Ile Lys Gln Phe Cys Val Glu Asn Gly Tyr
                165                 170                 175

Lys Leu His Cys Asp Gly Ala Arg Ile Trp Asn Ala Ser Val Glu Thr
            180                 185                 190

Gly Val Pro Leu His Lys Tyr Gly Glu Ile Phe Asp Ser Ile Ser Ile
        195                 200                 205

Cys Leu Ser Lys Ser Ile Gly Ala Pro Met Gly Ser Val Leu Val Gly
    210                 215                 220

Glu Leu Pro Phe Ile Lys Lys Cys Asn His Phe Lys Lys Gln Cys Gly
225                 230                 235                 240

Gly Gly Ile Arg Gln Ser Gly Met Met Ala Lys Met Ala Met Val Ala
                245                 250                 255

Ile Glu Asp Asn Leu Pro Leu Leu Lys Ser Ser His Glu Lys Ala Lys
            260                 265                 270

Asn Leu Gly Asp Phe Cys Ile Glu Asn Gly Ile Val Leu Glu Ser Pro
            275                 280                 285

Val Asp Thr Asn Phe Val Phe Ile Asp Leu Glu Ala Asn Tyr Ile Lys
            290                 295                 300

Asp Asp Asp Leu Ile Lys Phe Gly Lys Lys His Asn Val Asn Leu Met
305                 310                 315                 320

Gly Gly Arg Ile Ala Phe His Tyr Gln Ile Ser Asp Glu Ala Leu Glu
            325                 330                 335

Asn Val Lys Leu Ala Val Trp Asp Ala Phe Glu Asn Ala Lys Lys Asn
            340                 345                 350

Pro Tyr Val His Asp Gly Pro Tyr Lys Met Tyr Arg Ser Pro Thr Pro
            355                 360                 365

Val Lys Tyr
    370

<210> SEQ ID NO 28
<211> LENGTH: 387
<212> TYPE: PRT
<213> ORGANISM: Torulaspora delbrueckii

<400> SEQUENCE: 28

Met Thr Ser Gln Leu Pro Leu Ala Tyr Ala Ser Ala Ser Asn Asp Leu
1               5                   10                  15

Arg Ser Asp Thr Phe Thr Thr Pro Thr Pro Glu Met Ile Glu Ala Ala
            20                  25                  30

Leu Thr Ala Ser Ile Gly Asp Ala Val Tyr Gln Glu Asp Met Asp Thr
            35                  40                  45

Cys Phe Leu Glu Asn Leu Val Ala Asn Leu Ala Gly Lys Glu Gln Gly
50                  55                  60

Leu Phe Cys Val Ser Gly Thr Leu Ser Asn Gln Ile Ala Leu Arg Thr
65                  70                  75                  80

His Leu Leu Gln Pro Pro Tyr Ser Val Leu Cys Asp Tyr Arg Ala His
            85                  90                  95

Val Tyr Thr His Glu Ala Ala Gly Leu Ala Ile Leu Ser Gln Ala Met
            100                 105                 110

Val Val Pro Val Arg Pro Ala Asn Gly Asn Tyr Leu Thr Leu Asp Asp
            115                 120                 125

Ile Thr Ala His Tyr Val Pro Asp Asp Gly Asp Val His Gly Ala Pro
            130                 135                 140

Thr Lys Val Ile Ser Leu Glu Asn Thr Leu His Gly Met Ile Thr Pro
145                 150                 155                 160

Ile Asp Glu Leu Val Arg Ile Arg Ala Trp Cys Ser Gln Asn Asn Ile
            165                 170                 175

Lys Leu His Cys Asp Gly Ala Arg Ile Trp Asn Ala Ala Ile Ala Ser
            180                 185                 190

Gly Val Pro Leu Lys Gln Phe Gly Glu Leu Phe Asp Ser Ile Ser Ile
            195                 200                 205

Cys Leu Ser Lys Ser Met Gly Ala Pro Ile Gly Ser Ile Leu Val Gly
            210                 215                 220

Asp Ala Lys Phe Ile Lys Lys Ala Asn His Phe Arg Lys Gln Gln Gly
225                 230                 235                 240

Gly Gly Ile Arg Gln Ser Gly Met Met Ala Lys Met Ala Thr Val Ala
            245                 250                 255

```
Ile Asn Gly Asp Trp Lys Ala Lys Met Ser Tyr Ser His Arg Leu Ala
            260                 265                 270

Ser Asp Leu Ala Leu Phe Cys Lys Glu Asn Asp Ile Pro Leu Glu Ser
            275                 280                 285

Pro Thr Asp Thr Asn Phe Val Phe Leu Asp Leu Ser Lys Ala His Met
            290                 295                 300

Asn Pro Asp Val Leu Val Lys Gly Leu Lys Tyr Arg Ile Lys Leu
305                 310                 315                 320

Met Gly Gly Arg Ile Ala Phe His Tyr Gln Val Thr Gln Glu Thr Leu
                325                 330                 335

Glu Lys Ala Lys Cys Ala Ile Leu Glu Ser Phe Glu His Ala Lys Glu
            340                 345                 350

His Pro Phe Asn Gln Gln Gly Gln Thr Lys Ile Tyr Arg Ser Glu Ser
            355                 360                 365

Thr Asp Lys Ile Asp Ile Asp Gly Asn Ser Ile His Gly Ile Lys Thr
            370                 375                 380

Tyr Lys Tyr
385

<210> SEQ ID NO 29
<211> LENGTH: 388
<212> TYPE: PRT
<213> ORGANISM: Zygosaccharomyces bailii

<400> SEQUENCE: 29

Met Pro Asp Tyr Glu Leu Pro Pro Val Tyr Thr Thr Ala Ser Asn Asp
1               5                   10                  15

Leu Arg Ser Asp Thr Phe Thr Thr Pro Thr Glu Met Met Gln Ala
            20                  25                  30

Gly Ile Ala Ala Ser Ile Gly Asp Ala Val Tyr Gln Glu Asp Ile Asp
            35                  40                  45

Thr Ile Arg Leu Glu Gln Thr Val Ala Gln Leu Ala Gly Lys Glu Ala
    50                  55                  60

Gly Leu Phe Cys Val Ser Gly Thr Leu Ser Asn Gln Ile Ala Val Arg
65                  70                  75                  80

Thr His Leu Thr Gln Pro Pro Tyr Ser Val Leu Cys Asp Tyr Arg Ser
                85                  90                  95

His Val Tyr Thr His Glu Ala Ala Gly Leu Ala Ile Leu Ser Gln Ala
            100                 105                 110

Met Val Val Pro Val Val Pro Ser Asn Gly Asn Tyr Met Thr Leu Glu
            115                 120                 125

Asp Ile Lys Arg His Tyr Val Pro Asp Asp Gly Asp Ile His Gly Ala
            130                 135                 140

Pro Thr Arg Leu Val Ser Leu Glu Asn Thr Leu His Gly Ile Val Tyr
145                 150                 155                 160

Pro Leu Glu Glu Leu Leu Arg Ile Arg Ala Trp Cys Leu Glu Asn Asp
                165                 170                 175

Ile Arg Ile His Cys Asp Gly Ala Arg Leu Trp Asn Ala Ser Val Ala
            180                 185                 190

Ala Gly Val Pro Met Arg Gln Phe Gly Glu Leu Phe Asp Ser Ile Ser
            195                 200                 205

Ile Cys Leu Ser Lys Ser Met Gly Ala Pro Ile Gly Ser Val Leu Val
            210                 215                 220

Gly Asp Leu Lys Phe Ile Lys Lys Cys Asn His Phe Arg Lys Gln Gln
225                 230                 235                 240
```

```
Gly Gly Gly Ile Arg Gln Ser Gly Met Met Cys Ala Met Ala Leu Thr
                245                 250                 255

Thr Val Thr Gly Asp Trp Lys Ser Lys Leu Leu His Ser His Gln Leu
            260                 265                 270

Ala His Glu Leu Ala Arg Phe Cys Ile Glu Lys Gly Ile Pro Leu Glu
            275                 280                 285

Ser Pro Ala Asp Thr Asn Phe Val Phe Ile Ser Leu Ser Gln Ala Lys
        290                 295                 300

Met Asp Pro Asp Val Leu Val Lys Lys Gly Leu Lys Tyr Gly Val Lys
305                 310                 315                 320

Phe Met Gly Gly Arg Ile Ala Phe His Tyr Gln Val Asn Arg Asp Thr
                325                 330                 335

Leu Glu Lys Ala Lys Met Ala Ile Leu Glu Thr Phe Glu Tyr Ala Lys
            340                 345                 350

Glu His Pro Phe Asn Ser Glu Gly Glu Thr Lys Ile Tyr Arg Ser Glu
            355                 360                 365

Ser Thr Glu Arg Val Asp Ile Asp Gly Arg Pro Ile His Asp Ile Lys
        370                 375                 380

Thr Tyr Lys Tyr
385

<210> SEQ ID NO 30
<211> LENGTH: 376
<212> TYPE: PRT
<213> ORGANISM: Schizosaccharomyces pombe

<400> SEQUENCE: 30

Met Ser Gly Ser Val Thr Ser Thr Thr Glu Thr Arg Leu Cys Pro
1               5                   10                  15

Ser Asn Gln Gly Ser Ala Lys Lys Tyr Arg Pro Trp Asn Asp Phe Arg
            20                  25                  30

Ser Asp Thr Leu Thr Val Pro Thr Asp Glu Met Arg Arg Ile Met Tyr
        35                  40                  45

Glu Ala Ser Asp Gly Asp Cys Val Tyr Glu Gly Asp Glu Asp Thr Arg
    50                  55                  60

Lys Leu Glu Val Tyr Val Ala Lys Leu Thr Gly Lys Glu Ala Ala Leu
65                  70                  75                  80

Phe Val Thr Ser Gly Thr Gln Gly Asn Gln Leu Cys Ile Arg Ser His
                85                  90                  95

Leu His Gln Pro Pro His Ser Ile Ile Cys Asp Asp Arg Ala His Ile
            100                 105                 110

Tyr Asn Trp Glu Ala Gly Ala Ile Gly Leu Phe Thr Gln Ala Ile Val
        115                 120                 125

Arg Pro Ile Ser Pro Lys Asn Asn Val Tyr Ile Thr Ala Glu Glu Ile
    130                 135                 140

Glu Asn Lys Leu Ile Leu Gly Asn Asp Ile His Phe Ser Pro Thr Gly
145                 150                 155                 160

Leu Ile Cys Leu Glu Asn Thr Ile Lys Gly Ala Val Val Pro Leu Asp
                165                 170                 175

Glu Val Ala Arg Ile Ser Gly Leu Ala Lys Ala His Lys Ile Pro Leu
            180                 185                 190

His Cys Asp Gly Ala Arg Leu Trp Asp Ala Ala Val Ala Ser Asn Val
        195                 200                 205

Ser Ile Lys Glu Tyr Cys Ser Tyr Phe Asp Ser Val Ser Leu Cys Leu
    210                 215                 220
```

```
Ser Lys Gly Leu Ala Ala Pro Val Gly Ser Ile Val Gly Pro Arg
225                 230                 235                 240

Asp Phe Ile Ala Lys Ala Lys Trp Phe Arg Lys Ala Tyr Gly Gly
            245                 250                 255

Leu Arg Gln Ser Gly Met Leu Ala Ala Gly Leu Tyr Ser Ile Gln
            260                 265                 270

His Asn Phe Pro Leu Leu Lys Gln Val His Lys Tyr Ala Ile Glu Val
            275                 280                 285

Ala Glu Tyr Ala Glu Ser Leu Gly Ile Glu Leu Glu Val Pro Thr Gln
            290                 295                 300

Ser Asn Met Val Thr Leu Ala Asn Ile Asn Val Ala Ile Leu Cys Asp
305                 310                 315                 320

Glu Ala Lys Lys Ser Gly Ile Ile Leu Met Gly Pro Arg Ile Val Phe
            325                 330                 335

His Ile Gln Ile Thr Pro Asp Ala Val Glu Ile Leu Lys Asn Val Leu
            340                 345                 350

Arg Arg Thr Val Glu Arg Gln Ala Val Glu Thr His Ile Val Ala Lys
            355                 360                 365

Pro Gly Glu Phe Cys Val Gly Tyr
            370                 375

<210> SEQ ID NO 31
<211> LENGTH: 395
<212> TYPE: PRT
<213> ORGANISM: Kluyveromyces lactis

<400> SEQUENCE: 31

Met Thr Ala Ser Asp Lys Lys Ser Thr Ala Ala Pro Ser Glu Pro
1               5                   10                  15

Ala Tyr Thr Ser Ala Ala Asn Asp Leu Arg Ser Asp Thr Phe Thr Thr
            20                  25                  30

Pro Thr Lys Glu Met Leu Glu Ala Ala Phe Asn Ala Ser Ile Gly Asp
            35                  40                  45

Ala Val Tyr Asn Glu Asp Val Asp Thr Ile Glu Leu Glu Thr Val Val
50                  55                  60

Ala Arg Leu Ala Gly Lys Glu Ala Gly Leu Phe Cys Val Ser Gly Thr
65                  70                  75                  80

Leu Ser Asn Gln Ile Gly Leu Arg Thr His Leu Phe Gln Pro Pro Tyr
            85                  90                  95

Ser Ile Leu Cys Asp Tyr Arg Ala His Val Tyr Thr His Glu Ala Ala
            100                 105                 110

Gly Leu Ala Ile Leu Ser Gln Ala Met Val Thr Pro Val Ile Pro Ser
            115                 120                 125

Asn Gly Asp Tyr Met Thr Leu Glu Asp Ile Lys Ala His Tyr Ile Pro
            130                 135                 140

Asp Asp Gly Asp Ile His Gly Ala Pro Thr Arg Val Leu Ser Leu Glu
145                 150                 155                 160

Asn Thr Leu His Gly Ile Val Tyr Pro Leu Glu Glu Leu Ile Arg Ile
            165                 170                 175

Lys Gly Trp Cys Leu Glu Asn Asp Ile Lys Leu His Cys Asp Gly Ala
            180                 185                 190

Arg Ile Trp Asn Ala Val Val Glu Ser Gly Val Ser Leu Lys Gln Tyr
            195                 200                 205

Gly Glu Ile Phe Asp Ser Ile Ser Ile Cys Leu Ser Lys Ser Met Gly
            210                 215                 220
```

Ala Pro Met Gly Ser Val Leu Val Gly Ser Asn Lys Phe Val Lys
225                 230                 235                 240

Cys Asn His Phe Arg Lys Gln Gln Gly Gly Val Arg Gln Ser Gly
                245                 250                 255

Ile Met Cys Arg Met Ala Leu Cys Ala Val Asn Gly Asp Trp Lys Thr
                260                 265                 270

Lys Met Gly Tyr Ser His Gln Leu Ala His Glu Leu Ala Lys Phe Cys
                275                 280                 285

Lys Asp Asn Gly Ile Pro Leu Glu Ser Pro Ala Asp Thr Asn Phe Val
                290                 295                 300

Phe Leu Asp Leu Gln Lys Ala Lys Met Asn Pro Asp Val Leu Val Lys
305                 310                 315                 320

Lys Gly Leu Lys Tyr Gly Val Lys Leu Met Gly Gly Arg Val Ser Phe
                325                 330                 335

His Tyr Gln Val Thr Arg Glu Thr Leu Glu Asn Val Lys Ser Ala Val
                340                 345                 350

Leu Glu Thr Phe Gln Tyr Ala Lys Glu Asn Pro Phe Asp Thr Asn Gly
                355                 360                 365

Pro Thr Lys Ile Tyr Arg Ser Glu Ser Thr Asp Phe Asp Ile His Gly
                370                 375                 380

Asn Pro Ile Ser Asp Ile Lys Thr Tyr Lys Tyr
385                 390                 395

<210> SEQ ID NO 32
<211> LENGTH: 372
<212> TYPE: PRT
<213> ORGANISM: Pichia pastoris

<400> SEQUENCE: 32

Met Thr Lys Glu Asp Phe Pro Cys Ala Asn Glu Phe Arg Ser Asp Thr
1               5                   10                  15

Phe Thr Val Pro Thr Ala Ser Met Ile Gln Ser Val Ala Leu Ala Ser
                20                  25                  30

Val Gly Asp Ser Val Tyr Ala Glu Asp Leu Asp Thr Leu Asn Leu Glu
                35                  40                  45

Glu Lys Val Ala Gln Met Ala Asp Lys Glu Ala Gly Leu Phe Cys Val
        50                  55                  60

Ser Gly Thr Leu Ser Asn Gln Ile Gly Leu Arg Ser His Leu Met Gln
65                  70                  75                  80

Pro Pro His Arg Ile Leu Cys Asp Ser Arg Ala His Val Tyr Met His
                85                  90                  95

Glu Ala Gly Gly Leu Ala Thr Leu Ser Gln Ala Met Val Thr Pro Val
                100                 105                 110

Thr Pro Arg Asn Gly Leu Tyr Leu Thr Leu Glu Asp Val Val Asp Asn
                115                 120                 125

Tyr Ile Pro Asp Asp Gly Asp Ile His Met Ala Pro Thr Lys Val Val
                130                 135                 140

Ser Leu Glu Asn Thr Ile His Gly Ile Ile Thr Pro Leu Glu Glu Ile
145                 150                 155                 160

Ala Arg Ile Ser Glu Trp Cys Arg Glu Asn Asp Val Arg Leu His Cys
                165                 170                 175

Asp Gly Ala Arg Leu Trp Asn Ala Ser Val Glu Thr Asn Thr Pro Leu
                180                 185                 190

Ser Glu Tyr Gly Lys Leu Phe Asp Ser Ile Ser Leu Cys Leu Ser Lys
                195                 200                 205

```
Ser Leu Gly Ser Pro Met Gly Ser Val Leu Val Gly Asp Arg Lys Phe
    210                 215                 220
Ile Asp Lys Ala Asn His Phe Lys Lys Gln Asn Gly Gly Ile Arg
225                 230                 235                 240
Gln Ser Gly Phe Ile Ala Arg Met Ala Ser Ile Ala Ile Asp Glu Asn
                245                 250                 255
Leu Gly Lys Leu Arg Gln Ser His Glu Tyr Ala Lys Asp Val Ala Arg
                260                 265                 270
Phe Leu Gln Asp Asn Gly Val Pro Leu Glu Cys Pro Thr His Thr Asn
            275                 280                 285
Phe Val Phe Val Asp Gln Lys Lys Ala Arg Ile Asp Pro Asp His Leu
        290                 295                 300
Val Ala Met Gly Glu Lys Tyr Asn Val Asn Ile Met Gly Thr Arg Phe
305                 310                 315                 320
Ala Phe His Phe Gln Asn Ser Lys Glu Ala Val Glu Arg Leu Lys Gln
                325                 330                 335
Ala Ile Met Glu Thr Phe Lys Tyr Ser Gln Glu His Pro Tyr Val Ser
            340                 345                 350
Thr Gly Ala Lys Arg Leu Tyr Thr Ser Lys Ser Arg Ser Asn Ser Pro
        355                 360                 365
Val Leu Lys Asn
    370
```

OPTIMIZED HOST CELLS FOR THE PRODUCTION OF GLUTATHIONE

CROSS-REFERENCE TO RELATED APPLICATIONS AND DOCUMENTS

This application claims priority from U.S. provisional patent application 62/315,796 filed on Mar. 31, 2016. A sequence listing in electronic form is being filed concurrently. The content of the priority application and of the sequence listing are herewith included in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 580127_420USPC_SEQUENCE_LISTING.txt. The text file is 133 KB, was created on Sep. 26, 2018, and is being submitted electronically via EFS-Web.

TECHNOLOGICAL FIELD

The present disclosure relates to genetically modified host cells (preferably genetically modified yeast host cells) capable of producing and accumulating glutathione as well as processes using same. The genetically modified host cells express a mutated cystathionine beta-synthase protein (Cys4p) having an increased biological activity, a mutated Yap1p having a limited ability of being translocated from the nucleus to the cytoplasm and/or an heterologous threonine aldolase (Gly1p).

BACKGROUND

Glutathione (GSH, L-γ-glutamyl-L-cysteinylglycine) is an ubiquitous non-protein thiol tripeptide which plays a role in several key physiological processes and is increasingly used in the pharmaceutical, cosmetic and food additive industries. This strong antioxidant is of high interest in baking (dough relaxation for example), oenology and brewing (aroma components stabilizer) or as a flavor enhancer ("kokumi" taste) in yeast extracts. Due to GSH's high demand, increasing the efficiency of its production is commercially important. *Saccharomyces cerevisiae* can be used for GSH microbial synthesis since it is "Generally Regarded As Safe" (GRAS), is a low secretor and is relatively easy to grow at high cell densities on inexpensive substrates.

In the cell, glutathione exists mostly in reduced (GSH) and oxidized (GSSG) forms, and is synthesized from three precursor amino-acids (glutamate, cysteine, and glycine) over two consecutive ATP-dependent reactions. First, the L-γ-glutamylcysteine synthetase (Gsh1p) converts cysteine into γ-glutamylcysteine, which is then converted into glutathione by the GSH synthetase (Gsh2p). GSH biosynthesis is tightly regulated at three different levels: transcriptional, post-translational, and substrate availability.

The biosynthesis of glutathione (GSH) requires three amino acids: cysteine, glutamate and glycine. During yeast propagation, the addition of cysteine results in increased production of both GSH and the intermediate γ-glutamylcysteine (γ-GC). Co-feeding of cysteine and glycine results in the conversion of a portion of the (γ-GC) to GSH.

There are two main pathways leading to the synthesis of glycine in yeast. In one pathway L-threonine aldolase, encoded by GLY1, produces glycine from L-threonine (which is produced from the glycolytic intermediate oxaloacetate). Glycine may also be formed from L-serine, via two hydroxymethyltransferases, encoded by SHM1 (mitochondrial) and SHM2 (cytosolic).

Microbial production of GSH using genetically engineered yeast strains has a potential to satisfy its increasing industrial demand. Conventional methods allow increasing the GSH content in the cells only two-fold compared to the native level, thus increasing further the GSH concentration would allow for improving the efficiency of these products to a considerable extent. The concentration range of GSH in *S. cerevisiae* is of 0.1-1% of the dry cell weight. This varies according to the strain, the growth conditions and the GSH measurement method employed.

It would be highly desirable to be provided with genetically modified host cells capable of producing and accumulating an increase amount of intracellular GSH (preferably mostly in a reduced form) and reducing the amount of intracellular γ-glutamylcysteine or free cysteine, when compared to its corresponding amount in the parental strain. In some embodiments, it would be desirable to reduce or even eliminate supplementation with cysteine or glycine during the GSH production phase (e.g., the fermentation) with the genetically modified host cells. In some embodiments, it would also be desirable to be provided with processes for making GSH and preparations (raw, semi-purified and purified) comprising GSH using the genetically modified host cells.

BRIEF SUMMARY

The present disclosure concerns a genetically modified host cell (preferably a genetically modified host cell) and its use for the production of GSH. The genetically modified host cell synthesizes more total thiols (also known as total GHS and apparent GSH), which include the free intracellular cysteine, γ-glutamylcysteine (g-GC or γ-GC) and true GSH. Moreover, the genetically modified strain accumulates a higher proportion of true GSH and very little g-GC compared to corresponding wild-type strains.

According to a first aspect, the present disclosure provides a process of making glutathione. Broadly the process comprises fermenting a substrate with a genetically modified host cell to obtain a fermented mixture comprising glutathione. The genetically modified host cell has (i) a first heterologous nucleic acid molecule coding for a mutated cystathionine beta-synthase protein (Cys4p) having an increased biological activity when compared to a wild-type Cys4p, (ii) a second heterologous nucleic acid molecule coding for a mutated Yap1p having a reduced ability of being translocated from the nucleus to the cytoplasm when compared to a wild-type Yap1p and/or (iii) a third heterologous nucleic acid molecule coding for a threonine aldolase protein (Gly1p). In an embodiment, the genetically modified host cell has the first heterologous nucleic acid molecule and at least one of the second heterologous nucleic acid molecule or the third heterologous nucleic acid molecule. In an embodiment, the mutated Cys4p is a fragment of the wild-type Cys4p. For example, the mutated Cys4p can be obtained by deleting one or more C-terminal amino acid residue(s) from the wild-type Cys4p. In still another example, the mutated Cys4p can be obtained by deleting the regulatory domain from the wild-type Cys4p. In an embodiment, the mutated Cys4p consists of the amino acid sequence of SEQ ID NO: 2. In still another embodiment, in the genetically modified host cell, at least one copy of the native nucleic acid molecule coding for the wild-type Cys4p is replaced by the first heterologous nucleic acid molecule. In yet another embodiment, the genetically modified host cell comprises at least one, at least two, at least three or at least four copies of the first heterologous nucleic acid molecule. In a further embodiment, the mutated Yap1p is substantially located in the nucleus of the genetically modified host cell. In still another embodiment, the mutated Yap1p has at least one amino acid substitution when compared to the wild-type Yap1p. For example, the at least one amino acid substitution can be located in a domain corresponding to a cysteine-rich domain of the wild-type Yap1p. In yet another example, the mutated Yap1p can be obtained by substituting a cysteine residue with an hydrophilic amino acid residue (such as, for example, an aspartic acid residue) in the domain corresponding to the cysteine-rich domain of the wild-type Yap1p. In still another example, the substituted cysteine residue of the mutated Yap1p is located at a position corresponding to residue 626 of SEQ ID NO: 3. In still another embodiment, the mutated Yap1p comprises the amino acid sequence of SEQ ID NO: 4 or SEQ ID NO: 5. In an embodiment, in the genetically modified host cell, at least one copy of the native nucleic acid molecule coding for the wild-type Yap1p is replaced by the second heterologous nucleic acid molecule. In another embodiment, the genetically modified host cell comprises at least one, at least two, at least three or at least four copies of the second heterologous nucleic acid molecule. In a further embodiment, the genetically modified host cell comprises at least one, at least two, at least three or at least four copies of the third heterologous nucleic acid molecule. In still yet another embodiment, the genetically modified host cell comprises the first heterologous nucleic acid molecule and the second heterologous nucleic acid molecule; the first heterologous nucleic acid molecule and the third heterologous nucleic acid molecule; the second heterologous nucleic acid molecule and the third heterologous nucleic acid molecule; or the first heterologous nucleic acid molecule, the second heterologous nucleic acid molecule and the third heterologous nucleic acid molecule. In an embodiment, the process further comprises processing the fermented mixture into a yeast extract or a yeast hydrolysate. In still another embodiment, the process further comprises purifying or inactivating the genetically modified host cell from the fermented mixture. In yet another embodiment, the process further comprises purifying the glutathione from the fermented mixture. In another embodiment, the genetically modified host cell is a genetically modified yeast host cell. For example, the genetically modified yeast host cell can be from the genus *Saccharomyces*. In another example, the genetically modified yeast host cell is from the species *Saccharomyces cerevisiae*.

According to a second aspect, the present disclosure provides a fermented substrate, a yeast extract, a yeast hydrolysate, a purified genetically modified host cell and/or an inactivated genetically modified host cell obtainable or obtained by the process described herein.

According to a third aspect, the present disclosure concerns a process for increasing glutathione accumulation in a genetically modified host cell. Broadly, the process comprises introducing a first heterologous nucleic acid molecule, a second heterologous nucleic acid molecule and/or a third heterologous nucleic acid molecule in a parental yeast host cell to generate the genetically modified host cell. In the process, the first heterologous nucleic acid molecule codes for a mutated cystathionine beta-synthase protein (Cys4p) having an increased biological activity when compared to a wild-type Cys4p. In addition, the second heterologous nucleic acid molecule codes for a mutated Yap1p having a limited ability of being exported in the cytoplasm when compared to a wild-type Yap1p. Further, the third heterologous nucleic acid molecule codes for an heterologous threonine aldolase (Gly1p). In an embodiment, the genetically modified host cell has the first heterologous nucleic acid molecule and at least one of the second heterologous nucleic acid molecule or the third heterologous nucleic acid molecule. In an embodiment, the mutated Cys4p is a fragment of the wild-type Cys4p. For example, the mutated Cys4p can be obtained by deleting one or more C-terminal amino acid residue from the wild-type Cys4p. In still another example, the mutated Cys4p can be obtained by deleting the regulatory domain from the wild-type Cys4p. In an embodiment, the mutated Cys4p consists of the amino acid sequence of SEQ ID NO: 2. In still another embodiment, in the genetically modified host cell, at least one copy of the native nucleic acid molecule coding for the wild-type Cys4p is replaced by the first heterologous nucleic acid molecule. In yet another embodiment, the genetically modified host cell comprises at least one, at least two, at least three or at least four copies of the first heterologous nucleic acid molecule. In a further embodiment, the mutated Yap1p is substantially located in the nucleus of the genetically modified host cell. In still another embodiment, the mutated Yap1p has at least one amino acid substitution when compared to the wild-type Yap1p. For example, the at least one amino acid substitution can be located in a domain corresponding to a cysteine-rich domain of the wild-type Yap1p. In yet another example, the mutated Yap1p can be obtained by substituting a cysteine residue with an hydrophilic amino acid residue (such as, for example, an aspartic acid residue) in the domain corresponding to the cysteine-rich domain of the wild-type Yap1p. In still another example, the substituted cysteine residue of the mutated Yap1p is located at a position corresponding to residue 626 of SEQ ID NO: 3. In still another example, the mutated Yap1p comprises the amino acid sequence of SEQ ID NO: 4 or SEQ ID NO: 5. In an embodiment, in the genetically modified host cell, at least one copy of the native nucleic acid molecule coding for the wild-type Yap1p is replaced by the second heterologous nucleic acid molecule. In another embodiment, the genetically modified host cell comprises at least one, at least two, at least three or at least four copies of the second heterologous nucleic acid molecule. In yet another embodiment, the genetically modified host cell comprises at least one, at least two, at least three or at least four copies of the third heterologous nucleic acid molecule. In another embodiment, the genetically modified host cell is a genetically modified yeast host cell. For example, the genetically modified yeast host cell can be from the genus *Saccharomyces*. In another example, the genetically modified yeast host cell is from the species *Saccharomyces cerevisiae*.

According to a fourth aspect, the present disclosure concerns a genetically modified host cell obtained by the process described herein.

According to a fifth aspect, the present disclosure concerns a genetically modified host cell comprising at least two of (i) a first heterologous nucleic acid molecule encoding a mutated cystathionine beta-synthase protein (Cys4p) having an increased biological activity when compared to a wild-type Cys4p; (ii) a second heterologous nucleic acid molecule encoding a mutated Yap1p having a reduced ability of being translocated from the nucleus to the cytoplasm when compared to the wild-type Yap1p; and/or (iii) a third heterologous nucleic acid molecule encoding a threonine aldolase (Gly1p). In an embodiment, the genetically modified host cell has the first heterologous nucleic acid molecule and at least one of the second heterologous nucleic acid molecule or the third heterologous nucleic acid molecule. In an embodiment, the mutated Cys4p is a fragment of the wild-type Cys4p. For example, the mutated Cys4p can be obtained by deleting one or more C-terminal amino acid residue from the wild-type Cys4p. In still another example, the mutated Cys4p can be obtained by deleting the regulatory domain from the wild-type Cys4p. In an embodiment, the mutated Cys4p consists of the amino acid sequence of SEQ ID NO: 2. In still another embodiment, in the genetically modified host cell, at least one copy of the native nucleic acid molecule coding for the wild-type Cys4p is replaced by the first heterologous nucleic acid molecule. In yet another embodiment, the genetically modified host cell comprises at least one, at least two, at least three or at least four copies of the first heterologous nucleic acid molecule. In a further embodiment, the mutated Yap1p is substantially located in the nucleus of the genetically modified host cell. In still another embodiment, the mutated Yap1p has at least one amino acid substitution when compared to the wild-type Yap1p. For example, the at least one amino acid substitution can be located in a domain corresponding to a cysteine-rich domain of the wild-type Yap1p. In yet another example, the mutated Yap1p can be obtained by substituting a cysteine residue with an hydrophilic amino acid residue (such as, for example, an aspartic acid residue) in the domain corresponding to the cysteine-rich domain of the wild-type Yap1p. In still another example, the substituted cysteine residue of the mutated Yap1p is located at a position corresponding to residue 626 of SEQ ID NO: 3. In still another example, the mutated Yap1p comprises the amino acid sequence of SEQ ID NO: 4 or SEQ ID NO: 5. In an embodiment, in the genetically modified host cell, at least one copy of the native nucleic acid molecule coding for the wild-type Yap1p is replaced by the second heterologous nucleic acid molecule. In another embodiment, the genetically modified host cell comprises at least one, at least two, at least three or at least four copies of the second heterologous nucleic acid molecule. In yet another embodiment, the genetically modified host cell comprises at least one, at least two, at least three or at least four copies of the third heterologous nucleic acid molecule. In another embodiment, the genetically modified host cell is a genetically modified yeast host cell. For example, the genetically modified yeast host cell can be from the genus *Saccharomyces*. In another example, the genetically modified yeast host cell is from the species *Saccharomyces cerevisiae*.

BRIEF DESCRIPTION OF THE DRAWINGS

Having thus generally described the nature of the invention, reference will now be made to the accompanying drawings, showing by way of illustration, a preferred embodiment thereof, and in which:

FIG. 7 provides the amino acid sequence alignment of wild-type Cys4p from *Saccharomyces cerevisiae* (SEQ ID NO: 6), *Saccharomyces bayanus* (SEQ ID NO: 8), *Cyberlindnera jadinii* (SEQ ID NO: 12), *Torulaspora delbrueckii* (SEQ ID NO: 14), *Zygosaccharomyces bailii* (SEQ ID NO: 16), *Scheffersomyces (Pichia) stipitis* (SEQ ID NO: 19), *Kluyveromyces lactis* (SEQ ID NO: 20) and *Pichia pastoris* (SEQ ID NO: 22). The catalytic and regulatory documents are boxed and identified. The essential active-site residues are threonine-81, serine-82, threonine-85, glutamine-157 and tyrosine-158 when using the sequences of *S. cerevisiae* (Aitken et al., 2004). The amino acid alignment was generated using the CLUSTAL® OMEGA software using default parameters except for order which was changed from aligned to input.

FIG. 8 provides the amino acid sequence alignment of wild-type Yap1p from *Saccharomyces cerevisiae* strain (SEQ ID NO: 7), *Saccharomyces bayanus* (SEQ ID NO: 9), *Saccharomyces kudriavzevii* (SEQ ID NO: 11), *Cyberlindnera jadinii* (SEQ ID NO: 13), *Torulaspora delbrueckii* (SEQ ID NO: 15), *Zygosaccharomyces bailii* (SEQ ID NO: 17), *Schizosaccharomyces pombe* (SEQ ID NO: 18), *Kluyveromyces lactis* (SEQ ID NO: 21) and *Pichia pastoris* (SEQ ID NO: 23). The basic region (DNA binding), leucine zipper and cysteine-rich domain are boxed and identified. The amino acid alignment was generated using the CLUSTAL® OMEGA software using default parameters except for order which was changed from aligned to input.

FIG. 9 provides the amino acid sequence alignment of wild-type Gly1p from *Saccharomyces cerevisiae* strain (SEQ ID NO: 24), *Saccharomyces bayanus* (SEQ ID NO: 25), *Saccharomyces kudriavzevii* (SEQ ID NO: 26), *Cyberlindnera jadinii* (SEQ ID NO: 27), *Torulaspora delbrueckii* (SEQ ID NO: 28), *Zygosaccharomyces bailii* (SEQ ID NO: 29), *Schizosaccharomyces pombe* (SEQ ID NO: 30), *Kluyveromyces lactis* (SEQ ID NO: 31) and *Pichia pastoris* (SEQ ID NO: 32). The basic region (DNA binding), leucine zipper and cysteine-rich domain are boxed and identified. The amino acid alignment was generated using the CLUSTAL® OMEGA software using default parameters except for order which was changed from aligned to input.

DETAILED DESCRIPTION

Figure 1:
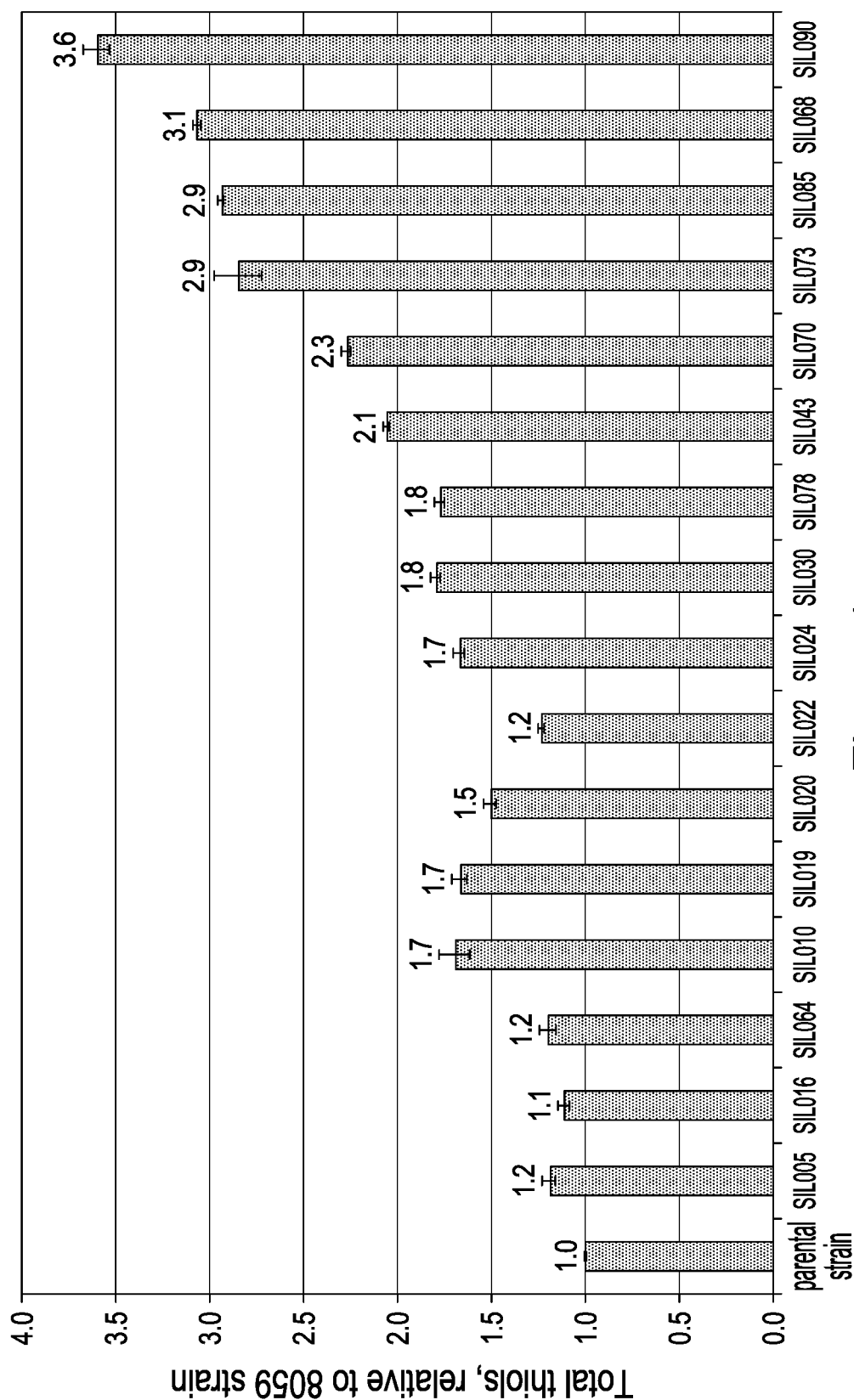
FIG. 1 provides the relative total thiol content of a control non-modified *S. cerevisiae* strain (parental strain) and various genetically modified *S. cerevisiae* strains SIL005, SIL016, SIL064, SIL010, SIL019, SIL020, SIL022, SIL024, SIL030, SIL078, SIL043, SIL070, SIL085, SIL068 and SIL090. Values are relative to the parental (wild-type, parental, not genetically modified) *S. cerevisiae* strain. Values are average of duplicates.

The present disclosure concerns genetically modified host cells and their uses in processes for making glutathione during fermentation. The present disclosure also especially concerns genetically modified yeast host cells and their uses in processes for making glutathione during fermentation. In some embodiments, the use of the genetically modified host cells allows for a substantial increase in total thiols and especially in glutathione production and accumulation. Under certain circumstances, the total thiols content of genetically modified host cells is increased by 20%, 30%, 40%, 50%, 60%, 70%, 80%, 90%, 100% or even higher when compared to corresponding wild-type (i.e., parental or non-genetically modified) cells. In other circumstances, the genetically modified host cells generate a higher proportion of true GSH than its γ-L-glutamyl-L-cysteine byproduct when compared to corresponding wild-type (i.e., parental or non-genetically modified host) cells. In some circumstances, the genetically modified host cells generate less intracellular free cysteine when compared to corresponding wild-type (i.e., parental or non-genetically modified host) cells. In still other circumstances, the genetically modified host cells require less supplementation (for example less cysteine and/or less glycine supplementation) that the corresponding wild-type (i.e., parental or non-genetically modified) cells during fermentation to achieve the same GSH content.

Genetically Modified Host Cells

The present disclosure provides genetically modified host cells capable of making and accumulating more GSH than corresponding parental or non-genetically modified host cells. The genetically modified host cells can be genetically modified yeast host cells. In the context of the present disclosure, the genetically modified host cells have at least one genetic modification allowing the expression of a mutated cystathionine beta-synthase protein Cys4p, a second genetic modification allowing the expression of a mutated Yap1p and/or a third genetic modification allowing the expression of an heterologous threonine aldolase (Gly1p). In some embodiments, the genetically modified host cell also includes further genetic modifications, for example, for expressing an heterologous gamma glutamyl cysteine synthetase 1 protein (Gsh1p) and/or an heterologous glutathione synthetase 2 protein (Gsh2p).

The genetically modified host cell can be a yeast host cell. Suitable yeast host cells that can be genetically modified as described herein can be, for example, from the genus *Arxula, Brettanomyces, Candida, Cryptococcus, Debaryomyces, Kloeckera, Kluyveromyces, Hanseniaspora, Hansenula, Metschnikowia, Pichia, Phaffia, Saccharomyces, Scheffersomyces, Schizosaccharomyces, Schwanniomyces, Sporobolomyces, Starmerella, Tetrapisispora, Yarrowia* or *Zygosaccharomyces*. In some embodiments, the yeast host cell can be an oleaginous yeast cell. For example, the oleaginous yeast host cell can be from the genus *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. In some alternative embodiment, the yeast host cell can be an oleaginous microalgae host cell (e.g., for example, from the genus *Thraustochytrium* or *Schizochytrium*). Suitable yeast species can include, for example, *Arxula adeninivorans, Brettanomyces bruxellensis, Candida albicans, Candida colliculosa/Torulaspora Delbrueckii, Candida tropicalis, Candida utilis (Cyberlindnera jadinii), Cryptococcus skinneri, Debaryomyces sp., Debaryomyces hansenii, Debaryomyces polymorphus, Hanseniaspora vinea, Hanseniaspora occidentalis, Hanseniaspora uvarum, Hansenula polymorpha, Kluyveromyces lactis, Kluyveromyces marxianus* var *drosophilarum, Kluyveromyces thermotolerans, Kluyveromyces wickerhamii, Kluyveromyces fragilis, Metschnikowia pulcherrima (Candida pulcherrima), Metschnikowia fructicola, Phaffia rhodozyma, Pichia anomala, Pichia kudriavzevii, Pichia occidentalis, Pichia pastoris, Saccharomyces bulgari, Saccharomyces cerevisiae, Saccharomyces diastaticus, Saccharomyces exiguous, Saccharomyces uvarum, Scheffersomyces stipitis, Schizosaccharomyces pombe, Schwanniomyces occidentalis, Sporobolomyces, Starmerella bombicolla, Tetrapisispora phaffii, Yarrowia lipolytica, Zygosaccharomyces bailii* or *Zygosaccharomyces rouxii*. In one particular embodiment, the genetically modified yeast host cell is from the genus *Saccharomyces* and, in a further embodiment, from the species *Saccharomyces cerevisiae*.

The genetically modified host cell can be a bacteria. Suitable bacterial host cells that can be genetically modified as described herein can be a Gram-positive or a Gram-negative bacteria. The genetically modified bacterial host cell can be from the phylum Acidobacteria, Actinobacteria, Aquificae, Bacteroidetes, Chlamydiae, Cholorobi, Chloroflexi, Chrysiogenetes, Cyanobacteria, Deferribacteres, Deinococcus-Thermus, Dictyoglomi, Fibrobacteres, Firmicutes, Fusobacteria, Gemmatimonadetes, Lentisphaerae, Nitrospirae, Planctomycetes, Proteobacteria, Spirochaetes, Thermodesulfobacteria, Thermotogae or Verrucomicrobia. In one particular embodiment, the genetically modified bacterial host cell is *Escherichia coli*.

As indicated above, the genetically modified host cells includes one or more heterologous nucleic acid molecule encoding one or more heterologous protein (e.g., mutated Cys4p, mutated Yap1p, Gly1p, Gsh1p and/or Gsh2p). The term "heterologous" when used in reference to a nucleic acid molecule (such as a promoter or a coding sequence) or a protein refers to a nucleic acid molecule or a protein that is not natively found in the host organism or cell. "Heterologous" also includes a native coding region, or portion thereof, that is removed or amplified from the source organism and subsequently reintroduced into the source organism in a form that is different from the corresponding native gene, e.g., not in its natural location in the organism's genome. The heterologous nucleic acid molecule(s) is(are) purposively introduced into the host cell. An "heterologous" nucleic acid molecule or protein may be derived from any source, e.g., eukaryotes, prokaryotes, viruses, etc. In an embodiment, the heterologous nucleic acid molecule may be derived from an eukaryote (such as, for example, a yeast from the same genus or from the same species as the genetically modified host cell). The term "heterologous" as used herein also refers to an element (nucleic acid or protein) that is derived from a source other than the endogenous source. Thus, for example, a heterologous element could be derived from a different strain of host cell, or from an organism of a different taxonomic group (e.g., different kingdom, phylum, class, order, family genus, or species, or any subgroup within one of these classifications). The term "heterologous" is also used synonymously herein with the term "exogenous".

(i) Mutated Cystathionine Beta-Synthase (Cys4p)

Cysteine is known to be rate-limiting to GSH production. The cystathionine beta-synthase protein (also referred herein as Cys4p) catalyzes the first committed step in cysteine biosynthesis from homocysteine. Yeast strains exhibiting increased GSH production were shown to overexpress the transcripts encoding the Cys4p (Nisamedtinov et al., 2010, Nisamedtinov et al., 2011 and Orumets et al., 2012. The overexpression of the Cys4p has been shown to increase the GSH content in *Cyberlindnera jadinii* (formely *Candida utilis*) (Suzuki et al., 2011), *Pichia pastoris* (see CN 101220338 A and CN 101245363 A) and *Saccharomyces* cerevisiae (Suzuki et al., 2011). However, as shown in the present application, the overexpression of wild-type Cys4p in a yeast host cells leads only to a modest increase in total thiols (see results obtained for strain SIL005 on FIG. 1 for example).

It has been reported that a gain-of-function allele of CYS4, CYS4.353, encodes a cystathionine β-synthase exempt of its regulatory domain, resulting in higher specific activity (Jhee et al., 2000), leading to an accelerated growth rate and cell division in *S. cerevisiae* (Blank et al., 2009). Surprisingly, as shown in the present application, when the gene CYS4.353 is expressed in a genetically-modified yeast host cell, a vigorous increase in total thiols is observed (see, for example, results obtained for strain SIL010 on FIG. 1).

The genetically modified host cell of the present disclosure (and especially the genetically modified yeast host cell of the present disclosure) can include a first heterologous nucleic acid molecule coding for a mutated Cys4p having an increased biological activity when compared to a wild-type Cys4p. Such genetically modified host cell is thus capable of expressing the mutated Cys4p and, when placed in the appropriate conditions, the genetically modified host cell expresses the mutated Cys4p which ultimately increases the total thiols (and GSH production) during fermentation. The first heterologous nucleic acid molecule can be integrated in one or more copies in the genetically modified host cell (at one or more neutral integration site(s)). The first heterologous nucleic acid molecule can replace one or more copies of the native nucleic acid molecule coding for the native Cys4p. In an embodiment, the genetically modified host cell (and especially the genetically modified yeast host cell) can have one or more copies integrated copies of the first heterologous nucleic acid molecule (at one or more neutral integration sites) and in which at least one copy (or both copies) of the native nucleic acid molecule coding for the native Cys4p has been replaced by the first heterologous nucleic acid.

When expressed in the genetically modified host cell, the mutated Cys4p has increased biological activity than the wild-type Cys4p. In the context of the present disclosure, the wild-type Cys4p refers to a protein having cystathionine β-synthase activity, i.e. capable of enzymatically converting homocysteine into cystathionine. The wild-type or native Cys4p is encoded by a yeast genome and comprises both a catalytic domain and a regulatory domain. The wild-type Cys4p include essential active-site residues threonine-81, serine-82, threonine-85, glutamine-157 and tyrosine-158 (Aitken et al., 2004). FIG. 7 provides an amino acid alignment of wild-type Cys4p obtained from various yeast species. In an embodiment, the mutated Cys4p possesses the essential active-site residues corresponding to threonine-81, serine-82, threonine-85, glutamine-157 and tyrosine-158 as shown on FIG. 7.

In an embodiment, the wild-type Cys4p has the amino acid sequence of any one of SEQ ID NO: 6, 8, 10, 12, 14, 16, 20 or 22. In another embodiment, the wild-type Cys4p is any one of the wild-type Cys4p shown on FIG. 7. In still another embodiment, the wild-type Cys4p corresponds to the consensus sequence shown on FIG. 7.

In still another embodiment, the wild-type Cys4p of the present disclosure (which can be referred to as a variant) can share at least 60%, 65%, 70%, 75%, 80%, 85%, 90%, 95%, 96%, 97%, 98% or 99% of identity with any one of SEQ ID NO: 6, 8, 10, 12, 14, 16, 20 or 22 with the consensus sequence shown on FIG. 7, provided that the wild-type Cys4p does exhibit cystathionine β-synthase activity. "Identity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, N J (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

As indicated above, the genetically modified host cell of the present disclosure (such as the genetically modified yeast host cell) can, in some embodiments, include a first nucleic acid molecule encoding for a mutated Cys4p. In the context of the present disclosure, a "mutated" Cys4p refers to a protein having increased cystathionine β-synthase activity with respect to the wild-type Cys4p. In addition, when compared to the wild-type Cys4p, the mutated Cys4p has one or more amino acid residue difference with the wild-type Cys4p. Since the mutated Cys4p exhibits cystathionine β-synthase activity, the mutated Cys4p however retains threonine at position 81 (or at a corresponding position), serine at position 82 (or at a corresponding position), threonine at position 85 (or at a corresponding position), glutamine at position 157 (or at a corresponding position) and tyrosine at position 158 (or at a corresponding position) in its catalytic site.

In an embodiment, the mutated Cys4p is a fragment of the wild-type Cys4p exhibiting an increased cystathionine β-synthase activity and/or stability with respect to the "wild-type" Cys4p. As used in the context of the present disclosure, the term "fragment" refers to a protein having at least one less amino acid residues that the wild-type protein. The deletion can occur either at the N-, at the C- or at both the N- and C-terminus of the wild-type Cys4p. In the context of the present disclosure, when the mutated Cys4p is a fragment of the wild-type Cys4p, it at least comprises the catalytic domain of the wild-type Cys4p. In some embodiments, the mutated Cys4p can have at least at least 300, 310, 320, 330, 340, 350 or more consecutive amino acid residues of the wild-type Cys4p. In a specific embodiment, the mutated Cys4p is obtained by deleting one or more amino acid residues from the carboxy terminus of the wild-type Cys4p, such as, for example, by deleting a part of or the entire regulatory domain of the wild-type Cys4p. The regulatory domain of the Cys4p is illustrated at FIG. 7 and corresponds to positions 354 to 507 of SEQ ID NO: 1. In an embodiment, the mutated Cys4p consists of the sequence defined by residues 1 to 353 of SEQ ID NO: 1 as well as corresponding sequences in SEQ ID NO: 6, SEQ ID NO: 8, SEQ ID NO: 10, SEQ ID NO: 12, SEQ ID NO: 14, SEQ ID NO: 16, SEQ ID NO: 19, SEQ ID NO: 20 or SEQ ID NO: 22. In some specific embodiments, the mutated Cys4p consists of the amino acid sequence of SEQ ID NO: 2.

The present disclosure also includes using fragments and/or variants of the mutated Cys4p, provided that such fragments and variants exhibit an increased cystathionine β-synthase activity and/or stability with respect to the wild-type Cys4p. Fragments of the mutated Cys4p refer to a mutated Cys4p having at least one less amino acid residues that the mutated Cys4p. The deletion can occur either at the N-, at the C-terminus or at both the N- and C-terminus of the wild-type protein. Variants of the mutated Cys4p may be one in which one or more of the amino acid residues are substituted with a conserved or non-conserved amino acid residue. A "variant" of the mutated Cys4p can be a conservative variant, or an allelic variant. As used herein, a conservative variant refers to alterations in the amino acid sequence that do not adversely affect the biological functions of the mutated Cys4p. A substitution, insertion or deletion is said to adversely affect the protein when the altered sequence prevents or disrupts a biological function associated with the mutated Cys4p. For example, the overall charge, structure or hydrophobic-hydrophilic properties of the protein can be altered without adversely affecting a biological activity. Accordingly, the amino acid sequence can be altered, for example to render the mutated Cys4p more hydrophobic or hydrophilic, without adversely affecting the biological activities of the mutated Cys4p.

(ii) Mutated Yap1p

Yap1p is a transcription factor involved in S. cerevisiae oxidative stress response. It is a positive transcriptional regulator of the GSH1, GSH2, CYS3 and CYS4 genes. Yeast strains exhibiting increased GSH production where shown to overexpress the transcripts encoding the Yap1p (Nisamedtinov et al., 2010 and Nisamedtinov et al., 2011). Wild-type Yap1p overexpression was also shown to enhance GSH accumulation (Orumets et al., 2012).

The biological activity of the Yap1p is influenced by its subcellular localization: under oxidative stress, the wild-type Yap1p is localized in the nucleus and mediates its biological activity, while when the oxidative stress is reduced, the wild-type Yap1p is translocated in the cytoplasm, thus halting its biological activity (Kuge et al., 1997). The reversible nuclear localization of the wild-type Yap1p is mediated by its C-terminal Cysteine-Rich Domain (CRD). The CRD is capable of forming disulfide bonds between specific cysteine residues which, in some circumstances, conceals the nuclear export sequence of the Yap1p, allowing it to remain active in the nucleus, despite an unchanged expression at the RNA level and even a lower protein level (Kuge et al., 2001 and Kuge et al., 1997).

The genetically modified host cell of the present disclosure can include an heterologous nucleic acid molecule encoding a mutated Yap1p. The mutated Yap1p has, when compared to the wild-type Yap1p, a decreased ability to be translocated from the nucleus to the cytoplasm. After its initial translation in the cytoplasm, the mutated Yap1p is thus substantially, and in some embodiments exclusively, located in the nucleus of the genetically modified host cell (such as, for example, in the nucleus of the genetically modified yeast host cell). The genetically modified host cell is capable of expressing the mutated Yap1p and, when placed in the appropriate conditions, the genetically modified host cell expresses the mutated Yap1p. The mutated Yap1-encoding heterologous nucleic acid molecule can be integrated at one or more copies in the genetically modified host cell (at one or more neutral integration site(s)). The second heterologous nucleic acid molecule can replace one or both copies of the native nucleic acid molecule coding for the native Yap1p. In an embodiment, the genetically modified host cell (and especially the genetically modified yeast host cell) can have one or more copies integrated copies of the heterologous nucleic acid molecule (at one or more neutral integration sites) and in which at least one copy (or both copies) of the native nucleic acid molecule coding for the native Yap1p has been replaced by the first heterologous nucleic acid.

When expressed in the genetically modified host cell (and especially in the genetically modified yeast host cell), the mutated Yap1p has a decreased ability to be translocated from the nucleus in the cytoplasm when compared to the ability of the wild-type Yap1p. In the context of the present disclosure, the wild-type Yap1p refers to a protein having basic leucine zipper transcription factor activity, i.e. a protein capable of modulating the expression of various genes. For example, one of the wild-type Yap1p's transcription factor activity is to increase the expression of the GSH1 and GSH2 genes respectively coding for the γ-glutamylcysteine synthetase protein (Gsh1p) and the glutathione synthetase 2 protein (Gsh2p). In an embodiment, the wild-type Yap1p is encoded by a eukaryotic genome, such as, for example, a yeast genome. FIG. 8 provides an amino acid alignment of wild-type Yap1p from various yeast species. In an embodiment, the wild-type Yap1p has the amino acid sequence of any one of SEQ ID NO: 7, 9, 11, 13, 15, 17, 18 19, 21 or 23. In another embodiment, the wild-type Yap1p is any one of the wild-type Yap1p shown on FIG. 8. In still another embodiment, the wild-type Yap1p corresponds to the consensus sequence shown on FIG. 8.

In still another embodiment, the wild-type Yap1p of the present disclosure can share at least 70%, 75%, 80%, 85%, 90%, 95%, 96%, 97%, 98% or 99% of identity with any one of SEQ ID NO: 7, 9, 11, 13, 15, 17, 18 19, 21 or 23 or the consensus sequence shown on FIG. 8, provided that the wild-type Yap1p is capable of being translocated from the nucleus to the cytoplasm when oxidative stress is reduced. "Identity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, N J (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

As indicated above, the genetically modified host cell of the present disclosure can, in some embodiments, include an heterologous nucleic acid molecule encoding for a mutated Yap1p.

In the context of the present disclosure, a "mutated" Yap1p refers to a protein having a reduced capacity of or lacking the ability of being translocated from the nucleus to the cytoplasm of the host cell, when compared to the ability of the "wild-type" Yap1p. In some embodiments, after its initial translation in the cytoplasm, the mutated Yap1p is constitutively expressed in the nucleus of the host cell. In addition, when compared to the wild-type Yap1p, the mutated Yap1p has one or more amino acid residue difference with the wild-type Yap1p.

In an embodiment, the mutated Yap1p is a fragment of the wild-type Yap1p exhibiting having a reduced capacity of or lacking the ability of being translocated from the nucleus to the cytoplasm of the yeast host cell when compared to the "wild-type" Yap1p. As used in the context of the present disclosure, the term "fragment" refers to a protein having at least one less amino acid residues that the wild-type protein. The deletion can occur either at the N-, at the C- or at both the N- and C-terminus of the wild-type protein. In the context of the present disclosure, when the mutated Yap1p is a fragment of the wild-type Yap1p, it at least comprises the basic region and the leucine zipper of the wild-type Yap1p. For example, the mutated Yap1p can be obtained by deleting (at least partially and in some embodiments entirely) the cysteine-rich domain from the wild-type Yap1p. The cysteine-rich domain of selected Yap1p is shown in FIG. 8. In some embodiments, the mutated Yap1p can have at least at least 100, 200, 300, 400, 500, 600 or more consecutive amino acid residues of the wild-type Yap1p.

In an embodiment, the mutated Yap1p can be obtained by substituting one or more of amino acid residues of the wild-type Yap1p. In an embodiment, the mutated Yap1p does include an amino acid substitution in the cysteine-rich domain of the wild-type Yap1p. The cysteine-rich domain of wild-type Yap1p is illustrated at FIG. 8 and corresponds to residues 604 to 635 of SEQ ID NO: 3. The cysteine-rich domain of the wild-type Yap1p comprises three cysteine residues: a first cysteine residue corresponding to position 604 of SEQ ID NO: 3, a second cysteine residue corresponding to position 626 of SEQ ID NO: 3 and a third cysteine residue corresponding to position 635 of SEQ ID NO: 3. In an embodiment, the mutated Yap1p (in the domain corresponding to the cysteine-rich domain of the Yap1p) has the first cysteine residue (corresponding to residue at position 604 of SEQ ID NO: 3) and the third cysteine residue of the wild-type Yap1p (corresponding to residue at position 635 of SEQ ID NO: 3) and includes a substitution at the second cysteine residue (corresponding to residue at position 626 of SEQ ID NO: 3). The mutated Yap1p can be obtained by substituting the second cysteine residue of the cysteine-rich domain of the wild-type Yap1p by an hydrophilic amino acid residue, such as, for example aspartic acid, leucine, arginine, histidine, glutamic acid, serine, threonine, asparagine, glutamine, lysine, serine, tyrosine, methionine or tryptophan. In another embodiment, the mutated Yap1p can be obtained by substituting the second cysteine residue of the cysteine-rich domain of the wild-type Yap1p by an aspartic acid residue. In an embodiment, the mutated Yap1p comprises the amino acid sequence of SEQ ID NO: 4 or 5. In another embodiment, the mutated Yap1p comprises the amino acid sequence of any one of SEQ ID NO: 7, 9, 11, 13, 15, 17, 18 19, 21 or 23 in which the second cysteine of the cysteine-rich domain (corresponding to residue at position 626 of SEQ ID NO: 3) has been substituted by an hydrophilic amino acid residue (as indicated above), preferably by an aspartic acid residue.

The present disclosure also includes using fragments and/or variants of the mutated Yap1p, provided that such fragments and variants exhibit a reduced ability of or lacking the ability of being translocated from the nucleus to the cytoplasm of the host cell when compared to the wild-type Yap1p. Fragments of the mutated Yap1p refer to a mutated Yap1p having at least one less amino acid residues that the mutated Yap1p. The deletion can occur either at the N-, at the C- or at both the N- and C-terminus of the wild-type protein. Variants of the mutated Yap1p may be one in which one or more of the amino acid residues are substituted with a conserved or non-conserved amino acid residue. A "variant" of the mutated Yap1p can be a conservative variant, or an allelic variant. As used herein, a conservative variant refers to alterations in the amino acid sequence that do not adversely affect the biological functions of the mutated Yap1p. A substitution, insertion or deletion is said to adversely affect the protein when the altered sequence prevents or disrupts a biological function associated with the mutated Yap1p. For example, the overall charge, structure or hydrophobic-hydrophilic properties of the protein can be altered without adversely affecting a biological activity. Accordingly, the amino acid sequence can be altered, for example to render the mutated Yap1p more hydrophobic or hydrophilic, without adversely affecting the biological activities of the mutated Yap1p.

(iii) Heterologous Threonine Aldolase (Gly1p)

Glycine is required for the production of GSH. The L-threonine aldolase protein (also referred to as Gly1p) catalyzes the removal of acetaldehyde from threonine to generate glycine.

The genetically modified host cell of the present disclosure (and especially the genetically modified yeast host cell of the present disclosure) can include an heterologous nucleic acid molecule coding for an heterologous Gly1p. Such genetically modified host cell is thus capable of expressing the heterologous Gly1p and, when placed in the appropriate conditions, the genetically modified host cell expresses the heterologous Gly1p which can favor an increase in total thiols (and GSH production), optionally in combination with the expression of the heterologous Gsh1p and/or the mutated Cys4p. The Gly1p-encoding heterologous nucleic acid molecule can be integrated in one or more copies in the genetically modified host cell (at one or more neutral integration site(s)). In an embodiment, the genetically modified host cell (and especially the genetically modified yeast host cell) can have one or more copies (e.g., at least two, three or four) integrated copies of the Gly1p-encoding heterologous nucleic acid molecule (at one or more neutral integration sites).

In an embodiment, the heterologous Gly1p has the amino acid sequence of any one of SEQ ID NO: 24, 25, 26, 27, 28, 29, 30, 31 or 32. In another embodiment, the heterologous Gly1p is any one of the heterologous Gly1p shown on FIG. 9. In still another embodiment, the heterologous Gly1p corresponds to the consensus sequence shown on FIG. 9.

The present disclosure also concerns variants of the heterologous Gly1p may be one in which one or more of the amino acid residues are substituted with a conserved or non-conserved amino acid residue. A "variant" of the heterologous Gly1p can be a conservative variant, or an allelic variant. As used herein, a conservative variant refers to alterations in the amino acid sequence that do not adversely affect the biological functions of the heterologous Gly1p. A substitution, insertion or deletion is said to adversely affect the protein when the altered sequence prevents or disrupts a biological function associated with the heterologous Gly1p. For example, the overall charge, structure or hydrophobic-hydrophilic properties of the protein can be altered without adversely affecting a biological activity. Accordingly, the amino acid sequence can be altered, for example to render the heterologous Gly1p more hydrophobic or hydrophilic, without adversely affecting the biological activities of the heterologous Gly1p.

In still another embodiment, the variant of the heterologous Gly1p of the present disclosure can share at least 60%, 65%, 70%, 75%, 80%, 85%, 90%, 95%, 96%, 97%, 98% or 99% of identity with any one of SEQ ID NO: 24, 25, 26, 27, 28, 29, 30, 31 or 32 with the consensus sequence shown on FIG. 9, provided that the heterologous Gly1p exhibits threonine aldolase activity. "Identity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, N J (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

In an embodiment, the heterologous Gly1p is a fragment of the wild-type Gly1p exhibiting an threonine aldolase activity. As used in the context of the present disclosure, the term "fragment" refers to a protein having at least one less amino acid residues that the wild-type protein. The deletion can occur either at the N-, at the C- or at both the N- and C-terminus of the wild-type heterologous Gly1p. In the context of the present disclosure, when the heterologous Gly1p is a fragment of the wild-type Gly1p, it at least comprises the catalytic domain of the wild-type Gly1p. In some embodiments, the fragment of the heterologous Gly1p can have at least at least 250, 260, 270, 280, 290, 300, 310, 320, 330, 340, 350 or more consecutive amino acid residues of the wild-type Gly1p.

(iv) Additional Heterologous Nucleic Acid Molecules

The genetically modified host cell comprises at least one of the first heterologous nucleic acid molecule encoding for the mutated Cys4p, the second heterologous nucleic acid molecule encoding for the mutated Yap1p and/or the third heterologous nucleic acid molecule encoding for the heterologous Gly1p. In a further embodiment, the genetically modified host cell comprises the first heterologous nucleic acid molecule (coding for a mutated Cys4p) and at least one of the second nucleic acid molecule (coding for a mutated Yap1p) or the third heterologous nucleic acid molecule (coding for a threonine aldolase protein (Gly1p)). In an embodiment, the genetically modified host cell comprises both the first heterologous nucleic acid molecule coding for the mutated Cys4p and the second heterologous nucleic acid molecule coding for the mutated Yap1p. In a further embodiment, the genetically modified host cell comprises both the second heterologous nucleic acid molecule coding for the mutated Cys4p and the third heterologous nucleic acid molecule coding for the heterologous Gly1p. In another embodiment, the genetically modified host cell comprises both the second heterologous nucleic acid molecule coding for the mutated Yap1p and the third heterologous nucleic acid molecule coding for the heterologous Gly1p. In yet another embodiment, the genetically modified host cell comprises the first heterologous nucleic acid molecule encoding for the mutated Cys4p, the second heterologous nucleic acid molecule encoding for the mutated Yap1p and the third heterologous nucleic acid molecule encoding for the heterologous Gly1p.

In the embodiments in which more than one heterologous nucleic acid molecules are present in the genetically modified host cell (such as the genetically modified yeast host cell), each of the heterologous nucleic acid molecules can be integrated (in one or more copies) at neutral integration site(s) and/or replace one or both copies of the nucleic acid molecule coding for the native (wild-type) nucleic acid molecules (for example the native nucleic acid molecule coding for Cys4p or Yap1p). For example, the first, second and third heterologous nucleic acid molecule can both be integrated at one or more copies in the genetically modified host cell (at one or more neutral integration site(s)). In such embodiment, the neutral integration sites can be the same or different. In another example, the first heterologous nucleic acid molecule can replace one or more copies of the native nucleic acid molecule coding for the native Cys4p and one or more copies of the second heterologous nucleic acid molecule can be integrated at one or more neutral integration site(s). In still another example, the genetically modified host cell (and especially the genetically modified yeast host cell) can have one or more copies integrated copies of the first and the second heterologous nucleic acid molecules (at one or more neutral integration sites) and in which at least one copy (or both copies) of the native nucleic acid molecule coding for the native Cys4p has been replaced by the first heterologous nucleic acid. In still another example, the first heterologous nucleic acid molecule can be integrated at one or more copies in the genetically modified host cell (at one or more neutral integration site(s)) while the second nucleic acid molecule can replace one or both copies of the nucleic acid molecule coding for the native wild-type Yap1p. The first heterologous nucleic acid molecule can replace one or more copies of the native nucleic acid molecule coding for the native Cys4p and the second heterologous nucleic acid molecule can replace one or more copies of the native nucleic acid molecule coding for the native Yap1p. In still another example, the genetically modified host cell (and especially the genetically modified yeast host cell) can have one or more copies integrated copies of the first heterologous nucleic acid molecule (at one or more neutral integration sites) and in which at least one copy (or both copies) of the native nucleic acid molecule coding for the native Cys4p has been replaced by the first heterologous nucleic acid and at least one copy (or both copies) of the native nucleic acid molecule coding for the native Yap1p has been replaced by the second heterologous nucleic acid molecule. In still a further example, the genetically modified host cell (and especially the genetically modified yeast host cell) can have one or more copies integrated copies of the first and of the second heterologous nucleic acid molecule (at one or more neutral integration sites) and in which at least one copy (or both copies) of the native nucleic acid molecule coding for the native Cys4p has been replaced by the first heterologous nucleic acid and at least one copy (or both copies) of the native nucleic acid molecule coding for the native Yap1p has been replaced by the second heterologous nucleic acid molecule.

The genetically modified host cell can include further heterologous nucleic acid molecules encoding additional genes for favoring the production and accumulation of glutathione. For example, the genetically modified host cell can include a fourth nucleic acid molecule coding for the Gsh1p and/or a fifth nucleic acid molecule coding for the Gsh2p. In yet another example, the genetically modified host cell can include both the fourth nucleic acid molecule coding for the Gsh1p and the fifth nucleic acid molecule coding for the Gsh2p. Each of the heterologous nucleic acid molecules of the recombinant host cell can be present in one or more copies in the genetically modified host cell. For example, each of the heterologous nucleic acid molecules can be present in one, two, three or four copies in the genetically modified host cell. The number of copies of each of the heterologous nucleic acid molecule is independently selected.

In an embodiment, the genetically modified host cell comprises at least two and preferably at least four copies of the first heterologous nucleic acid molecule encoding the mutated Cys4p (integrated at a neutral position) and wherein at least one and preferably two copies of the native nucleic acid molecule encoding the wild-type Yap1p has been replaced by the second heterologous nucleic acid molecule encoding the mutated Yap1. In another embodiment, the genetically modified host cell comprises at least two and preferably at least four copies of the first heterologous nucleic acid molecule encoding the mutated Cys4p (integrated at a neutral position) and at least two and preferably at least four copies of the second heterologous nucleic acid molecule coding for the heterologous Gly1p. In such embodiments, it may be necessary to include at least two and preferably four copies of each of the third heterologous nucleic acid molecule coding for the Gsh1p and the fourth heterologous nucleic acid molecule coding for the Gsh2p.

In an embodiment, the genetically modified host cell (and particularly the genetically modified yeast host cell) bears (in an integrated form) the second, the third, the fourth and the fifth heterologous nucleic acid molecules. Both copies of the native nucleic acid molecule coding for the native wild-type Yap1p are respectively replaced by the second heterologous nucleic acid molecule. In addition, the second nucleic acid molecule is integrated in multiple copies (preferably four) in the genome of the genetically modified host cell. Further, both the third and the fourth nucleic acid molecules are each integrated in multiple copies (preferably four) in the genome of the genetically modified host cell.

In a further embodiment, the genetically modified host cell (and particularly the genetically modified yeast host cell) bears (in an integrated form) the first, the second, the third, the fourth and the fifth heterologous nucleic acid molecules. Both copies of each of the native nucleic acid molecule coding for the native wild-type Cys4p and the native wild-type Yap1p are respectively replaced by the first and the second heterologous nucleic acid molecule. In addition, the second nucleic acid molecule is integrated in multiple copies (preferably four) in the genome of the genetically modified host cell. Further, both the third and the fourth nucleic acid molecules are each integrated in multiple copies (preferably four) in the genome of the genetically modified host cell.

In an embodiment, the genetically modified host cell does not include an heterologous nucleic acid molecule coding for a wild-type or mutated cystathionine γ-lyase protein (Cys3p), but nevertheless does express a native cystathionine γ-lyase protein (Cys3p).

Process for Making Genetically Modified Host Cells

The genetically modified host cell can be prepared by using conventional molecular biology tools and teaches. In the context of the present disclosure, the process for making the genetically modified host cell comprises introducing a first heterologous nucleic acid molecule coding for the mutated Cys4p, a second heterologous nucleic acid molecule coding for the mutated Yap1p and/or a third heterologous nucleic acid molecule coding for the heterologous Gly1p. Optionally, the process can also include introducing a fourth heterologous nucleic acid molecule coding for the Gsh1p and/or a fifth heterologous nucleic acid molecule coding for the Gsh2p. In an embodiment, the process does not include (e.g., excludes) the introduction of an heterologous nucleic acid molecule coding for a wild-type or mutated cystathionine γ-lyase protein (Cys3p), but nevertheless does express a native cystathionine γ-lyase protein (Cys3p).

Each of the heterologous nucleic acid molecule can be independently integrated or independently replicating in the genetically modified host cell. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies in the host cell's genome. Alternatively, the heterologous nucleic acid molecule can be independently replicating from the host cell's genome. In such embodiment, the heterologous nucleic acid molecule can be stable and self-replicating.

In an embodiment, at least one heterologous nucleic acid molecule is integrated in the genome of the genetically modified host cell. In still another embodiment, all heterologous nucleic acid molecules are integrated in the genome of the genetically modified host cell.

Each of the heterologous nucleic acid molecule can either be integrated at a neutral integration site (the same or different sites) or designed to specifically replace the corresponding native nucleic acid molecule encoding the corresponding wild-type protein.

In an embodiment, it is contemplated that one or more heterologous nucleic acid molecules intended to be introduced in the genetically modified host cell be codon optimized, at least partially or entirely, prior to its introduction in the intended recipient host cell.

In an embodiment, when present, the first heterologous nucleic acid molecule coding for the mutated Cys4p is integrated at a neutral integration site. When present in multiple copies (two, three or four copies for example), each of the first heterologous nucleic acid molecules can be integrated at the same or at different neutral integration sites. Alternatively or in combination, the first heterologous nucleic acid molecule can replace one or both copies of the nucleic acid molecule coding for the wild-type Cys4p.

In yet another embodiment, when present, the second heterologous nucleic acid molecule coding for the mutated Yap1p can replace one or preferably both copies of the nucleic acid molecule coding for the wild-type Yap1p in the yeast host cell. Alternatively or in combination, the second heterologous nucleic acid molecule can be integrated at a neutral integration site (which can be the same or different than the integration site(s) for the first heterologous nucleic acid molecule). When present in multiple copies (two, three or four for example), each of the second heterologous nucleic acid molecules can be integrated at the same or different integration sites (which can be the same or different than the integration site(s) for the first heterologous nucleic acid molecule).

In still a further embodiment, when present, the third heterologous nucleic acid molecule (coding for the Gly1p) can be integrated at the same or different neutral integration sites (which can be the same or different than the integration site(s) for the first or second heterologous nucleic acid molecules).

In an embodiment, when present, the fourth heterologous nucleic acid molecule (coding for the Gsh1p) and the fifth heterologous nucleic acid molecule (coding for the Gsh2p) can be integrated at the same or different neutral integration sites (which can be the same or different than the integration site(s) for the first or second heterologous nucleic acid molecules).

In still another embodiment, the process can include integrating one or more copies of the first heterologous nucleic acid molecule coding for the mutated Cys4p at one or more neutral integration sites and replacing one or preferably both copies of the nucleic acid molecule coding for the wild-type Yap1p in the host cell (a yeast host cell for example) by the second heterologous nucleic acid molecule coding for the mutated Yap1p. In such embodiment, the process can also include integrating one or more copies of the third heterologous nucleic acid molecule coding for the threonine aldolase (Gly1p), the fourth heterologous nucleic acid molecule coding for the Gsh1p and the fifth nucleic acid molecule coding for the Gsh2p at the same or different neutral integration sites.

The heterologous nucleic acid molecules can be introduced in the host cell using a vector. A "vector," e.g., a "plasmid", "cosmid" or "YAC" (yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

When the heterologous nucleic acid molecule is intended to be integrated at a neutral integration site, it may be necessary to include a promoter on the heterologous nucleic acid molecule. In such embodiment, the promoter and the nucleic acid molecule coding for the protein of interest are operatively linked to one another. In the context of the present disclosure, the expressions "operatively linked" or "operatively associated" refers to fact that the promoter is physically associated to the nucleotide acid molecule coding for the heterologous protein in a manner that allows, under certain conditions, for expression of the heterologous protein from the nucleic acid molecule. In an embodiment, the promoter can be located upstream (5') of the nucleic acid sequence coding for the heterologous protein. In the context of the present disclosure, one or more than one promoter can be included in the heterologous nucleic acid molecule. When more than one promoter is included in the heterologous nucleic acid molecule, each of the promoters is operatively linked to the nucleic acid sequence coding for the heterologous protein.

When the heterologous nucleic acid molecule is intended to be integrated at a neutral integration site, it may be necessary to include a terminator on the heterologous nucleic acid molecule. In such embodiment, the terminator and the nucleic acid molecule coding for the protein of interest are operatively linked to one another. In the context of the present disclosure, the expressions "operatively linked" or "operatively associated" refers to fact that the terminator is physically associated to the nucleotide acid molecule coding for the heterologous protein in a manner that allows, under certain conditions, for marking the end of the coding sequence of the heterologous protein. In an embodiment, the terminator can be located upstream (3') of the nucleic acid sequence coding for the heterologous protein. In the context of the present disclosure, one or more than one terminator can be included in the heterologous nucleic acid molecule. When more than one terminator is included in the heterologous nucleic acid molecule, each of the terminators is operatively linked to the nucleic acid sequence coding for the heterologous protein.

Process for Making Glutathione

The present disclosure also relates to processes for making glutathione based on the use of the genetically modified host cells described herein or obtained by the process describes herein. Generally, the process comprises fermenting a substrate with the genetically modified host cell so as to obtain a fermented mixture comprising glutathione. As used in the context of the present disclosure, the term "substrate" refers to a source of carbon for the host cell that can be used during fermentation. The substrate is preferably in a liquid form and can optionally be supplemented with carbohydrates (glucose for example), a sugar alcohol (glycerol for example), vitamins, minerals, and/and amino acids (cysteine and/or glycine for example). When the genetically modified host cell is a genetically modified yeast host cell, such substrate can be, without limitation, a chemically defined medium or a non-chemically define medium such as molasses (obtained from sugar beet or sugar cane), etc. The fermentation is conducted under circumstances allowing the expression of the heterologous nucleic acid molecule(s) and the accumulation of glutathione.

The process includes fermenting the substrate with the genetically modified host cell to obtain a fermented mixture comprising GSH. The term "fermented mixture" refers to the fermented substrate, the genetically modified host cells and the metabolites produced during the fermentation by the genetically modified host cells. The fermented mixture can be further processed by various downstream operations. For example, an extract of the fermented can be obtained, and such extract can be optionally dehydrated or dried. In the context of the present disclosure, in the extract of the fermented mixture, the genetically modified host cells can be inactivated and whole (i.e., the genetically modified host cell is relatively intact) or can be further fractionated (i.e., the genetically modified host cell's is intentionally ruptured). When the genetically modified host cell is a yeast, a yeast extract can be produced from the fermented mixture. For example, a yeast extract can be obtained by hydrolyzing or autolyzing the fermented mixture (chemically, thermally and/or enzymatically) and subsequently separating (isolating) the insoluble from the soluble fraction (corresponding to the yeast extract). The yeast extract consists of the hydrolyzed genetically modified host cells. The fermented mixture can be hydrolyzed to provide a hydrolysate which can be optionally dehydrated or dried. When the genetically modified yeast host cell is a yeast, a yeast hydrolysate can be provided from the fermented mixture. A yeast hydrolysate can be obtained by allowing the lysis of the of the genetically modified yeast cells with their own enzymes. The yeast hydrolysate usually contains both a soluble and a non-soluble fraction. In some embodiments, the process further comprising purifying the genetically modified host cells (such as, for example, the genetically modified yeast host cells) from the fermented mixture. The purified genetically modified host cells can be processed (divided into aliquots, diluted, frozen, filtrated and/or lyophilized) so as to maintain their cellular integrity and allow their subsequent proliferation. Alternatively, the genetically modified host cells (such as, for example, the genetically modified yeast host cells) can be inactivated (e.g., killed) prior to being processed (divided into aliquots, diluted, frozen, filtrated and/or lyophilized). Optionally, the glutathione can be purified (at least partially and, in some embodiments, completely).

The fermented mixtures or the various products that can be obtained thereof can be advantageously used in many applications, such as, for example, in pharmaceutical applications, in cosmetic applications as well as in animal and human food applications (nutrition, bread making and wine making for example). Glutathione and glutathione-comprising products can be formulated for oral administration, for topical administration or for parenteral administration.

The present invention will be more readily understood by referring to the following examples which are given to illustrate the invention rather than to limit its scope.

Example I—Genetically Modified *Saccharomyces cerevisiae* Host Cells

Gene cassettes (including native promoters and terminators) were amplified by polymerase chain reaction and integrated at the indicated target sites (Table 1) by homologous recombination.

TABLE 1

Description of the various strains of Example I

| Strain designation | Genotype |
| --- | --- |
| Parental strain | Wild type (not genetically modified) |
| SIL005 | ΔYLR296W::CYS4 (2 copies) |
| SIL016 | ΔYLR296W::CYS4-CYS3 (2 copies of each) |
| SIL064 | ΔCYS4::CYS4.353 |
| SIL010 | ΔYLR296W::CYS4.353 (2 copies) |
| SIL019 | ΔYLR296W::CYS4.353 (2 copies) |
| | ΔFCY1::GSH1-GSH2 (2 copies each) |
| SIL020 | ΔYLR296W::CYS4.353-CYS3 (2 copies of each) |
| | ΔFCY1::GSH1-GSH2 (2 copies each) |
| SIL022 | ΔYAP1::YAP1$^{C626D}$ |
| SIL024 | ΔYAP1::YAP1$^{C626D}$ |
| | ΔFCY1::GSH1-GSH2 (2 copies each) |
| SIL030 | ΔYLR296W::CYS4.353 (2 copies) |
| | ΔYAP1::YAP1$^{C626D}$ |
| SIL078 | ΔYLR296W::CYS4.353 (2 copies) |
| | ΔCYS4::CYS4.353 |
| | ΔYAP1::YAP1$^{C626D}$ |
| SIL043 | ΔYLR296W::CYS4.353 (2 copies) |
| | ΔYAP1::YAP1$^{C626D}$ |
| | ΔFCY1::GSH1-GSH2 (2 copies each) |
| SIL070 | ΔYLR296W::CYS4.353 (2 copies) |
| | ΔYAP1::YAP1$^{C626D}$ |
| | ΔFCY1::GSH1-GSH2-GSH1-GSH2 (4 copies each) |
| SIL073 | ΔYLR296W::CYS4.353 (2 copies) |
| | ΔYAP1::YAP1$^{C626D}$ |
| | ΔFCY1::GSH1-GSH2-YAP1$^{C626D}$-GSH1-GSH2 (4 copies of GSH1 &GSH2, 2 copies of YAP1$^{C626D}$) |

TABLE 1-continued

Description of the various strains of Example I

| Strain designation | Genotype |
| --- | --- |
| SIL085 | ΔYLR296W::CYS4.353 (2 copies) |
| | ΔYAP1::YAP1$^{C626D}$ |
| | ΔCYS4::CYS4.353 |
| | ΔFCY1::GSH1-GSH2-YAP1$^{C626D}$-GSH1-GSH2 (4 copies of GSH1 &GSH2, 2 copies of YAP1$^{C626D}$) |
| SIL068 | ΔYAP1::YAP1$^{C626D}$ |
| | ΔFCY1::GSH1-GSH2-YAP1$^{C626D}$-GSH1-GSH2-YAP1$^{C626D}$ (4 copies of each) |
| SIL090 | ΔYAP1::YAP1$^{C626D}$ |
| | ΔCYS4::CYS4.353 (2 copies) |
| | ΔFCY1::GSH1-GSH2-YAP1$^{C626D}$-GSH1-GSH2-YAP1$^{C626D}$ (4 copies of each) |
| SIL061 | ΔCYS4::CYS4.353 |
| | ΔFCY1::pPMA1-GSH1-pPMA1-GSH1 (4 copies) |
| | ΔAPT2::pPMA1-GSH1-pPMA1-GSH1 (4 copies) |
| | ΔSTR2::pGPM1-GSH2 (2 copies) |
| SIL143 | ΔCYS4::CYS4.353 |
| | ΔFCY1::pPMA1-GSH1-pPMA1-GSH1 (4 copies) |
| | ΔAPT2::pPMA1-GSH1-pPMA1-GSH1 (4 copies) |
| | ΔSTR2::pGPM1-GSH2 (2 copies) |
| | ΔYOL085C::pGPD1-GLY1-pGPD1-GLY1 (4 copies) |

Determination of Thiol Content.

Five milliliter-cultures of strains containing these constructs, alone or combined, were grown for 18 hours in defined medium in shake flasks at 32° C., 200 rpm. Measurement of total thiols using Ellman's reagent was then performed.

The strain yielded 1.2 times more thiols upon addition of two copies of CYS4, but the effect was significantly more pronounced when using CYS4.353, with a 1.7-fold thiols content increase. Constitutive expression of Yap1p increased the total thiols content of 1.3-fold, and of 1.8-fold when combined with CYS4.353.

Additional strains have been designed which express more copies of a constitutively active Yap1p, more copies of CYS4.353, as well as extra copies of GSH1 and GSH2, three genes positively regulated by Yap1p. GSH1 and GSH2 were added at neutral integrations sites. All genes were under the control of their native promoters and terminators. The resulting total thiols (apparent GSH) increase compared to the parental strain is shown in FIG. 1 and indicated in table 2.

TABLE 2

Total thiols increase of various constructs when compared to the parental strain.

| Strain designation | % increase (when compared with parental strain) |
| --- | --- |
| SIL005 | 19% |
| SIL016 | 12% |
| SIL064 | 20% |
| SIL010 | 69% |
| SIL019 | 67% |
| SIL020 | 51% |
| SIL022 | 24% |
| SIL024 | 67% |
| SIL030 | 80% |
| SIL078 | 78% |
| SIL043 | 106% |
| SIL070 | 127% |
| SIL073 | 185% |
| SIL085 | 194% |
| SIL068 | 207% |
| SIL090 | 260% |

Figure 2:
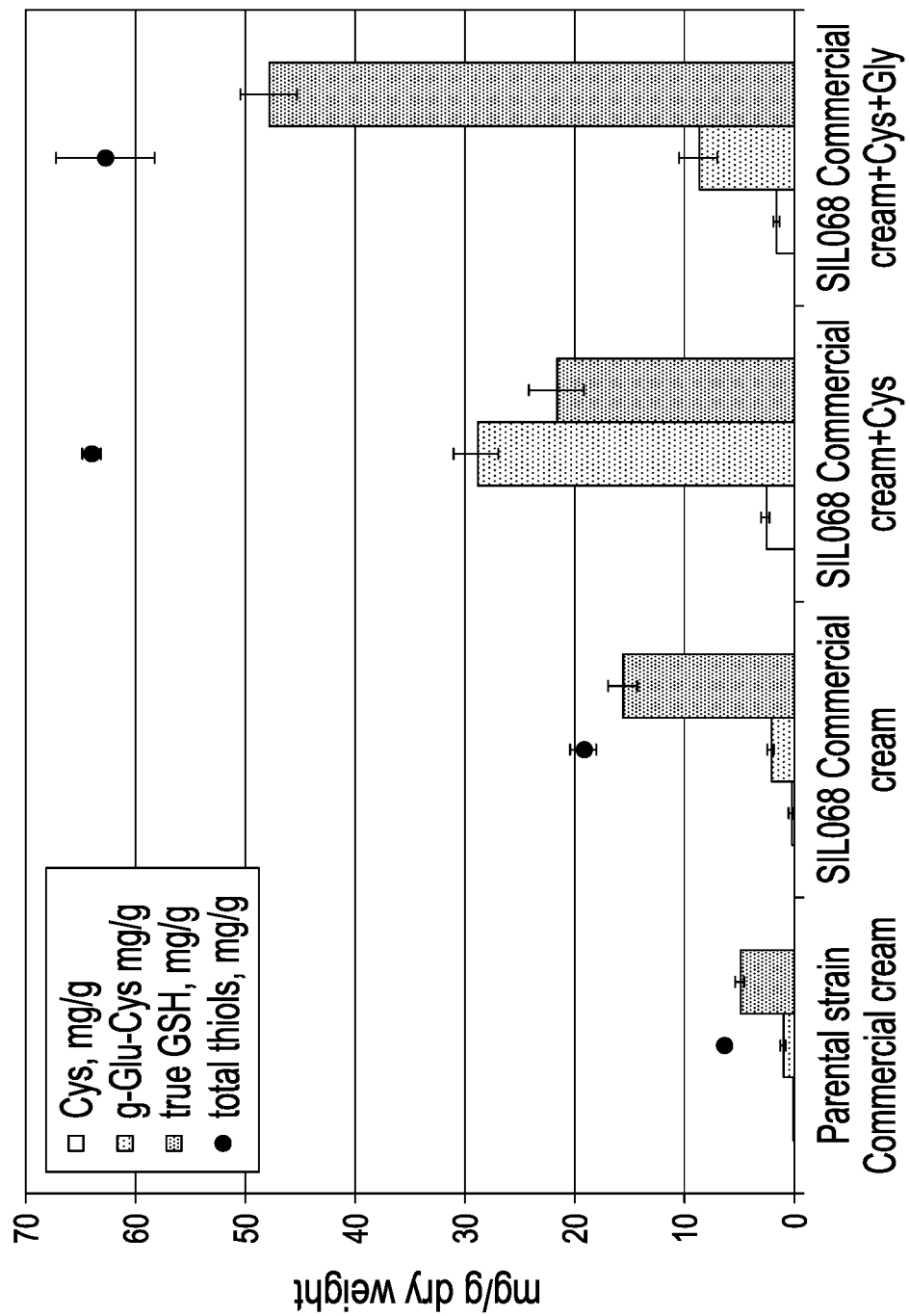
FIG. 2 provides the true glutathione (true GSH), cysteine (Cys), γ-L-glutamyl-L-cysteine (γ-GC or g-Glu-Cys) and total thiol content of *S. cerevisiae* strain SIL068 grown in molasses in a 20 L fermenter. Values are provided as mg/g of dry weight in function of fermentation conditions. Values are average of duplicates or triplicates.

Inactive dry yeast was produced from the strain SIL068 after growth in industrial 20 L fermenters, with no addition (commercial cream), with the addition of cysteine only (commercial cream +Cys) or with the addition of both cysteine and glycine (commercial cream +Cys+Gly). To precisely measure the free cysteine, γ-GC and true GSH distribution, the thiols were quantified using HPLC, and results are displayed in FIG. 2. Interestingly, SIL068 grown in industrial conditions in molasses displays a true GSH content of 1.6% (total thiols of 1.9%). Upon addition of cysteine and glycine, the true GSH could be increased up to 4.8% (total thiols of 6.3%).

Additional strains were constructed which contained additional copies of CYS3, along with extra copies of CYS4 (SIL016) or CYS4.353 (SIL020) (Table 1). Such strains did not display increased apparent GSH content compared to those overexpressing solely CYS4 or CYS4.353 (FIG. 1, Table 2).

Inactive dry yeast (IDY) was produced from commercial creams propagated with cysteine or with a cysteine and glycine addition. The IDY was tested for its bread dough relaxant effect in baguettes using a standard no time dough recipe. The relaxing effect is assessed by measuring the baguettes (the higher the dough relaxing effect is, the longer the baguette is).

The SIL068 IDY1 (obtained by making an inactive dry yeast with the SIL068 strain propagated in cysteine and glycine) used for the test was measured at 4.92% true GSH, for a total thiols of 6%. The SIL068 IDY2 (obtained by making an inactive dry yeast with the SIL068 strain propagated in cysteine only) was measured at 1.9% true GSH, for a total thiols of 5.7%. The amount of IDY used was thus adjusted accordingly to reflect the amount of total thiols from the Fermaid-SR™ commercial product, which specific lot was measured at 17% total thiols.

Figure 3:
FIG. 3 illustrates the effect of total thiols and true GSH on the baguette's length in a baking test. Baguettes were obtained with (1) no additive (control), (2) 40 ppm L-cysteine, (3) 0.25% Fermaid-SR™, (4) 0.5% Fermaid-SR™, (5) 0.071% SIL068 IDY1, (6) 0.14% SIL068 IDY1, (7) 0.083% SIL068 IDY2 or (8) 0.167% SIL068 IDY2.

As seen on FIG. 3 and in Table 3 below, both SIL068 IDYs have dough relaxing effect proportional to their total thiols content. The dough relaxation performance of the sample seems linked to its apparent GSH content.

TABLE 3

Measurement of the length of baguettes supplemented with the commercial Fermaid-SR™ additive, the SIL068 IDY1 or the SIL068 IDY2. Results correspond to the mean baguette length for four baguettes (generated from the same dough).

| Additive | Baguette length (in cm) |
| --- | --- |
| None (control) | 42.25 (±0.96) cm |
| 40 ppm L-cysteine | 50.75 (±1.5) cm |
| 0.25% Fermaid-SR™ | 50 (±1.83) cm |
| 0.5% Fermaid-SR™ | 56 (±0.82) cm |
| 0.071% SIL068 IDY1 | 54.75 (±1.5) cm |
| 0.14% SIL068 IDY1 | >59 (±1.5) cm |
| 0.083% SIL068 IDY2 | 56 (±0.82) cm |
| 0.167% SIL068 IDY2 | >59 (±0.5) cm |

Figure 4:
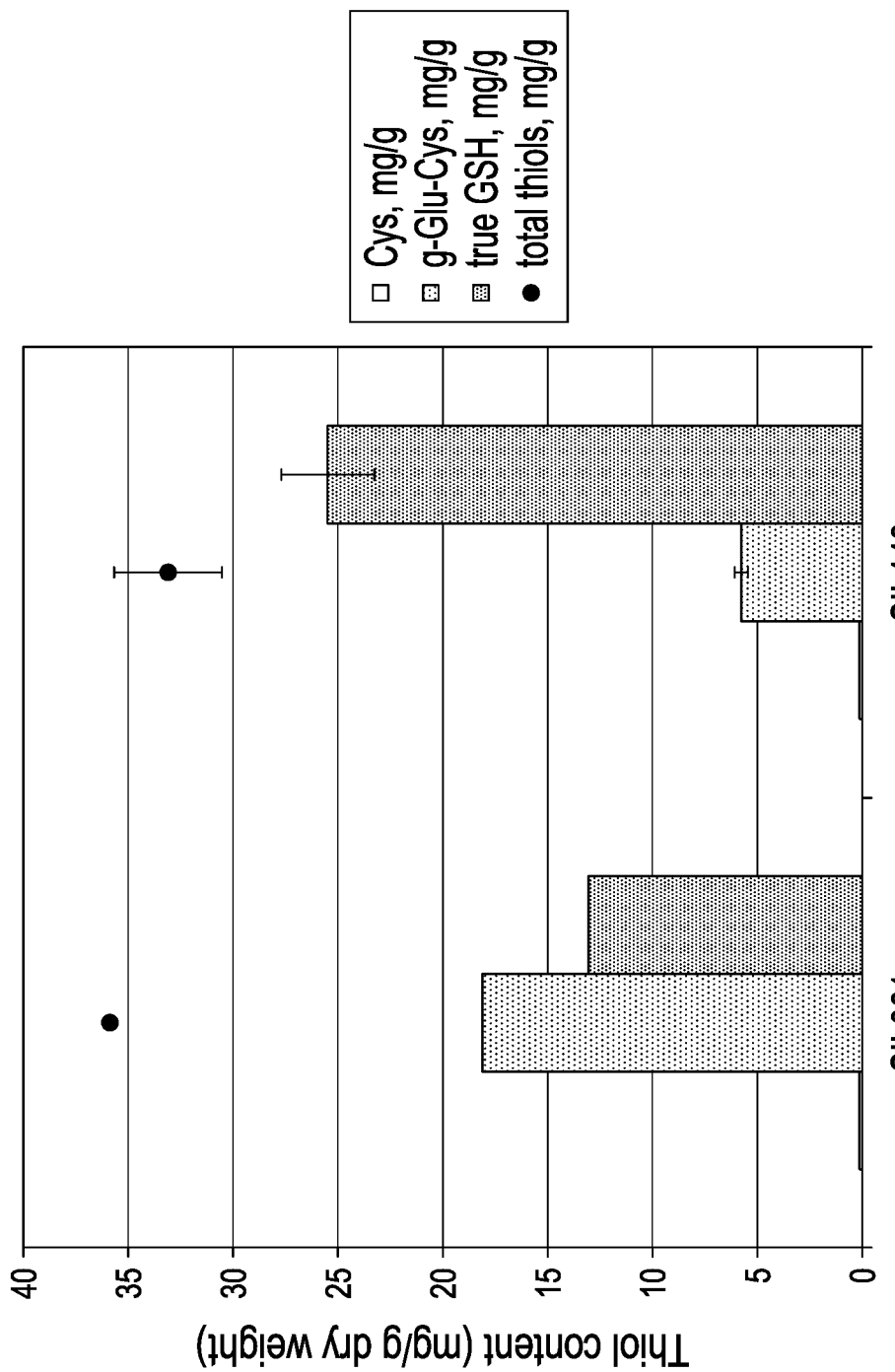
FIG. 4 provides cysteine (Cys), γ-L-glutamyl-L-cysteine (g-GC), true GSH and total thiol content of *S. cerevisiae* strains SIL061 (n=1) and SIL143 (n=2) grown on minimal medium supplemented with cysteine. Values are provided as mg/g of dry weight in function of fermentation conditions.

In order to further increase the GSH content in the recombinant host cell, the role of GLY1 was further investigated. Genetically-modified yeast strain SIL061 contains 8 extra copies of GSH1 under the control of a constitutive promoter, 2 extra copies of GSH2 under the control of a constitutive promoter, and 2 copies of CYS4.353 under the control of the endogenous CYS4 promoter. SIL061 was further engineered to contain 4 additional copies of GLY1, under the control of a constitutive promoter (SIL143). When grown in minimal media with the addition of 1 mM of cysteine, the extra copies of GLY1 resulted in the conversion of more than 60% of the intermediate γ-GC to GSH (FIG. 4).

Example II—Genetically Modified *Pichia pastoris* Host Cells

To determine if the genetic modifications of Example I could be applied to other genus, genetically-modified *P. pastoris* host cells have been made. Gene cassettes (including native promoters and terminators) were amplified by polymerase chain reaction and integrated at the indicated target sites (Table 2) by homologous recombination.

TABLE 2

Description of the various *Pichia pastoris* strains of Example II

| Strain designation | Genotype |
| --- | --- |
| X33 | *Pichia pastoris* wild type (not genetically modified) |
| SIL148 | CYS4::CYS4-BleoR (1 copy) |
| SIL150 | CYS4::CYS4.340-BleoR (1 copie) |
| SIL151 | YAP1:: YAP1-BleoR (1 copie) |
| SIL153 | YAP1:: YAP1.C414D- BleoR (1 copie) |

Five milliliter-cultures of *P. pastoris*, wild-type or genetically modified, were grown for 18 hours in defined medium in shake flasks at 32° C., 200 rpm. Thiols were derivatized using Ellman's reagent and quantified by HPLC, as described in Example I.

Figure 5:
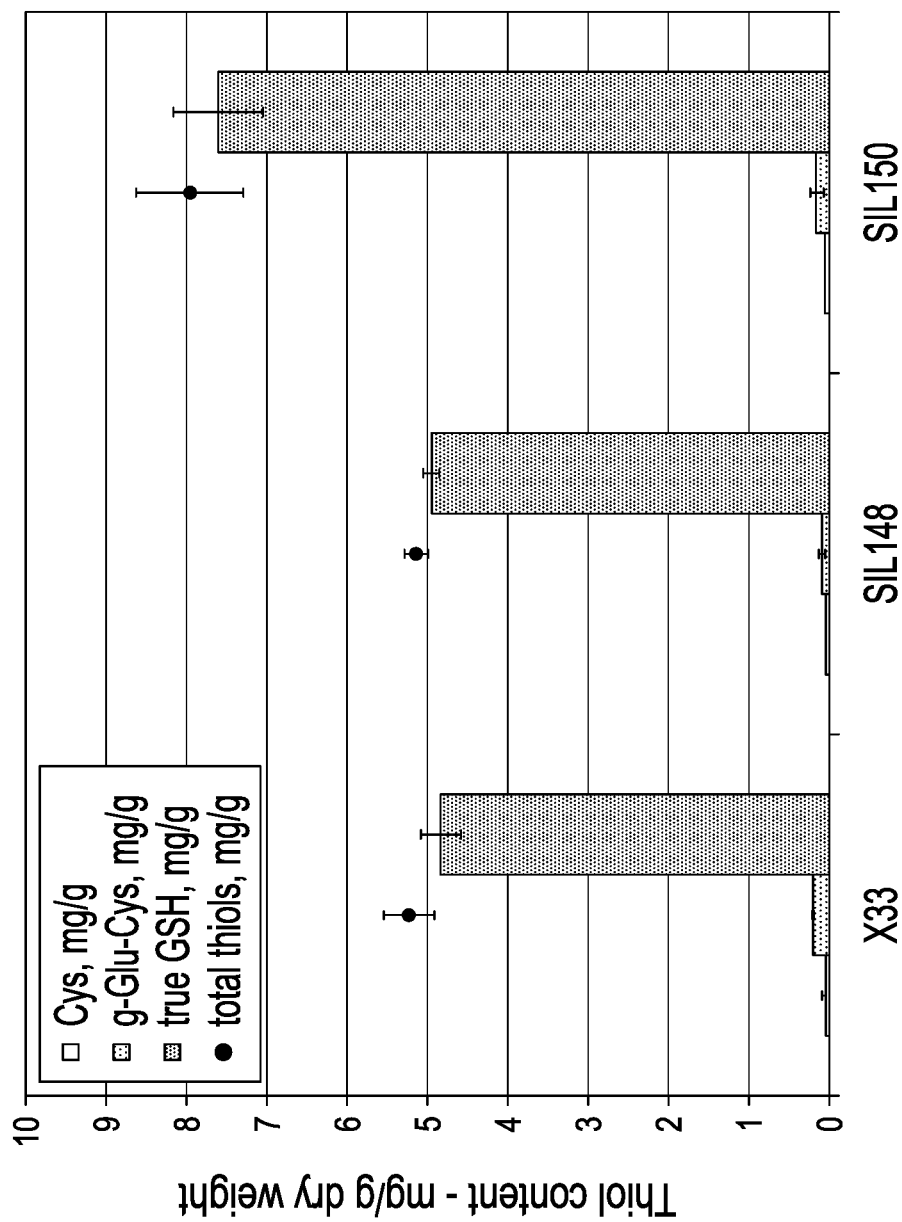
FIG. 5 provides cysteine (Cys), γ-L-glutamyl-L-cysteine (g-GC), true GSH and total thiol content of *P. pastoris* strains X33, SIL148 and SIL150 grown on minimal medium supplemented with cysteine (n=2). Values are provided as mg/g of dry weight in function of fermentation conditions.
Figure 6:
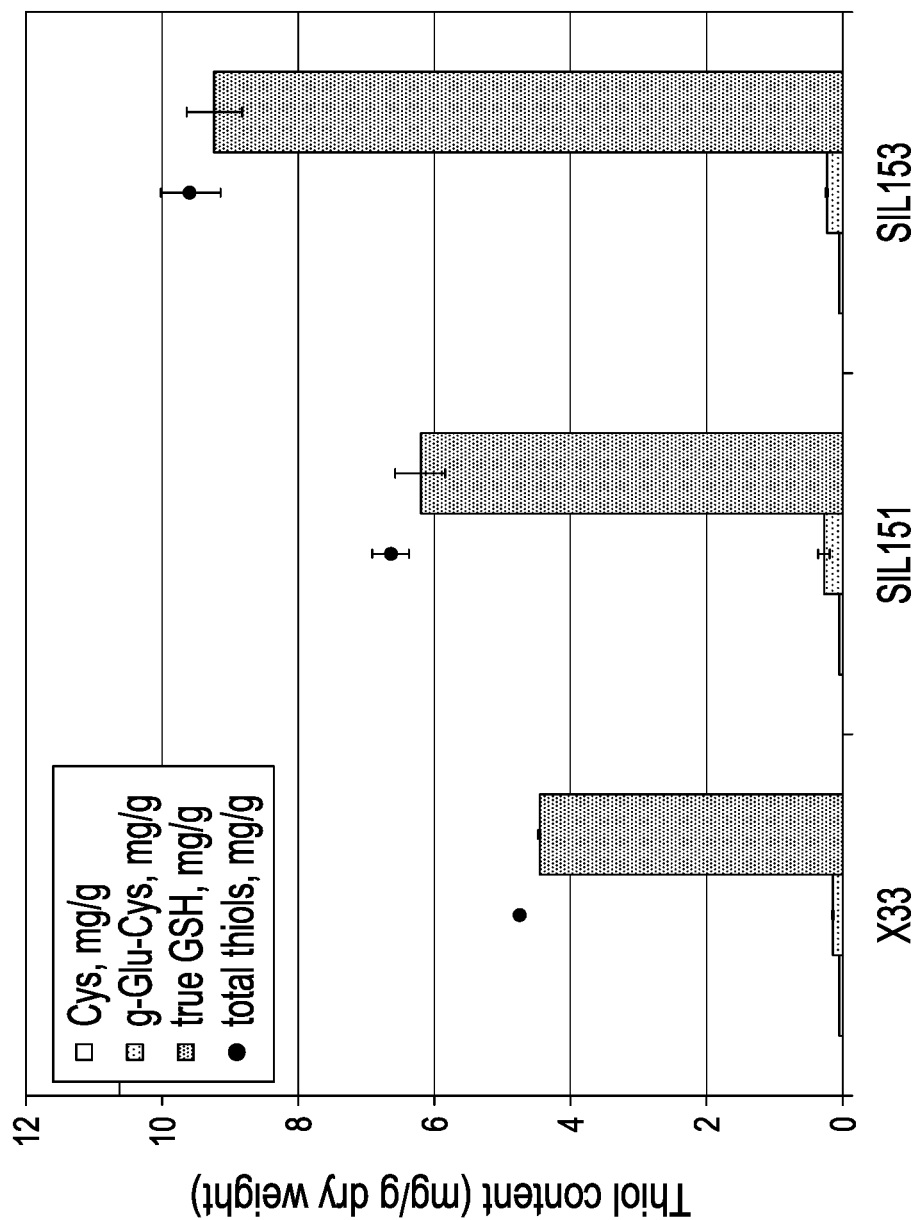
FIG. 6 provides cysteine (Cys), γ-L-glutamyl-L-cysteine (g-GC), true GSH and total thiol content of *P. pastoris* strains X33, SIL151 and SIL153 grown on minimal medium supplemented with cysteine (n=2). Values are provided as mg/g of dry weight in function of fermentation conditions.

The strain with wild-type CYS4 (SIL148) does not show an improvement in total thiol content compared to the wild-type strain. However, as shown in FIG. 5, the strain expressing CYS4.340 (SIL 150) has a 1.58-fold increase in true GSH content. This demonstrates that the mutated CYS4 (coding for Cys4p without its regulatory domain) has a positive effect on the GSH production in the genus *Komagataella*.

The strain SIL151, containing an extra copy of YAP1, shows a 1.39-fold increase in GSH content compared to the wild-type X-33. The integration of an extra copy of the mutated YAP1, YAP1.C414D, in strain SIL153, increased GSH production by 2.07-fold over of X-33, thus significantly more than wild-type YAP1. Strain SIL153 displayed a 1.48-fold increase in true GSH content over strain SIL151. This demonstrates that the mutated YAP1 has a positive effect on the GSH production in the genus *Komagataella*.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Aitken S M, Kirsch J F. Role of active-site residues Thr81, Ser82, Thr85, Gln157, and Tyr158 in yeast cystathionine beta-synthase catalysis and reaction specificity. Biochemistry. 2004 Feb. 24; 43(7):1963-71.
Blank H M, Gajjar S, Belyanin A, Polymenis M. Sulfur metabolism actively promotes initiation of cell division in yeast. PLoS One. 2009 Nov. 24; 4(11):e8018.
Chinese Patent Application CN 101220338 A
Chinese Patent Application CN 101245363 A
Jhee, K. H., P. McPhie, and E. W. Miles. 2000. Domain architecture of the heme-independent yeast cystathionine beta-synthase provides insights into mechanisms of catalysis and regulation. Biochemistry 39:10548-56.
Kuge, S., M. Arita, A. Murayama, K. Maeta, S. Izawa, Y. Inoue, and A. Nomoto. 2001. Regulation of the yeast Yap1p nuclear export signal is mediated by redox signal-induced reversible disulfide bond formation. Mol Cell Biol 21:6139-50.

Kuge, S., N. Jones, and A. Nomoto. 1997. Regulation of yAP-1 nuclear localization in response to oxidative stress. EMBO J 16:1710-20.

Nisamedtinov, I., Orumets, K., Kevvai, K., Viiard, E., Sarand, I., and Paalme, T. 2010. Multilevel Control of GSH Accumulation in Mutant and Wild-type Strains of S. cerevisiae Under Conditions of Smooth Cysteine Addition. 2010. Retrieved from http://wwwdotaidicdotit/ibic2010/webpapers/82Nisamedtinovdotpdf.

Nisamedtinov I, Kevvai K, Orumets K, Arike L, Sarand I, Korhola M, Paalme T. Metabolic changes underlying the higher accumulation of glutathione in Saccharomyces cerevisiae mutants. Appl Microbiol Biotechnol. 2011 February; 89(4):1029-37.

Orumets, K., K. Kewai, I. Nisamedtinov, T. Tamm, and T. Paalme. YAP1 over-expression in Saccharomyces cerevisiae enhances glutathione accumulation at its biosynthesis and substrate availability levels. 2012. Biotechnology J 7:566-568.

Suzuki, T., A. Yokoyama, T. Tsuji, E. Ikeshima, K. Nakashima, S. Ikushima, C. Kobayashi, and S. Yoshida. Identification and characterization of genes involved in glutathione production in yeast. 2011. J Biosci Bioeng 112:107-113.

What is claimed is:

1. A genetically modified host cell comprising at least two of:
   a first heterologous nucleic acid molecule encoding a mutated cystathionine beta-synthase protein (Cys4p) having an increased biological activity when compared to a wild-type Cys4p, wherein the mutated Cys4p is a fragment of the wild-type Cys4p;
   a second heterologous nucleic acid molecule encoding a mutated Yap1p having a reduced ability of being translocated from nucleus to cytoplasm of the genetically modified host cell when compared to a wild-type Yap1p, wherein the mutated Yap1p has at least one amino acid substitution when compared to the wild-type Yap1p; and
   a third heterologous nucleic acid molecule coding for a threonine aldolase protein (Gly1p), a variant of the Gly1p having threonine aldolase activity or a fragment of the Gly1p having threonine aldolase activity.

2. The genetically modified host cell of claim 1 comprising the first heterologous nucleic acid molecule and at least one of the second heterologous nucleic acid molecule or the third heterologous nucleic acid molecule.

3. The genetically modified host cell of claim 1, wherein the mutated Cys4p is obtained by deleting one or more C-terminal amino acid residue from the wild-type Cys4p.

4. The genetically modified host cell of claim 3, wherein the mutated Cys4p is obtained by deleting a Cys4p regulatory domain from the wild-type Cys4p.

5. The genetically modified host cell of claim 4, wherein the mutated Cys4p consists of the amino acid sequence set forth in SEQ ID NO: 2.

6. The genetically modified host cell of claim 1, wherein at least one copy of a native nucleic acid molecule coding for the wild-type Cys4p is replaced by the first heterologous nucleic acid molecule.

7. The genetically modified host cell of claim 1 comprising at least two, at least three or at least four copies of the first heterologous nucleic acid molecule.

8. The genetically modified host cell of claim 1, wherein the at least one amino acid substitution is located in a domain corresponding to a cysteine-rich domain of the wild-type Yap1p.

9. The genetically modified host cell of claim 8, wherein the mutated Yap1p is obtained by substituting a cysteine residue with a hydrophilic amino acid residue in the domain corresponding to the cysteine-rich domain of the wild-type Yap1p.

10. The genetically modified host cell of claim 9, wherein the hydrophilic amino acid residue is an aspartic acid residue.

11. The genetically modified host cell of claim 9, wherein the substituted cysteine residue is located at a position corresponding to residue 626 of SEQ ID NO: 3.

12. The genetically modified host cell of claim 11, wherein the mutated Yap1p comprises the amino acid sequence of SEQ ID NO: 4 or SEQ ID NO: 5.

13. The genetically modified host cell of claim 1, wherein at least one copy of the native nucleic acid molecule coding for the wild-type Yap1p is replaced by the second heterologous nucleic acid molecule.

14. The genetically modified host cell of claim 1 comprising at least two, at least three or at least four copies of the second heterologous nucleic acid molecule.

15. The genetically modified host cell of claim 1 comprising at least two, at least three or at least four copies of the third heterologous nucleic acid molecule.

16. The genetically modified host cell of claim 1 which comprises a genetically modified yeast host cell.

17. The genetically modified host cell of claim 16, wherein the genetically modified yeast host cell is a cell of genus *Saccharomyces*.

18. The genetically modified host cell of claim 17, wherein the genetically modified yeast host cell is a *Saccharomyces cerevisiae* cell.

19. The genetically modified host cell of claim 1 which is in an inactivated form.

20. The genetically modified host cell of claim 19 which comprises an extract or a hydrolysate.

21. A process of making glutathione, said process comprising fermenting a substrate with the genetically modified host cell of claim 1 to obtain a fermented mixture comprising glutathione.

22. The process of claim 21, wherein the genetically modified host cell comprises the first heterologous nucleic acid molecule and at least one of the second nucleic acid molecule or the third heterologous nucleic acid molecule.

23. The process of claim 21, wherein the mutated Cys4p is obtained by deleting one or more C-terminal amino acid residue from the wild-type Cys4p.

24. The process of claim 23, wherein the mutated Cys4p is obtained by deleting a regulatory domain from the wild-type Cys4p.

25. The process of claim 24, wherein the mutated Cys4p consists of the amino acid sequence of SEQ ID NO: 2.

26. The process of claim 21, wherein, in the genetically modified host cell, at least one copy of a native nucleic acid molecule coding for the wild-type Cys4p is replaced by the first heterologous nucleic acid molecule.

27. The process of claim 21, wherein the genetically modified host cell comprises at least one, at least two, at least three or at least four copies of the first heterologous nucleic acid molecule.

28. The process of claim 21, wherein the at least one amino acid substitution is located in a domain corresponding to a cysteine-rich domain of the wild-type Yap1p.

29. The process of claim 28, wherein the mutated Yap1p is obtained by substituting a cysteine residue with an hydrophilic amino acid residue in the domain corresponding to the cysteine-rich domain of the wild-type Yap1p.

30. The process of claim 29, wherein the hydrophilic amino acid residue is an aspartic acid residue.

31. The process of claim 29, wherein the substituted cysteine residue is located at a position corresponding to residue 626 of SEQ ID NO: 3.

32. The process of claim 31, wherein the mutated Yap1p comprises the amino acid sequence of SEQ ID NO: 4 or SEQ ID NO: 5.

33. The process of claim 21, further comprising processing the fermented mixture into a yeast extract or a yeast hydrolysate.

34. The process of claim 21, further comprising purifying glutathione from the fermented mixture.

35. The process of claim 21, wherein the genetically modified host cell is a cell of genus *Saccharomyces*.

36. The process of claim 21, wherein the genetically modified host cell is a *Saccharomyces cerevisiae* cell.

37. A yeast extract or a yeast hydrolysate obtainable by the process of claim 33.

* * * * *